United States Patent
Yu et al.

(10) Patent No.: US 10,233,193 B2
(45) Date of Patent: Mar. 19, 2019

(54) FUSED TRICYCLIC HETEROCYCLIC COMPOUNDS USEFUL FOR TREATING HIV INFECTION

(71) Applicants: MERCK SHARP & DOHME CORP., Rahway, NJ (US); Tao Yu, Edison, NJ (US); Thomas H. Graham, Quincy, MA (US); Sherman T. Waddell, Westfield, NJ (US); John A. McCauley, Maple Glen, PA (US); Andrew W. Stamford, Chatham, NJ (US); John M. Sanders, Hatfield, PA (US); Lihong Hu, Shanghai (CN); Jiaqiang Cai, Shanghai (CN); Lianyun Zhao, Shanghai (CN)

(72) Inventors: Tao Yu, Edison, NJ (US); Thomas H. Graham, Quincy, MA (US); Sherman T. Waddell, Westfield, NJ (US); John A. McCauley, Maple Glen, PA (US); Andrew W. Stamford, Chatham, NJ (US); John M. Sanders, Hatfield, PA (US); Lihong Hu, Shanghai (CN); Jiaqiang Cai, Shanghai (CN); Lianyun Zhao, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/575,433

(22) PCT Filed: May 20, 2016

(86) PCT No.: PCT/US2016/033414
§ 371 (c)(1),
(2) Date: Nov. 20, 2017

(87) PCT Pub. No.: WO2016/191239
PCT Pub. Date: Dec. 1, 2016

(65) Prior Publication Data
US 2018/0194774 A1   Jul. 12, 2018

(30) Foreign Application Priority Data
May 25, 2015 (WO) ............... PCT/CN2015/079730

(51) Int. Cl.
| | | |
|---|---|---|
| A61K 31/4375 | (2006.01) | |
| C07D 491/147 | (2006.01) | |
| A61K 31/4355 | (2006.01) | |
| A61K 31/437 | (2006.01) | |
| C07D 471/14 | (2006.01) | |
| A61K 31/427 | (2006.01) | |
| A61K 31/4402 | (2006.01) | |
| A61K 31/505 | (2006.01) | |
| A61K 31/513 | (2006.01) | |
| A61K 31/52 | (2006.01) | |
| A61K 31/635 | (2006.01) | |
| A61K 31/675 | (2006.01) | |
| A61P 31/18 | (2006.01) | |

(52) U.S. Cl.
CPC ........ *C07D 491/147* (2013.01); *A61K 31/427* (2013.01); *A61K 31/437* (2013.01); *A61K 31/4355* (2013.01); *A61K 31/4375* (2013.01); *A61K 31/4402* (2013.01); *A61K 31/505* (2013.01); *A61K 31/513* (2013.01); *A61K 31/52* (2013.01); *A61K 31/635* (2013.01); *A61K 31/675* (2013.01); *A61P 31/18* (2018.01); *C07D 471/14* (2013.01)

(58) Field of Classification Search
CPC ......................... C07D 471/14; A61K 31/4375
See application file for complete search history.

(56) References Cited

U.S. PATENT DOCUMENTS

| 8,129,385 B2 | 3/2012 | Johns et al. |
|---|---|---|
| 2012/0108564 A1 | 5/2012 | Miyazaki et al. |

FOREIGN PATENT DOCUMENTS

| EP | 1950212 | 7/2008 |
|---|---|---|
| WO | 2006066414 A1 | 6/2006 |

(Continued)

OTHER PUBLICATIONS

Coffin, retrieved from http://now.tufts.edu/print/articles/why-can-t-current-drugs-cure-hiv-infection on Jun. 11, 2018, p. 1-2. (Year: 2016).*

(Continued)

*Primary Examiner* — Rebecca L Anderson
*Assistant Examiner* — Karen Cheng
(74) *Attorney, Agent, or Firm* — Nicole M. Beeler; John C. Todaro

(57) ABSTRACT

The present invention relates to Fused Tricyclic Heterocycle Derivatives of Formula (I): and pharmaceutically acceptable salts thereof, wherein A, B, X, Y, m, $R^1$, $R^2$, $R^3$, $R^3$, $R^3$, $R^4$, $R^5$ and $R^9$ are as defined herein. The present invention also relates to compositions comprising at least one Fused Tricyclic Heterocycle Derivative, and methods of using the Fused Tricyclic Heterocycle Derivatives for treating or preventing HIV infection in a subject.

19 Claims, No Drawings

(56) References Cited

FOREIGN PATENT DOCUMENTS

| WO | 2012151361 | A1 | 11/2012 |
| WO | 2014018449 | A1 | 1/2014 |
| WO | 2014200880 | A1 | 12/2014 |
| WO | 2015048363 | | 4/2015 |
| WO | 2015095258 | A1 | 6/2016 |
| WO | 2016154527 | A1 | 9/2016 |
| WO | 2017087256 | A1 | 5/2017 |
| WO | 2017087257 | A1 | 5/2017 |
| WO | 2017106071 | A1 | 6/2017 |

OTHER PUBLICATIONS

Peirce, retrieved from https://www.everydayhealth.com/hiv-aids/can-you-prevent-aids-when-you-have-hiv.aspx?sa on Jun. 8, 2018, p. 1-3. (Year: 2017).*
International Search Report and Written Opinion for PCT/CN2015/079730 dated Feb. 25, 2016, 17 pages.
International Search Report and Written Opinion for PCT/US2016/033414 dated Sep. 1, 2016, 8 pages.

* cited by examiner

FUSED TRICYCLIC HETEROCYCLIC COMPOUNDS USEFUL FOR TREATING HIV INFECTION

CROSS REFERENCE TO RELATED APPLICATIONS

This application is a U.S. National Phase application under 35 U.S.C. § 371 of PCT Application No. PCT/US2016/033414 filed May 20, 2016, which claims priority from PCT Application Application No. PCT/CN2015/079730 filed May 25, 2015.

FIELD OF THE INVENTION

The present invention relates to Fused Tricyclic Heterocycle Derivatives, compositions comprising at least one Fused Tricyclic Heterocycle Derivative, and methods of using the Fused Tricyclic Heterocycle Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Tohours, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

The following references may be of interest as background:

International Publication Nos. WO 11/045330 and WO 11/121105 disclose macrocyclic compounds having HIV integrase inhibitory activity.

Kinzel et al., Tet. Letters 2007, 48(37): pp. 6552-6555 discloses the synthesis of tetrahydropyridopyrimidones as a scaffold for HIV-1 integrase inhibitors.

Ferrara et al., Tet. Letters 2007, 48(37), pp. 8379-8382 discloses the synthesis of a hexahydropyrimido[1,2-a]azepine-2-carboxamide derivative useful as an HIV integrase inhibitor.

Muraglia et al., J. Med. Chem. 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. Nos. 7,169,780, 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that may be useful as HIV integrase inhibitors.

U.S. Pat. Nos. 7,135,467 and 7,037,908 disclose certain pyrimidine carboxamides that may be useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that may be useful as HIV integrase inhibitors.

U.S. Pat. No. 8,129,385 discloses certain hexahydro-2H-pyrido[1',2':4,5]pyrazino[2,1-b][1,3]oxazine-9-carboxamides, and related compounds that may be useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that may be useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. Nos. 7,115,601, 7,157,447, 7,173,022, 7,176,196, 7,192,948, 7,273,859, and 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

U.S. Pat. Nos. 7,462,608 and 7,649,015 each disclose phosphate and phosphonate-substituted heterocycles useful as HIV nNRTI inhibitors and HIV protease inhibitors, respectively.

SUMMARY OF THE INVENTION

In one aspect, the present invention provides Compounds of Formula (I):

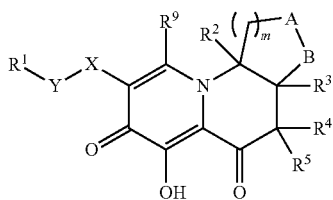

(I)

and pharmaceutically acceptable salts thereof,
wherein:

the group -A-B— is selected from —O—C(R$^{13}$)$_2$—, —O—C(R$^{13}$)$_2$—C(R$^{13}$)$_2$—, —C(R$^{13}$)$_2$—O—, —N(R$^{14}$)—C(R$^{13}$)$_2$—, —N(R$^{14}$)—C(R$^{13}$)$_2$—C(R$^{13}$)$_2$— and —C(R$^{13}$)$_2$—N(R$^{14}$)—;

X is selected from a single bond, 5 or 6-membered monocyclic heteroaryl and —N(R$^6$)C(O)—;

Y is a single bond or C$_1$-C$_3$ alkylene;

R$^1$ is selected from C$_6$-C$_{10}$ aryl, 5 or 6-membered monocyclic heteroaryl and 9 or 10-membered bicyclic heteroaryl, wherein said C$_6$-C$_{10}$ aryl group, said 5 or 6-membered monocyclic heteroaryl group and said 9 or 10-membered bicyclic heteroaryl group can each be optionally substituted with up to three R$^8$ groups;

R$^2$ is selected from H, C$_1$-C$_6$ alkyl, —(C$_1$-C$_6$ alkylene)$_m$-Z—R$^{16}$, —N(R$^{25}$)$_2$, —N(R$^{11}$)$_2$ and —OR$^7$;

R$^3$ is selected from H, C$_1$-C$_6$ alkyl, —(C$_1$-C$_6$ alkylene)$_m$-Z—R$^{16}$, —N(R$^{25}$)$_2$, —N(R$^{11}$)$_2$ and —OR$^7$;

R$^4$ is selected from H, C$_1$-C$_6$ alkyl, C$_1$-C$_6$ haloalkyl, C$_2$-C$_6$ alkenyl, —(C$_1$-C$_6$ alkylene)-O—(C$_1$-C$_6$ alkyl), —(C$_1$-C$_6$ alkylene)$_m$-Z—R$^{16}$, —N(R$^{25}$)$_2$, —N(R$^{11}$)$_2$ and —OR$^7$, or R$^4$ and R$^5$ and the common carbon atom to which they are attached, join to form an exocyclic olefin group having the formula:

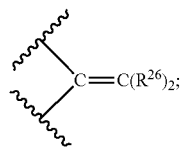

R$^5$ is selected from H, C$_1$-C$_6$ alkyl, C$_2$-C$_6$ alkenyl, —(C$_1$-C$_6$ alkylene)-O—(C$_1$-C$_6$ alkyl), —N(R$^{11}$)$_2$ and —OR$^7$;

each occurrence of R$^6$ is independently selected from H, C$_1$-C$_6$ alkyl, —(C$_1$-C$_6$ alkylene)$_m$-Z—R$^{16}$ and —N(R$^{25}$)$_2$;

each occurrence of R$^7$ is independently selected from H, C$_1$-C$_6$ alkyl, —(C$_1$-C$_6$ alkylene)-O—(C$_1$-C$_6$ alkyl) and C$_3$-C$_7$ cycloalkyl;

each occurrence of R$^8$ is independently selected from C$_1$-C$_6$ alkyl, halo, —OR$^{15}$, —SR$^{15}$, C$_1$-C$_6$ haloalkyl, C$_1$-C$_6$ hydroxyalkyl, —O—(C$_1$-C$_6$ haloalkyl), —CN, —NO$_2$, —N(R$^{15}$)$_2$, R$^{16}$, —C(O)OR$^7$, —C(O)N(R$^7$)$_2$ and —NHC(O)R$^7$;

R$^9$ is selected from H, C$_1$-C$_6$ alkyl, —(C$_1$-C$_6$ alkylene)-O—C$_1$-C$_6$ alkyl, —(C$_1$-C$_6$ alkylene)-N(R$^{15}$)—C$_1$-C$_6$ alkyl, —C$_1$-C$_6$ haloalkyl, —C$_1$-C$_6$ hydroxyalkyl;

each occurrence of R$^{10}$ is independently selected from H and C$_1$-C$_6$ alkyl;

each occurrence of R$^{11}$ is independently selected from H, C$_1$-C$_6$ alkyl, —S(O)$_2$R$^{12}$ and —C(O)R$^{12}$;

each occurrence of R$^{12}$ is independently selected from H, C$_1$-C$_6$ alkyl, C$_3$-C$_7$ cycloalkyl, C$_6$-C$_{10}$ aryl, 4 to 7-membered monocyclic heterocycloalkyl, 8 to 11-membered bicyclic heterocycloalkyl, 5 or 6-membered monocyclic heteroaryl and 9 or 10-membered bicyclic heteroaryl, wherein said C$_3$-C$_7$ cycloalkyl group, said C$_6$-C$_{10}$ aryl group, said 4 to 7-membered monocyclic heterocycloalkyl, said 8 to 11-membered bicyclic heterocycloalkyl group, said 5 or 6-membered monocyclic heteroaryl group and said 9 or 10-membered bicyclic heteroaryl group can each be optionally substituted with up to three R$^8$ groups;

each occurrence of R$^{13}$ is independently selected from H, C$_1$-C$_6$ alkyl, C$_3$-C$_7$ cycloalkyl, halo, C$_1$-C$_6$ haloalkyl, —(C$_1$-C$_6$ alkylene)$_m$-Z—R$^{16}$, —N(R$^{25}$)$_2$, —C(O)R$^{15}$, —C(O)N(R$^{15}$)$_2$ and —NHC(O)R$^{15}$;

each occurrence of R$^{14}$ is independently selected from H, C$_1$-C$_6$ alkyl, —(C$_1$-C$_6$ alkylene)$_m$-Z—R$^{16}$, C$_3$-C$_7$ cycloalkyl and C$_6$-C$_{10}$ aryl, wherein said C$_3$-C$_7$ cycloalkyl group and said C$_6$-C$_{10}$ aryl group can be optionally substituted with one or more groups, each independently selected from C$_1$-C$_6$ alkyl, C$_3$-C$_7$ cycloalkyl, C$_6$-C$_{10}$ aryl, halo, C$_1$-C$_6$ haloalkyl, —C(O)R$^{15}$, —C(O)OR$^{15}$, —C(O)N(R$^{15}$)$_2$, —NHC(O)R$^{15}$ and —S(O)$_2$R$^{15}$;

each occurrence of R$^{15}$ is independently selected from H, C$_1$-C$_6$ alkyl, C$_3$-C$_7$ cycloalkyl, C$_6$-C$_{10}$ aryl and benzyl; and each occurrence of R$^{16}$ is independently selected from —P(O)(—OR$^{24}$)$_2$,

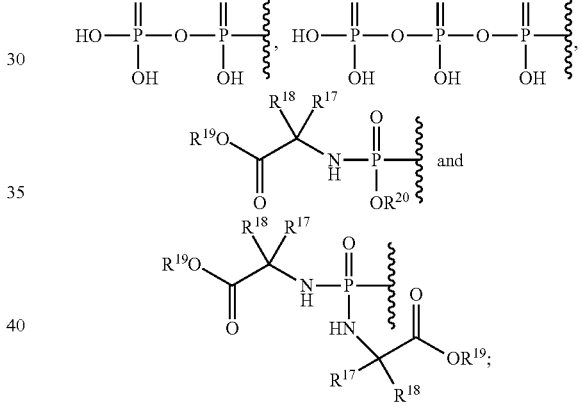

each occurrence of R$^{17}$ is independently selected from H, C$_1$-C$_6$ alkyl, C$_3$-C$_7$ cycloalkyl, phenyl and benzyl, wherein said C$_1$-C$_6$ alkyl can be optionally substituted with a group selected from halo, —OR$^{21}$, —SR$^{21}$, guanidino, —N(R$^{21}$)$_2$, —C(O)OR$^{21}$, —C(O)N(R$^{21}$)$_2$, —NHC(O)R$^{21}$, 5- or 6-membered monocyclic heteroaryl and 9- or 10-membered bicyclic heteroaryl, and wherein said phenyl group and said benzyl group can be optionally substituted with up to 2 groups, each independently selected from C$_1$-C$_6$ alkyl, halo and —OR$^{26}$;

each occurrence of R$^{18}$ is independently selected from H, C$_1$-C$_6$ alkyl, C$_3$-C$_7$ cycloalkyl, phenyl and benzyl, wherein said C$_1$-C$_6$ alkyl can be optionally substituted with a group selected from halo, —OR$^{21}$, —SR$^{21}$, guanidino, —N(R$^{21}$)$_2$, —C(O)OR$^{21}$, —C(O)N(R$^{21}$)$_2$, —NHC(O)R$^{21}$, 5- or 6-membered monocyclic heteroaryl and 9- or 10-membered bicyclic heteroaryl, and wherein said phenyl group and said benzyl group can be optionally substituted with up to 2 groups, each independently selected from C$_1$-C$_6$ alkyl, halo and —OR$^{21}$;

each occurrence of R$^{19}$ is independently selected from H, C$_1$-C$_{20}$ alkyl, C$_2$-C$_{20}$ alkenyl, —(C$_1$-C$_3$ alkylene)$_m$-(C$_3$-C$_7$ cycloalkyl), —(C$_1$-C$_3$ alkylene)$_m$-(C$_6$-C$_{10}$ aryl) and —(C$_1$-

$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group can be optionally substituted with up to three groups, each independently selected from halo, —OR$^{21}$, —C(O)OR$^{21}$, —CN, —NO$_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —N(R$^{21}$)$_2$, —C(O)N(R$^{21}$)$_2$, —SR$^{21}$, —S(O)R$^{21}$, —S(O)$_2$R$^{21}$, —S(O)$_2$N(R$^{21}$)$_2$, —NHC(O)R$^{21}$, —NHC(O)OR$^{21}$ and —NHC(O)N(R$^{21}$)$_2$;

each occurrence of R$^{20}$ is independently selected from H, $C_6$-$C_{10}$ aryl, 5- or 6-membered monocyclic heteroaryl and 9- or 10-membered bicyclic heteroaryl, wherein said $C_6$-$C_{10}$ aryl group, said 5- or 6-membered monocyclic heteroaryl group and said 9- or 10-membered bicyclic heteroaryl group can be optionally substituted with up to five R$^{22}$ groups;

each occurrence of R$^{21}$ is independently H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group can be optionally substituted with up to five R$^{22}$ groups;

each occurrence of R$^{22}$ is independently selected from $C_1$-$C_6$ alkyl, halo, —OR$^{21}$, —SR$^{21}$, $C_1$-$C_6$ haloalkyl, $C_1$-$C_6$ hydroxyalkyl, —O—($C_1$-$C_6$ haloalkyl), —CN, —NO$_2$, —N(R$^{21}$)$_2$, —C(O)OR$^{21}$, —C(O)N(R$^{21}$)$_2$ and —NHC(O)R$^{21}$, or any two R$^{22}$ groups on adjacent ring carbon atoms can combine to form —O—R$^{23}$—O—;

R$^{23}$ is —[C(R$^{10}$)$_2$]$_n$—;

each occurrence of R$^{24}$ is independently selected from H, $C_1$-$C_6$ alkyl, $C_6$-$C_{10}$ aryl, —($C_1$-$C_6$ alkylene)-O—($C_1$-$C_{20}$ alkyl), —($C_1$-$C_6$ alkylene)-O—C(O)—R$^{21}$, and —($C_1$-$C_6$ alkylene)-O—C(O)O—R$^{21}$;

each occurrence of R$^{25}$ is independently selected from H, $C_1$-$C_6$ alkyl and —($C_1$-$C_6$ alkylene)-Z—R$^{16}$;

each occurrence of Z is independently —O— or a bond;

each occurrence of m is independently 0, 1 or 2; and n is 1 or 2.

The Compounds of Formula (I) (also referred to herein as the "Fused Tricyclic Heterocycle Derivatives") and pharmaceutically acceptable salts thereof may be useful, for example, for inhibiting HIV viral replication or replicon activity, and for treating or preventing HIV infection in a subject. Without being bound by any specific theory, it is believed that the Fused Tricyclic Heterocycle Derivatives inhibit HIV viral replication by inhibiting HIV Integrase.

Accordingly, the present invention provides methods for treating or preventing HIV infection in a subject, comprising administering to the subject an effective amount of at least one Fused Tricyclic Heterocycle Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to Fused Tricyclic Heterocycle Derivatives, compositions comprising at least one Fused Tricyclic Heterocycle Derivative, and methods of using the Fused Tricyclic Heterocycle Derivatives for inhibiting HIV integrase, inhibiting HIV viral replication or for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Fused Tricyclic Heterocycle Derivative and/or an additional therapeutic agent, or a composition thereof that is effective in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different. Illustrative examples of substituents include, but are not limited to, halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms. The term "C$_3$-C$_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 2 to about 4 carbon atoms. In another embodiment, an alkenylene group is branched. In another embodiment, an alkenylene group is linear. The term "C$_2$-C$_6$ alkenylene" refers to an alkenylene group having from 2 to 6 carbon atoms. The term "C$_2$-C$_4$ alkenylene" refers to an alkylene group having from 2 to 4 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

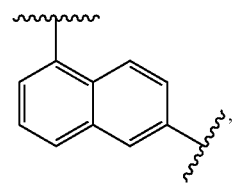 [SMILES: *c1ccc2c(*)cccc2c1]

is understood to represent both:

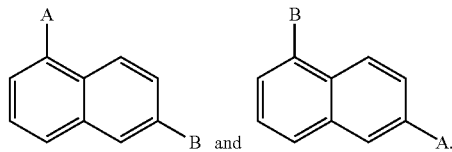

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

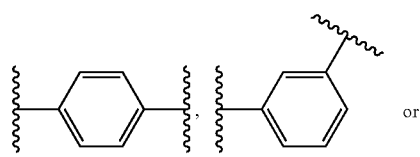

-continued

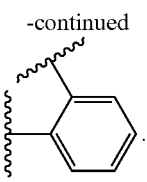

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring, such as tetrahydronaphthalene and the like. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

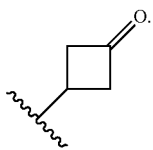 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,3,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring, such as dihydrobenzofuran and the like. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, pyranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

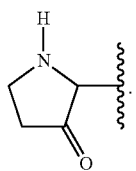 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "ring system substituent," as used herein, refers to a substituent group attached to an aromatic or non-aromatic ring system which, for example, replaces an available hydrogen on the ring system. Ring system substituents may be the same or different. Illustrative examples of ring system substituents include, but are not limited to, alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

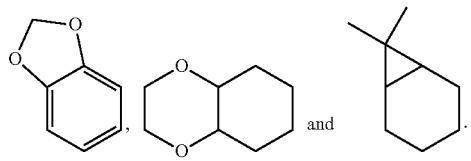

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R$^1$, R$^7$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Fused Tricyclic Heterocycle Derivative or a pharmaceutically acceptable salt of the compound. The transformation may occur by various mechanisms (e.g., by metabolic or chemical processes), such as, for example, through hydrolysis in blood. For example, if a Fused Tricyclic Heterocycle Derivative or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a Fused Tricyclic Heterocycle Derivative contains an alcohol functional group, a prodrug can be formed by the replacement of one or more of the hydrogen atoms of the alcohol groups with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$) alkoxycarbonyloxymethyl, N—($C_1$-$C_6$)alkoxycarbonylaminomethyl, succinoyl, ($C_1$-$C_6$)alkanoyl, α-amino($C_1$-$C_4$) alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Fused Tricyclic Heterocycle Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)O$Y^1$ wherein $Y^1$ is H, ($C_1$-$C_6$) alkyl or benzyl, —C(O$Y^2$)$Y^3$ wherein $Y^2$ is ($C_1$-$C_4$) alkyl and $Y^3$ is ($C_1$-$C_6$)alkyl; carboxy ($C_1$-$C_6$)alkyl; amino($C_1$-$C_4$)alkyl or mono-N- or di-N,N—($C_1$-$C_6$)alkylaminoalkyl; —C($Y^4$)$^5$ wherein $Y^4$ is H or methyl and $Y^5$ is mono-N- or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Fused Tricyclic Heterocycle Derivatives can form salts which are also within the scope of this invention. Reference to a Fused Tricyclic Heterocycle Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Fused Tricyclic Heterocycle Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Fused Tricyclic Heterocycle Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Fused Tricyclic Heterocycle Derivatives may be atropisomers (e.g., substituted biaryls) and are considered as part of this invention. Enantiomers can also be directly separated using chiral chromatographic techniques.

It is also possible that the Fused Tricyclic Heterocycle Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Fused Tricyclic Heterocycle Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Fused Tricyclic Heterocycle Derivatives, and of the salts, solvates, hydrates, esters and prodrugs of the Fused Tricyclic Heterocycle Derivatives, are intended to be included in the present invention.

Ac=acetyl
ACN=acetonitrile
BOC=t-butyloxycarbonyl
BOP=bis(2-oxo-3-oxazolidino)phosphinyl
t-BuOH=tert-butyl alcohol
CBz=carboxybenzyl
CM=dichloromethane
Dess Martin Periodinane=1,1,1-Triacetoxy-1,1-dihydro-1,2-benziodoxol-(1H)-one
DIAD=diisopropylazodicarboxylate
DMA=dimethylacetamide
DMF=dimethylformamide
DMSO=dimethyl sulfoxide
ECHO=Echo liquid handling systems
ESI=electrospray ionization
Et=ethyl
EtOAc=ethyl acetate
EtOH=ethanol
Et$_3$N=triethylamine
FBS=fetal bovine serum
HRMS=high resolution mass spectrometry
LCMS=liquid chromatography/mass sepectrometry
LiHMDS=lithium bis(trimethylsilyl)amide
Me=methyl
MeOH=methanol
MOMCl=methoxylmethyl chloride
MS=mass spectroscopy
NBS=N-bromosuccinimide
NIS=N-iodosuccinimide
NMR=nuclear magnetic resonance spectroscopy
Pd(Ph$_3$P)$_4$=tetrakis(triphenylphosphine) palladium(0)
PE or PET=petroleum ether
Ph=phenyl
RPMI=Roswell Park Memorial Institute Media
SFC=supercritical fluid chromatography
t=triplet
TBDPS=t-butyldiphenylsilane
TEA or Et$_3$N=triethylamine
TFA=trifluoroacetic acid
THF=tetrahydrofuran
TLC=thin-layer chromatography
TMS=trimethylsilyl
Ts or Tos=p-toluenesulfonyl The Compounds of Formula (I)

The present invention provides Fused Tricyclic Heterocycle Derivatives of Formula (I):

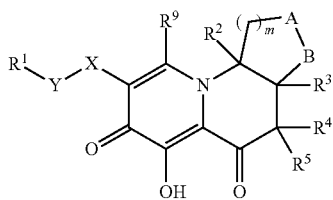

and pharmaceutically acceptable salts thereof, wherein A, B, X, Y, m, $R^1$, $R^2$, $R^3$, $R^3$, $R^3$, $R^4$, $R^5$ and $R^9$ are as defined above for the Compounds of Formula (I).

In one embodiment, the group -A-B— is selected from —$CH_2$—N($CH_3$)—, —O—$CH_2$—, —O—$CH_2$—$CH_2$— and —$CH_2$—O—.

In one embodiment, X is a single bond.
In another embodiment, X is —NHC(O)—.
In another embodiment, X is 5 or 6-membered monocyclic heteroaryl.
In still another embodiment, X is 5-membered monocyclic heteroaryl.
In another embodiment, X is 1,3,4-thiadiazole.
In one embodiment, Y is a single bond.
In another embodiment, Y is $C_1$-$C_3$ alkylene.
In another embodiment, Y is $CH_2$.
In one embodiment, X is —NHC(O)— and Y is $CH_2$.
In another embodiment, X is 5-membered heteroaryl and Y is $CH_2$.
In one embodiment, m is 0.
In another embodiment, m is 1.
In one embodiment, the group $R^1$—Y— is phenyl-$CH_2$—, wherein said phenyl group is substituted with 1-3 groups, independently selected from F and Cl.
In another embodiment, the group $R^1$—Y— is phenyl-$CH_2$—, wherein said phenyl group is substituted with one or two F groups.
In one embodiment, $R^6$ is —($C_1$-$C_6$ alkylene)$_m$-Z—$R^{16}$ or —N($R^{25}$)$_2$.
In one embodiment, $R^9$ is H.
In another embodiment, $R^{13}$ is —($C_1$-$C_6$ alkylene)$_m$-Z—$R^{16}$ or —N($R^{25}$)$_2$.
In yet another embodiment, $R^{14}$ is —($C_1$-$C_6$ alkylene)$_m$-Z—$R^{16}$.
In one embodiment, the $R^{16}$ moiety of a —($C_1$-$C_6$ alkylene)$_m$-Z—$R^{16}$ group is independently selected from: —P(O)(—OH)$_2$, —P(O)(—OCH$_3$)$_2$, —P(O)(—OCH$_2$CH$_3$)$_2$, —P(O)(—CH$_2$OC(O)O—CH(CH$_3$)$_2$)$_2$, —P(O)(—CH$_2$OC(O)O—CH$_2$CH$_3$)$_2$ and

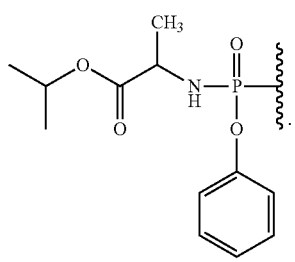 [SMILES: *P(=O)(NC(C)C(=O)OC(C)C)Oc1ccccc1]

In one embodiment, the $R^{25}$ moiety of an —N($R^{25}$)$_2$ group is independently selected from —P(O)(—OH)$_2$, —P(O)(—OCH$_3$)$_2$, —P(O)(—OCH$_2$CH$_3$)$_2$, —P(O)(—CH$_2$OC(O)OCH(CH$_3$)$_2$)$_2$, —P(O)(—CH$_2$OC(O)O—CH(CH$_3$)$_2$)$_2$ and

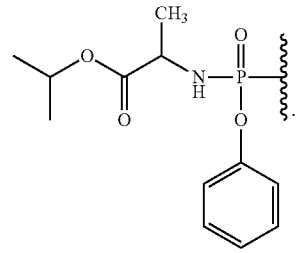 [SMILES: *P(=O)(NC(C)C(=O)OC(C)C)Oc1ccccc1]

In one embodiment, the compounds of formula (I) have the formula (Ia):

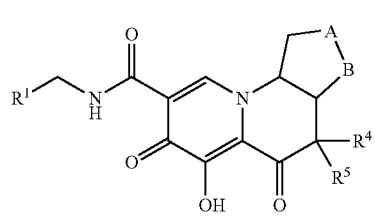

or a pharmaceutically acceptable salt thereof,
wherein:
the group -A-B— is selected from —$CH_2$—N($CH_3$)—, —O—$CH_2$—, —O—$CH_2$—$CH_2$— and —$CH_2$—O—.
$R^1$ is phenyl, which is substituted by up to three $R^8$ groups.
$R^4$ is selected from $C_1$-$C_6$ alkyl and —($C_1$-$C_6$ alkylene)-O—($C_1$-$C_6$ alkyl); and
$R^5$ is $C_1$-$C_6$ alkyl.

In one embodiment, for the compounds of formula (I) or (Ia), the group -A-B— is —O—$CH_2$—.
In another embodiment, for the compounds of formula (I) or (Ia), the group -A-B— is —O—$CH_2$—$CH_2$—
In still another embodiment, for the compounds of formula (I) or (Ia), the group -A-B— is —$CH_2$—O—.
In another embodiment, for the compounds of formula (I) or (Ia), the group -A-B— is —$CH_2$—N($CH_3$)—.
In one embodiment, for the compounds of formula (I) or (Ia), $R^1$ is optionally substituted $C_6$-$C_{10}$ aryl or optionally substituted 5 or 6-membered monocyclic heteroaryl.
In another embodiment, for the compounds of formula (I) or (Ia), $R^1$ is optionally substituted $C_6$-$C_{10}$ aryl.
In another embodiment, for the compounds of formula (I) or (Ia), $R^1$ is phenyl, substituted by up to three $R^8$ groups.
In one embodiment, for the compounds of formula (I) or (Ia), $R^1$ is selected from:

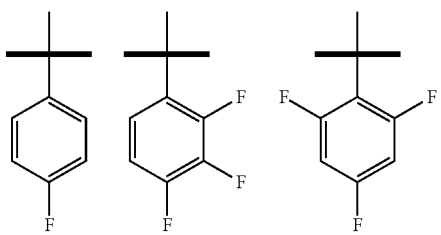

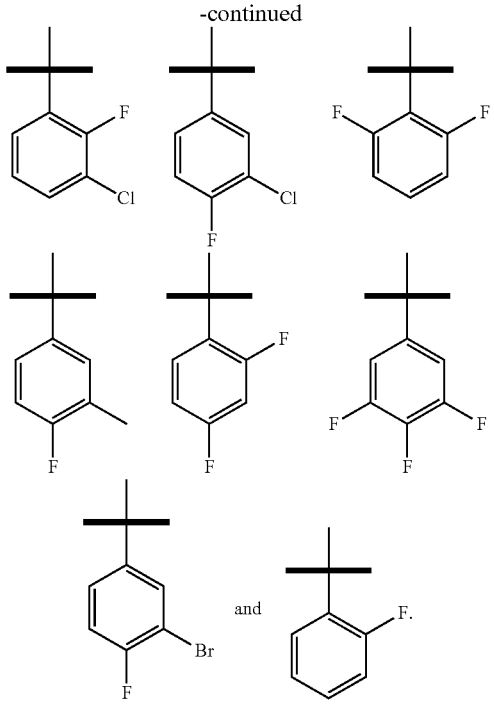

In another embodiment, for the compounds of formula (I) or (Ia), $R^1$ is phenyl which is substituted with one or more halo groups, which can be the same or different.

In another embodiment, for the compounds of formula (I) or (Ia), $R^1$ is phenyl which is substituted with 1-3 halo groups.

In still another embodiment, for the compounds of formula (I) or (Ia), $R^1$ is phenyl which is substituted with one or two F groups.

In one embodiment, for the compounds of formula (I) or (Ia), $R^1$ is 2,4-difluorophenyl, 3-chloro-2,4-difluorophenyl or 3-chloro-2-fluorophenyl.

In another embodiment, for the compounds of formula (I) or (Ia), $R^1$ is 4-fluorophenyl.

In yet another embodiment, for the compounds of formula (I) or (Ia), $R^1$ is 2,4-difluorophenyl.

In another embodiment, for the compounds of formula (I) or (Ia), $R^1$ is 3-chloro-2-fluorophenyl.

In one embodiment, for the compounds of formula (I) or (Ia), $R^4$ is H.

In another embodiment, for the compounds of formula (I) or (Ia), $R^4$ is $C_1$-$C_6$ alkyl.

In another embodiment, for the compounds of formula (I) or (Ia), $R^4$ is methyl.

In still another embodiment, for the compounds of formula (I) or (Ia), $R^4$ is —($C_1$-$C_6$ alkylene)-O—($C_1$-$C_6$ alkyl).

In one embodiment, for the compounds of formula (I) or (Ia), $R^4$ is H, methyl, ethyl, isopropyl, n-propyl or —$CH_2CH_2OCH_3$.

In another embodiment, for the compounds of formula (I) or (Ia), $R^4$ is —$CH_2CH_2$—O—$CH_3$.

In another embodiment, for the compounds of formula (I) or (Ia), $R^4$ is —($C_1$-$C_6$ alkylene)$_m$-Z—$R^{16}$ or —N($R^{25}$)$_2$.

In one embodiment, for the compounds of formula (I) or (Ia), $R^5$ is H.

In another embodiment, for the compounds of formula (I) or (Ia), $R^5$ is $C_1$-$C_6$ alkyl.

In another embodiment, for the compounds of formula (I) or (Ia), $R^5$ is methyl.

In still another embodiment, for the compounds of formula (I) or (Ia), $R^4$ and $R^5$ are each $C_1$-$C_6$ alkyl.

In another embodiment, for the compounds of formula (I) or (Ia), $R^4$ and $R^5$ are each methyl.

In one embodiment, for the compounds of formula (Ia), $R^8$ represents 1 to 3 halo groups.

In another embodiment, for the compounds of formula (Ia), $R^8$ represents 1 to 3 F groups.

In another embodiment, for the compounds of formula (Ia), $R^8$ represents two F groups, one in the ortho position and one in the para position.

In one embodiment, for the compounds of formula (I) or (Ia), at least one —($C_1$-$C_6$ alkylene)$_m$-Z—$R^{16}$ group or one —N($R^{25}$)$_2$ group is present in a compound of formula (I) or (Ia).

In one embodiment, variables A, B, X, Y, m, $R^1$, $R^2$, $R^3$, $R^3$, $R^3$, $R^4$, $R^5$ and $R^9$ for the Compounds of Formula (I) are selected independently of each other.

It is to be understood that any of the aforementioned embodiments can be combined with one or more separate embodiments.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, nucleoside reverse transcriptase inhibitors, CCR5 co-receptor antagonists, fusion and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, nucleoside reverse transcriptase inhibitors, CCR5 co-receptor antagonists, fusion and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-20 as set forth in the Examples below, and pharmaceutically acceptable salts thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-D, below. Alternative synthetic pathways and analogous structures will be apparent to those skilled in the art of organic synthesis. Unless otherwise indicated, all variables are as defined above.

Scheme A depicts a general method for preparing compounds of the present invention wherein a cyclic diamine B is condensed into a pyranone A to provide the intermediate pyridinone, which then cyclizes to form the lactam C. This reaction may need in-situ protection of one of the amines by the addition of benzaldehyde followed later by in-situ deprotection with water. The lactam is then alkyated to provide D. The same conditions can also provide compounds with branching off of the benzylic position as shown. Deprotection provides the representative HIV integrase inhibitor E of the present invention.

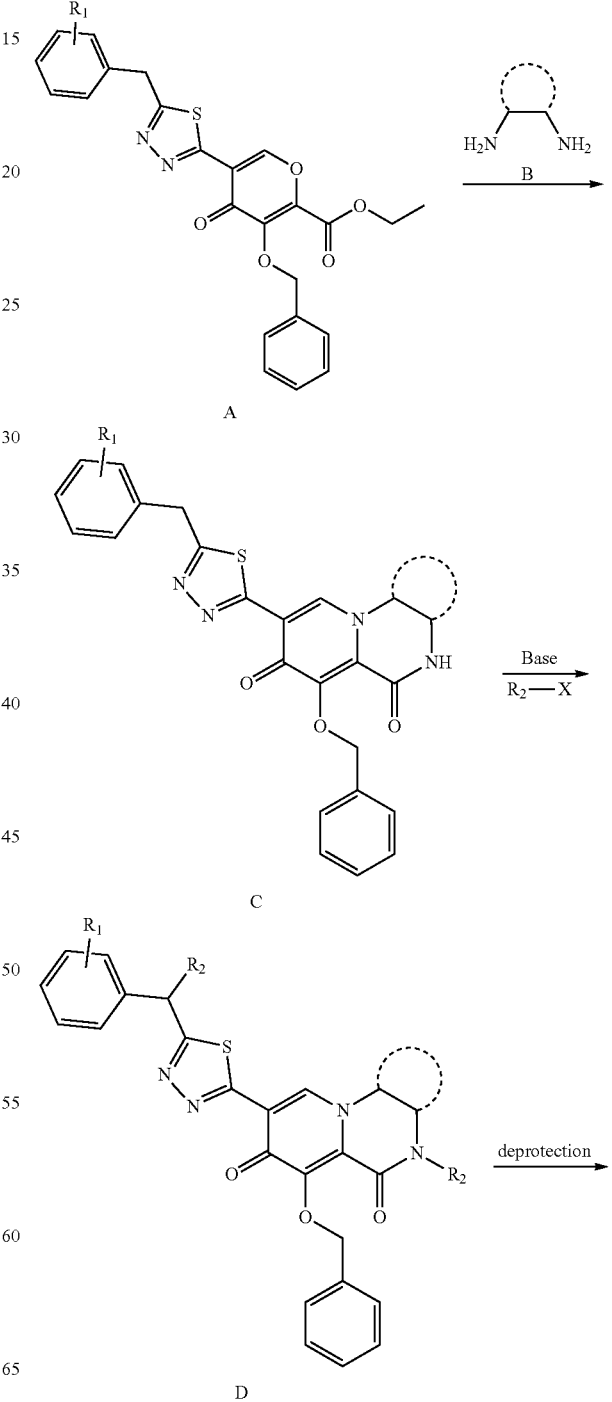

Scheme A

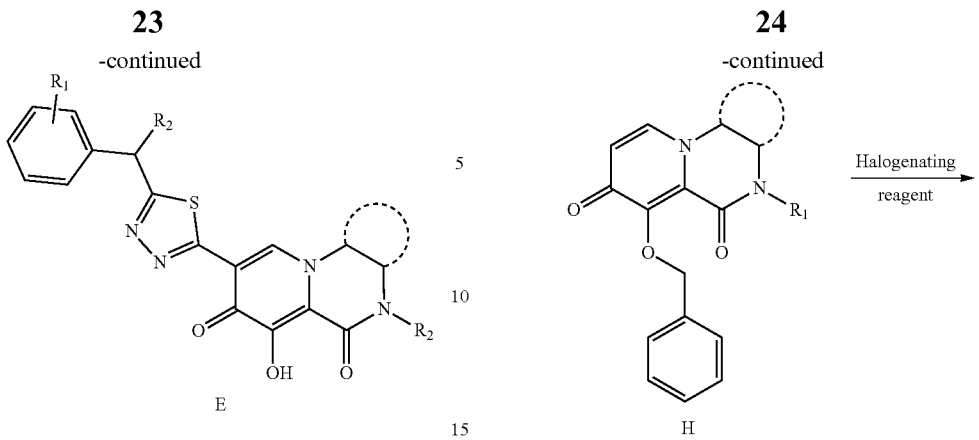

E

Scheme B depicts a general method for preparing compounds of the present invention wherein a cyclic diamine B is condensed into a pyranone F to provide the intermediate pyridinone which then cyclizes to form the lactam G. This cyclization to the lactam may require a coupling reagent such as BOP. The lactam is alkylated to form H and then selectively halogenated with a halogenating reagent such as NBS, NIS or bromine, to form J. Amidation under carbonylative conditions provides the amide K, which is then deprotected to provide representative HIV integrase inhibitor L of the present invention.

Halide J of Scheme B is a common intermediate. The enantiomers can be readily separated at this stage by preparative chiral SFC to provide single enantiomers that can be advanced in this and related chemistries.

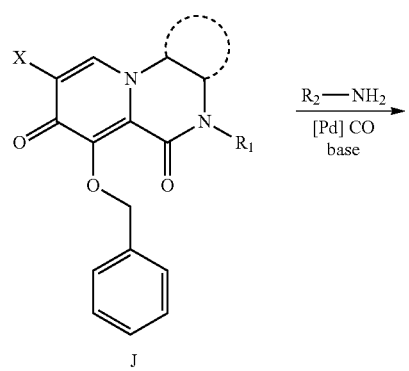

Scheme B

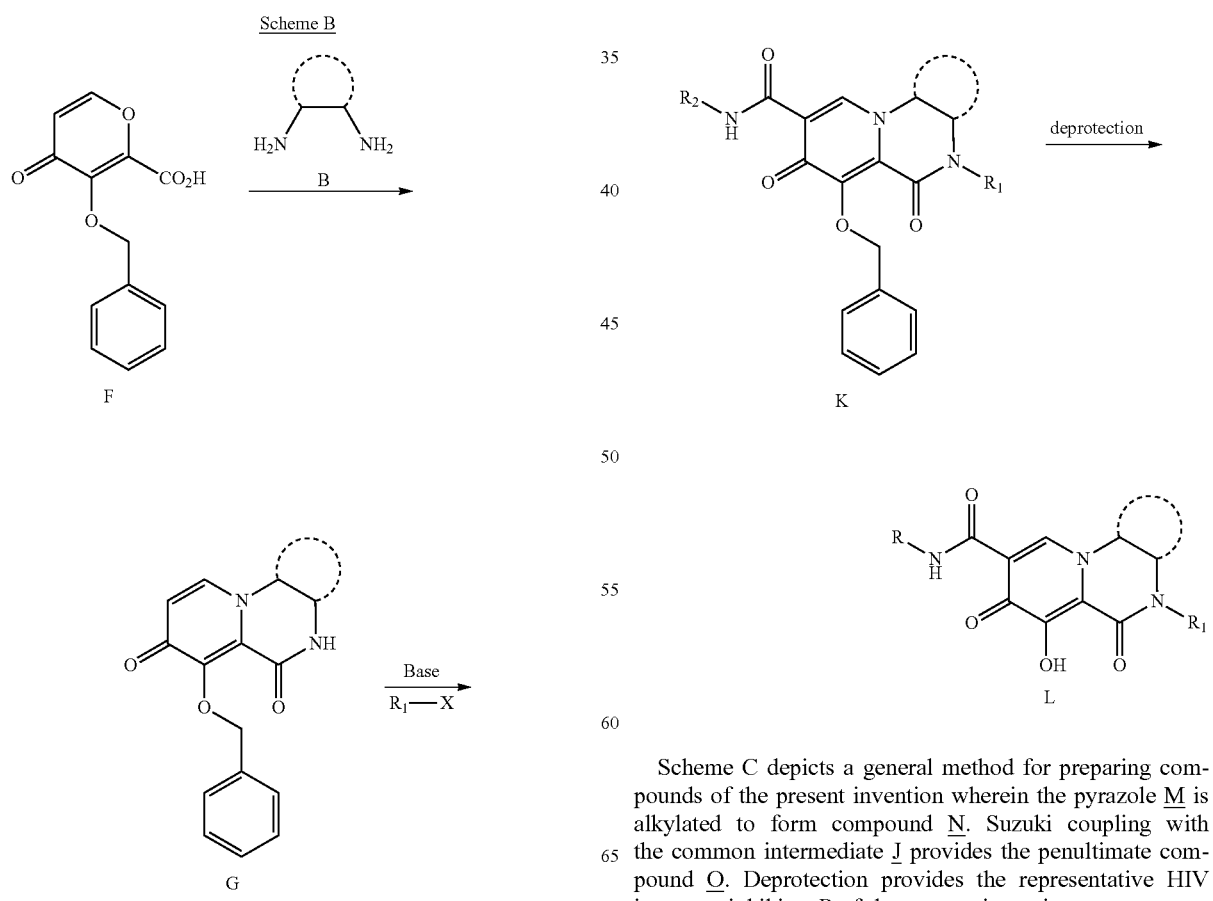

Scheme C depicts a general method for preparing compounds of the present invention wherein the pyrazole M is alkylated to form compound N. Suzuki coupling with the common intermediate J provides the penultimate compound O. Deprotection provides the representative HIV integrase inhibitor P of the present invention.

Scheme C

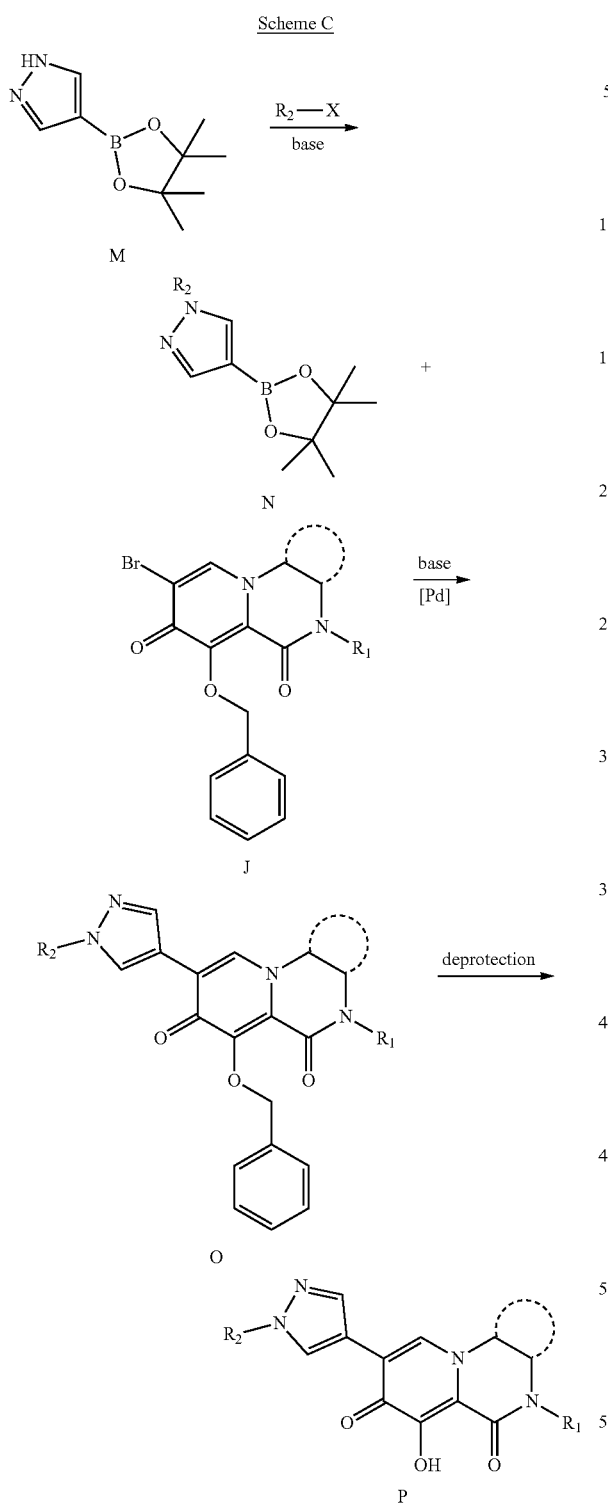

Scheme D

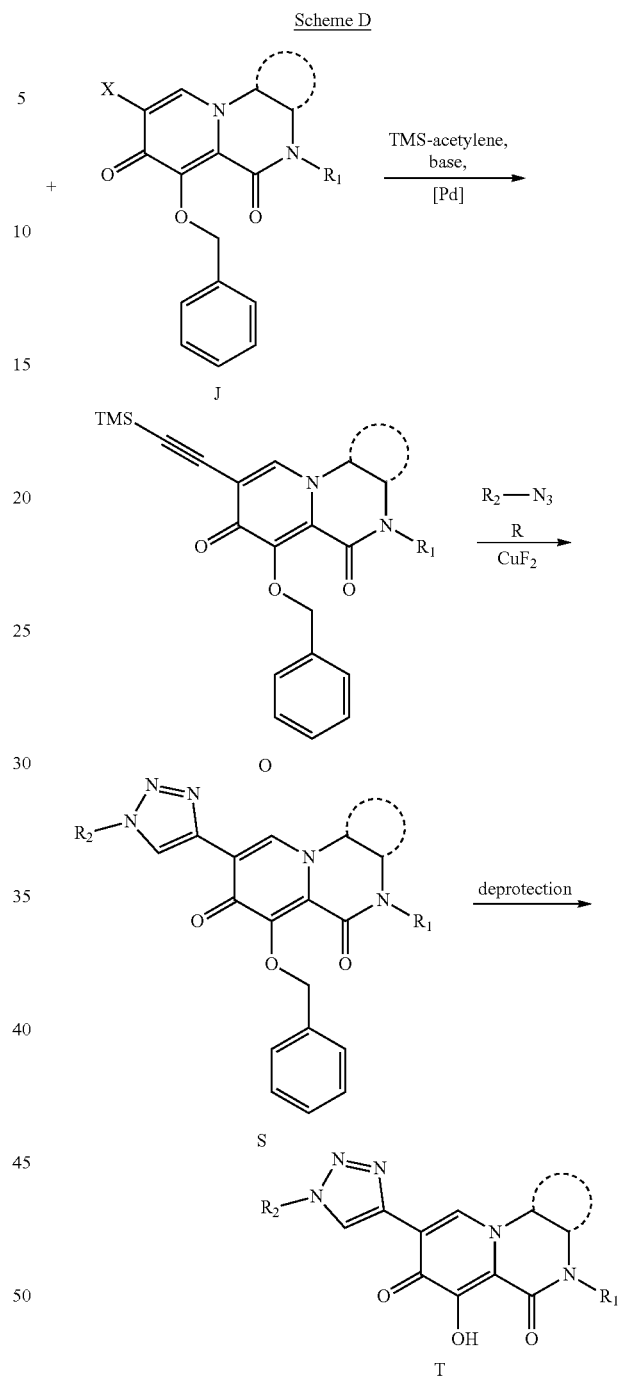

Scheme D depicts a general method for preparing compounds of the present invention wherein common intermediate J and TMS-acetylene react under Sonogashia coupling conditions to provide Q. Cycloaddition with azides of formula R provides the penultimate triazole S. Deprotection provides the representative HIV integrase inhibitor T of the present invention.

In the methods for preparing compounds of the present invention set forth in the foregoing schemes, functional groups in various moieties and substituents (in addition to those already explicitly noted in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in*

Organic Chemistry, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. The protecting groups may be removed at a convenient subsequent stage using methods known in the art. Alternatively the interfering group can be introduced into the molecule subsequent to the reaction Step of concern.

One skilled in the art of organic synthesis will recognize that the synthesis of compounds with multiple reactive functional groups, such as —OH and NH$_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods can be found in Greene & Wuts, *Protecting Groups in Organic Synthesis*, John Wiley & Sons, 3$^{rd}$ edition (1999).

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

Compounds of formula E, L, P and T may be further elaborated using methods that would be well-known to those skilled in the art of organic synthesis or, for example, the methods described in the Examples below, to make the full scope of the Compounds of Formula (I).

The starting materials used and the intermediates prepared using the methods set forth in Schemes A-D may be isolated and purified if desired using conventional techniques, including but not limited to filtration, distillation, crystallization, chromatography and alike. Such materials can be characterized using conventional means, including physical constants and spectral data.

EXAMPLES

General Methods

The following examples serve only to illustrate the invention and its practice. The examples are not to be construed as limitations on the scope or spirit of the invention. In these examples, all temperatures are degrees Celsius unless otherwise noted, and "room temperature" refers to a temperature in a range of from about 20° C. to about 25° C. Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS).

Mass analysis was performed with electrospray ionization in positive ion detection mode. $^1$H NMR spectra were recorded on Varian or Bruker instruments at 400-500 MHz. Concentration of solutions was carried out on a rotary evaporator under reduced pressure or by lyophilization. Flash chromatography was performed on pre-packed silica gel columns using a commercial MPLC system. Compounds described herein were synthesized as racemic mixtures unless otherwise stated in the experimental procedures.

Example 1

Preparation of Intermediate Compound Int-1

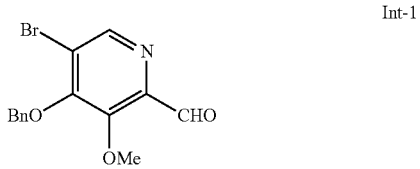 [SMILES: COc1c(C=O)ncc(Br)c1OCc1ccccc1]

Compound Int-1 was prepared using the method described in U.S. Patent Publication No. US2006/066414.

Example 2

Preparation of Compound Int-2f

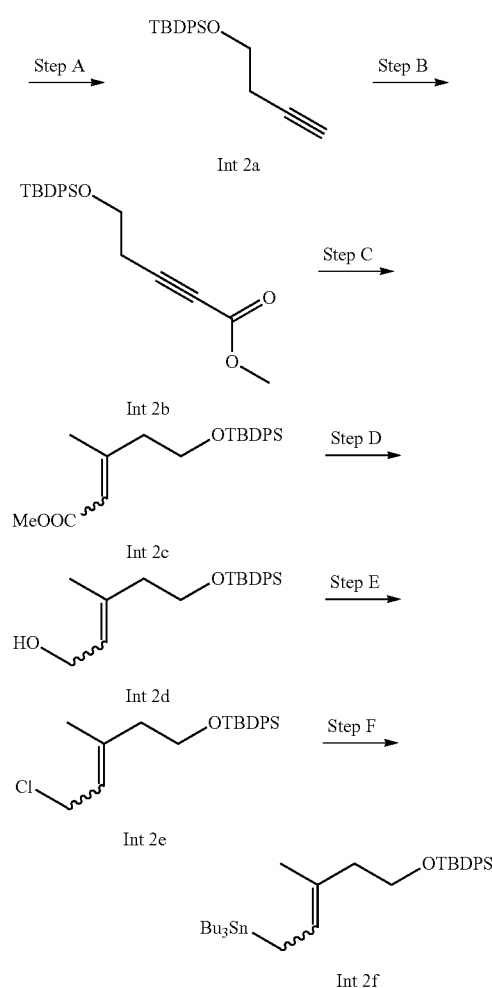

Step A—Synthesis of Compound Int-2a

To a solution of but-3-yn-1-ol (10 g, 143 mmol) in 110 mL of dichloromethane was added tert-butylchlorodiphenylsilane (37.3 g, 136 mmol) followed by 1H-imidazole (14.6 g, 214 mmol) and N,N-dimethylpyridin-4-amine (17.4 g, 143 mmol). The reaction was allowed to stir at 20° C. for 2 hours. The progress of the reaction was monitored by TLC. It was diluted with 150 mL of water, extracted using 50% EtOAc/hexanes (2×150 mL). The organic phase was concentrated in vacuo and the residue obtained was purified using a silica gel column chromatography (PET:EtOAc=200:1) to provide compound Int-2a as an oil. $^1$H NMR (400 MHz, CDCl$_3$): δ 7.68 (d, J=6.4 Hz, 4 H), 7.34-7.48 (m, 6H), 3.79 (t, J=7.0 Hz, 2H), 2.45 (dt, J=7.0, 2.4 Hz, 2H), 1.95 (brs, 1H), 1.06 (s, 9H).

Step B—Synthesis of Compound Int-2b

A stirred solution of compound Int-2a (13.4 g, 43.4 mmol) in 200 mL of THF at −78° C. was added butyllithium (18.24 ml, 45.6 mmol) was allowed to stir for 20 minutes at this temperature. To the resulting solution was added a solution of methyl carbonochloridate (5.336 g, 56.5 mmol) in 20 mL of THF via cannula, and the reaction was allowed to stir for 2 hours while warming up to 0° C. The reaction was quenched by addition of saturated NH$_4$Cl solution (100 mL) and extracted with EtOAc (2×200 mL). The organic layer was dried over anhydrous Na$_2$SO$_4$. The solvent was filtered and the filtrate was concentrated in vacuo to provide compound Int-2b as an oil. $^1$H NMR (400 MHz, CDCl$_3$): δ 7.67 (d, J=6.4 Hz, 4H), 7.33-7.50 (m, 6H), 3.81 (t, J=6.8 Hz, 2H), 3.76 (s, 3H), 2.58 (t, J=6.8 Hz, 2H), 1.05 (s, 9H).

Step C—Synthesis of Compound Int-2c

To a stirred solution of copper(I) iodide (13.8 g, 72.6 mmol) in THF (10 mL) at 0° C. was added methyllithium (29.7 ml, 47.5 mmol) and stirred for 15 min at 0° C. The resulting solution was cooled to −78° C. and a solution of compound Int-2b (17.4 mg, 47.5 mmol) in THF (5 mL) was added via cannula and stirred for 2 hours at that temperature. The reaction mixture was then quenched by the addition of saturated NH$_4$Cl (10 mL) followed by water (200 mL). The mixture was extracted with EtOAc (3×20 mL), the combined organic layer was dried over anhydrous Na$_2$SO$_4$, then filtered. The filtrate was concentrated in vacuo to provide compound Int-2c as an oil. $^1$H NMR (400 MHz, CDCl$_3$): δ 7.66 (d, J=6.4 Hz, 4H), 7.35-7.42 (m, 6H), 5.72 (s, 1H), 3.83 (t, J=6.4 Hz, 2H), 3.62-3.70 (m, 3H), 2.91 (t, J=6.4 Hz, 2H), 1.92 (s, 3H), 1.03 (s, 9H).

Step D—Synthesis of Compound Int-2d

To a solution of compound Int-2c (19 g, 49.7 mmol) in dichloromethane (200 mL) cooled to −78° C. was added diisopropylaluminum hydride (109 ml, 109 mmol). The reaction was allowed to stir at −78° C. for 1 hour and warm up to 0° C. At this time, it was quenched by adding 500 mL of saturated Rochelle salt solution. The mixture was allowed to stir at 0° C. for 1 hour and the organic phase was isolated, washed with 50 mL of brine and dried over Na$_2$SO$_4$, then it was filtered and the filtrate was concentrated in vacuo. The residue obtained was purified using silica gel column chromatography (PET:EtOAc=10:1) to provide compound Int-2d as an oil. $^1$H NMR (400 MHz, CDCl$_3$): δ 7.67 (d, J=6.4 Hz, 4H), 7.36-7.44 (m, 6H), 5.64 (t, J=6.8 Hz, 1H), 4.04 (d, J=6.8 Hz, 2H), 3.67 (t, J=6.4 Hz, 2H), 2.36 (t, J=6.4 Hz, 2H), 1.69 (s, 3H), 1.04 (s, 9H).

Step E—Synthesis of Compound Int-2e

To a solution of compound Int-2d (7 g, 19.74 mmol) and lithium chloride (1.7 g, 39.5 mmol) in dichloromethane (70 mL) was added N-ethyl-N-isopropylpropan-2-amine (6.4 g, 49.4 mmol) followed by methanesulfonyl chloride (3619 mg, 31.6 mmol). The reaction mixture was allowed to stir at 20° C. for 2 hours. Then it was diluted with 200 mL of dichloromethane and washed with 200 mL of 0.2 N HCl aqueous solution and 100 mL of brine. The organic phase was concentrated in vacuo to provide compound Int-2e as an oil. $^1$H NMR (400 MHz, CDCl$_3$): δ 7.66 (d, J=6.4 Hz, 4H), 7.36-7.46 (m, 6H), 5.50 (t, J=7.6 Hz, 1H), 3.96-4.14 (m, 2H), 3.64-3.80 (m, 2H), 2.35 (t, J=6.8 Hz, 2H), 1.63-1.77 (m, 3H), 1.04 (s, 9H).

Step F—Synthesis of Compound Int-2f

To a solution of lithium diethylamide (19.17 mL, 38.3 mmol) in THF (70 mL) cooled to 0° C., was added tributylstannane (10 g, 34.9 mmol). The reaction was allowed to stir at 0° C. for 30 minutes. It was then cooled to −78° C., and a solution of compound Int-2e (6.5 g, 17.43 mmol) in 30 mL of THF was added via syringe. The reaction was allowed to stir at −78° C. for 30 minutes. It was diluted with 100 mL of 20% EtOAc/hexanes and washed with 100 mL of water. The organic phase was isolated and the aqueous phase was extracted with 100 mL of 20% EtOAc/hexanes. The combined organics were washed with water, brine and concentrated under reduce pressure. The residue obtained was purified using a silica gel column chromatography (PET:EtOAc=100:1) to provide compound Int-2f as an oil. $^1$H NMR (400 MHz, CDCl$_3$): δ 7.63-7.75 (m, 4H), 7.32-7.45 (m, 6H), 5.30 (t, J=8.8 Hz, 1H), 3.66 (t, J=7.6 Hz, 2H), 2.18-2.33 (m, 2H), 1.54-1.63 (m, 5H), 1.39-1.50 (m, 6H), 1.21-1.33 (m, 6H), 1.03-1.08 (m, 9H), 0.74-0.92 (m, 15H). MS (M+H)+: 628.

Example 3

Preparation of Compounds 1-4

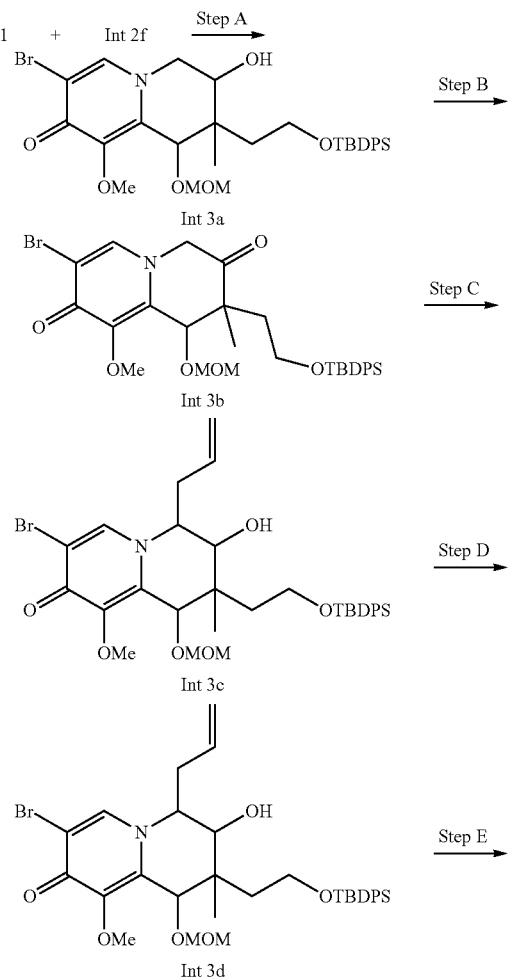

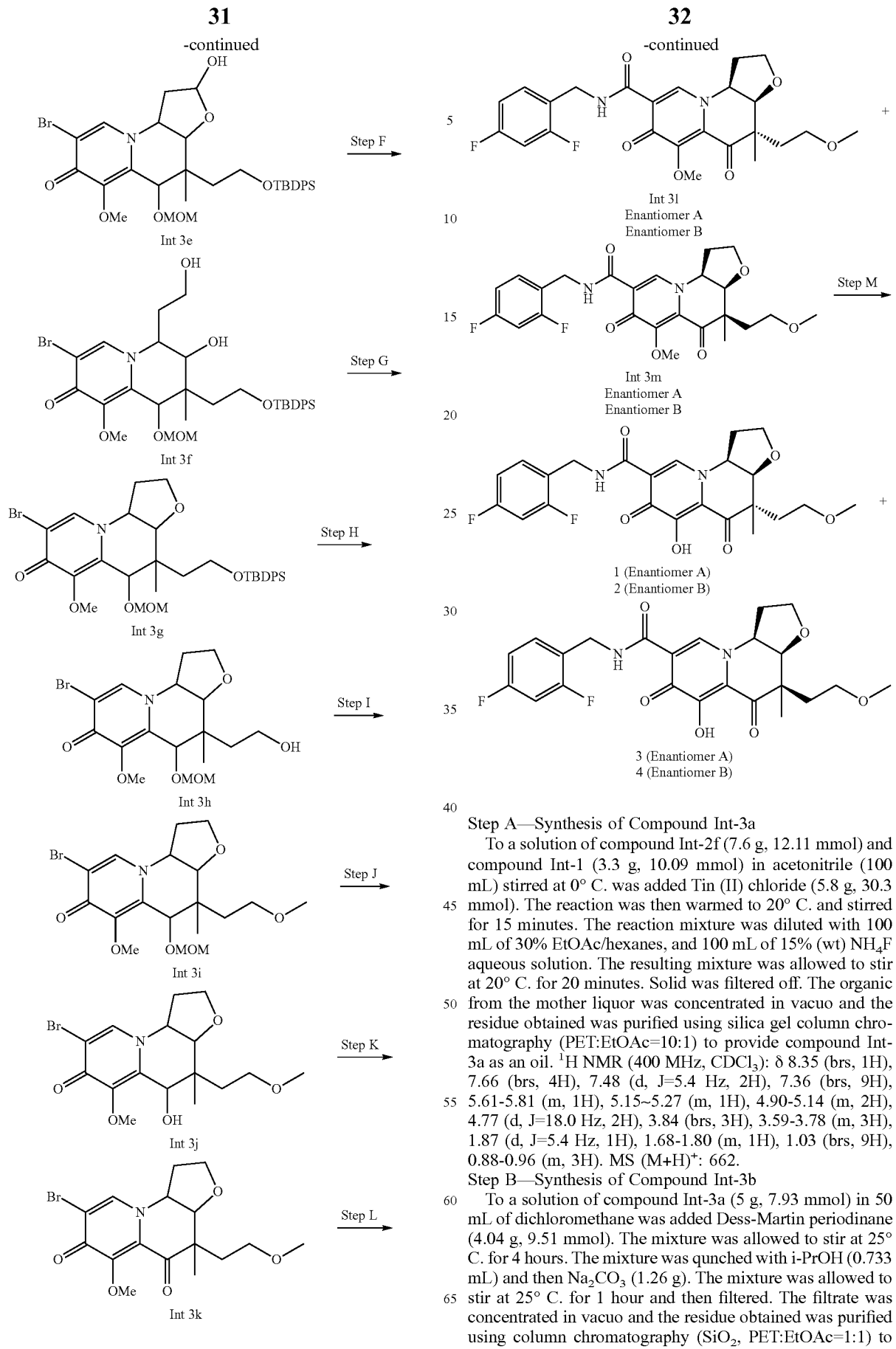

Step A—Synthesis of Compound Int-3a

To a solution of compound Int-2f (7.6 g, 12.11 mmol) and compound Int-1 (3.3 g, 10.09 mmol) in acetonitrile (100 mL) stirred at 0° C. was added Tin (II) chloride (5.8 g, 30.3 mmol). The reaction was then warmed to 20° C. and stirred for 15 minutes. The reaction mixture was diluted with 100 mL of 30% EtOAc/hexanes, and 100 mL of 15% (wt) NH$_4$F aqueous solution. The resulting mixture was allowed to stir at 20° C. for 20 minutes. Solid was filtered off. The organic from the mother liquor was concentrated in vacuo and the residue obtained was purified using silica gel column chromatography (PET:EtOAc=10:1) to provide compound Int-3a as an oil. $^1$H NMR (400 MHz, CDCl$_3$): δ 8.35 (brs, 1H), 7.66 (brs, 4H), 7.48 (d, J=5.4 Hz, 2H), 7.36 (brs, 9H), 5.61-5.81 (m, 1H), 5.15~5.27 (m, 1H), 4.90-5.14 (m, 2H), 4.77 (d, J=18.0 Hz, 2H), 3.84 (brs, 3H), 3.59-3.78 (m, 3H), 1.87 (d, J=5.4 Hz, 1H), 1.68-1.80 (m, 1H), 1.03 (brs, 9H), 0.88-0.96 (m, 3H). MS (M+H)$^+$: 662.

Step B—Synthesis of Compound Int-3b

To a solution of compound Int-3a (5 g, 7.93 mmol) in 50 mL of dichloromethane was added Dess-Martin periodinane (4.04 g, 9.51 mmol). The mixture was allowed to stir at 25° C. for 4 hours. The mixture was qunched with i-PrOH (0.733 mL) and then Na$_2$CO$_3$ (1.26 g). The mixture was allowed to stir at 25° C. for 1 hour and then filtered. The filtrate was concentrated in vacuo and the residue obtained was purified using column chromatography (SiO$_2$, PET:EtOAc=1:1) to provide compound Int-3b as an oil. $^1$H NMR (400 MHz, CDCl$_3$): δ 7.70~7.62 (m, 4H), 7.50 (d, J=5.2 Hz, 1H), 7.43~7.35 (m, 6H), 4.71~4.44 (m, 4H), 4.00 (s, 3H), 3.92~3.78 (m, 2H), 3.71~3.55 (m, 1H), 3.19 (s, 3H), 2.19~2.06 (m, 2H), 1.06~0.93 (m, 12H). MS (+ESI) m/z: 630.1.

Step C—Synthesis of Compound Int-3c

To a solution of compound Int-3b (1000 mg, 1.6 mmol) and 3-iodoprop-1-ene (1068 mg, 6.36 mmol) in 15 mL of THF was allowed to stir at 20° C. for 5 min under N$_2$, then cooled to −78° C. Hexamethylphosphoramide (7.5 mL) was added, and then 1 M LiHMDS in THF (2.06 mL, 2.06 mmol) under N$_2$. The reaction was allowed to stir at this temperature for 30 minutes. It was quenched by adding 10 mL of saturated NH$_4$Cl aqueous solution at −78° C. After warmed to room temperature, the mixture washed with 50 mL of H$_2$O and then extracted using EtOAc (20 mL×3). The organic phase was washed with 50 mL of brine, dried with Na$_2$SO$_4$, and then concentrated in vacuo. The residue obtained was purified using a prep-TLC (SiO$_2$, PET:EtOAc=1:1) to provide compound Int-3c as a film. $^1$H NMR (400 MHz, CDCl$_3$): δ 7.67~7.75 (m, 3H), 7.37~7.55 (m, 8H), 5.77~5.81 (m, 1H), 5.01~5.41 (m, 3H), 4.55~4.70 (m, 2H), 4.11~4.38 (m, 2H), 4.01 (s, 3H), 3.50~3.95 (m, 2H), 3.24 (s, 3H), 2.50~2.80 (m, 2H), 2.00~2.25 (m, 1H), 1.02 (s, 9H), 0.97 (s, 3H). MS (+ESI) m/z: 670.2.

Step D—Synthesis of Compound Int-3d

To a solution of compound Int-3c (600 mg, 0.897 mmol) in 10 mL of MeOH cooled to 0° C. was added NaBH$_4$ (68 mg, 1.79 mmol). The reaction was allowed to stir at 20° C. for 3 hours. TLC showed the disappearance of the starting material. At this time, it was quenched by adding 20 mL of water at 0° C. and neutralized to pH=5~6 with diluted HCl, The mixture was extracted with dichloromethane (20 mL×3). The organic phase was then concentrated in vacuo to provide compound Int-3d as a solid. It was used for the next step without further purification. $^1$H NMR (400 MHz, CDCl$_3$): δ 7.86 (s, 1H), 7.67 (d, J=7.04 Hz, 3H), 7.56 (t, J=6.46 Hz, 1H), 7.30~7.48 (m, 6H), 5.76~5.93 (m, 1H), 5.11~5.28 (m, 2H), 4.90 (s, 1H), 4.70~4.82 (m, 1H), 4.43~4.56 (m, 1H), 4.31 (d, J=9.78 Hz, 1H), 4.01~4.13 (m, 1H), 3.80~3.96 (m, 5H), 3.34 (s, 3H), 2.92~2.97 (m, 1H), 2.79~2.82 (m, 1H), 2.40~2.43 (m, 1H), 1.79~1.86 (m, 1H), 1.04 (s, 9H), 0.99 (s, 3H). MS (+ESI) m/z: 670.3.

Step E—Synthesis of Compound Int-3e

To a solution of compound Int-3d (480 mg, 0.716 mmol) in THF (10 mL) and Water (10.00 mL) were added osmium tetroxide in H$_2$O (18 mg, 0.071 mmol) and sodium periodate (306 mg, 1.43 mmol). The mixture was allowed to stir at 25° C. for 1 hour. The reaction was monitored by TLC. At completion, the reaction was added 20 mL of saturated aqueous Na$_2$SO$_3$ solution and stirred for 30 minutes. The mixture was extracted with dichloromethane (10 mL×3). The combined organic phase was dried over anhydrous Na$_2$SO$_4$. The solvent was removed in vacuo to provide compound Int-3e as a solid. It was used in the next reaction without further purification. $^1$H NMR (400 MHz, CDCl$_3$): δ 7.61~7.69 (m, 3H), 7.58~7.59 (m, 2H), 7.38~7.44 (m, 6H), 5.50~5.55 (m, 1H), 4.44~4.92 (m, 6H), 3.96 (s, 3H), 3.90~3.95 (m, 1H), 3.36 (s, 3H), 2.29~2.47 (m, 3H), 1.90~2.00 (m, 1H), 1.01~1.06 (m, 12H). MS (+ESI) m/z: 674.2.

Step F—Synthesis of Compound Int-3f

To a solution of compound Int-3e (400 mg, 0.594 mmol) in 10 mL of MeOH cooled to 0° C. was added NaBH$_4$ (90 mg, 2.38 mmol). The reaction was allowed to stir at 20° C. for 3 hours. At this time, it was quenched by adding 20 mL of water at 0° C. and neutralized to pH=5~6 with diluted HCl. The mixture was extracted with dichloromethane (20 mL×3). The organic phase was then concentrated in vacuo to provide compound Int-3f as a solid, which was used without further purification. $^1$H NMR (400 MHz, CDCl$_3$): δ 7.61~7.69 (m, 3H), 7.58~7.59 (m, 2H), 7.38~7.44 (m, 6H), 4.74~4.98 (m, 2H), 4.35~4.62 (m, 2H), 4.03~4.12 (m, 1H), 3.67~4.01 (m, 5H), 3.36 (s, 3H), 2.40-2.66 (m, 2H), 2.28 (d, J=13.11 Hz, 1H), 2.17 (s, 3H), 1.80 (d, J=14.09 Hz, 1H), 1.06 (s, 9H), 1.02 (s, 3H).

Step G—Synthesis of Compound Int-3g

The solution of compound Int-3f (330 mg, 0.489 mmol) in 10 mL of dichloromethane was added Et$_3$N (0.707 mL, 4.89 mmol) and methanesulfonyl chloride (0.19 mL, 2.45 mmol) at 0° C. The reaction was allowed to stir at 20° C. for 16 hours. 30 mL of water was then added. The resulting mixture was extracted using dichloromethane (3×10 mL). The combined organic phase was washed with 20 mL of brine and dried over anhydrous Na$_2$SO$_4$. It was then concentrated in vacuo and the residue obtained was purified using a prep-TLC plate (SiO$_2$, dichloromethane:EtOAc=1:1) to provide compound Int-3g as an oil. $^1$H NMR (400 MHz, CDCl$_3$): δ 7.61~7.69 (m, 3H), 7.58~7.59 (m, 2H), 7.38~7.44 (m, 6H), 4.88 (s, 1H), 4.56~4.75 (m, 2H), 4.40~4.50 (m, 2H), 4.01~4.23 (m, 2H), 3.96 (s, 3H), 3.26~3.42 (m, 3H), 3.15 (s, 3H), 2.13~2.64 (m, 2H), 1.87~2.07 (m, 1H), 1.05 (s, 9H), 1.01 (s, 3H). MS (+ESI) m/z: 658.1.

Step H—Synthesis of Compound Int-3h

To a solution of compound Int-3g (275 mg, 0.418 mmol) in 5 mL of THF was added 1 M tetrabutylammonium fluoride in THF (0.626 ml, 0.626 mmol). The mixture was allowed to stir at 20° C. for 16 hours. The mixture was then concentrated in vacuo and the residue obtained was purified using a prep-TLC plate (SiO$_2$, dichloromethane:MeOH=10:1) to provide compound Int-3h as an oil. $^1$H NMR (400 MHz, CDCl$_3$): δ 7.75 (s, 1H), 4.69~4.89 (m, 3H), 4.47~4.49 (m, 1H), 4.11~4.13 (m, 2H), 3.97 (s, 3H), 3.50~3.80 (m, 2H), 3.40 (s, 3H), 2.51~2.60 (m, 1H), 2.20~2.35 (m, 2H), 1.63~1.86 (m, 2H), 1.34 (s, 3H). MS (+ESI) m/z: 418.1.

Step I—Synthesis of Compound Int-3i

To solution of compound Int-3h (160 mg, 0.4 mmol) in 3 mL of DMF stirred at 20° C., was added NaH (46 mg, 1.148 mmol) followed by iodomethane (0.12 mL, 1.912 mmol). The resulting reaction was allowed to stir at 20° C. for 3 hours, then was quenched with 2 drops of saturated aqueous NH$_4$Cl solution, and the mixture was diluted with 5 mL of H$_2$O. It was extracted with dichloromethane (5 mL×4). The combined organic phase was concentrated in vacuo and purified using a prep-TLC plate (SiO$_2$, dichloromethane: EtOAc=1:1) to provide compound Int-3i as an oil. MS (+ESI) m/z: 434.0.

Step J—Synthesis of Compound Int-3j

To a stirred solution of compound Int-3i (120 mg, 0.28 mmol) in 5 mL of MeOH was added p-toluenesulfonic acid monohydrate (264 mg, 1.4 mmol). The reaction mixture was allowed to stir at 35° C. for 16 hours, then concentrated in vacuo. To the residue obtained was added 10 mL of saturated aqueous NaHCO$_3$ solution. The resulting mixture was then extracted with dichloromethane (10 mL×4). The organic phase was concentrated in vacuo, and the residue obtained was purified using a prep-TLC plate (SiO$_2$, dichloromethane:EtOAc=1:2) to provide compound Int-3j as an oil. $^1$H NMR (400 MHz, CDCl$_3$): δ 7.70~7.71 (m, 1H), 4.45~4.86 (m, 3H), 3.98 (s, 3H), 3.35~3.60 (m, 4H), 3.32 (s, 3H), 2.51~2.60 (m, 1H), 2.09~2.25 (m, 2H), 1.63~1.78 (m, 1H), 1.31 (s, 3H). MS (+ESI) m/z: 390.1.

Step K—Synthesis of Compound Int-3k

To a stirred solution of compound Int-3j (100 mg, 0.26 mmol) in 6 mL of 1,2-dichloroethane was added Dess Martin periodinane (218 mg, 0.52 mmol). The reaction mixture was allowed to stir at 20° C. for 8 hours. The reaction mixture was then diluted with 10 mL of EtOAc and filtered. The filtrate was concentrated in vacuo and the residue obtained was purified using a prep-TLC plate ($SiO_2$, dichloromethane:EtOAc=1:1) to provide compound Int-3k as a solid. $^1$H NMR (400 MHz, $CDCl_3$): δ 7.71~7.73 (m, 1H), 4.77~4.86 (m, 1H), 4.17~4.33 (m, 1H), 3.99 (s, 3H), 3.84~3.89 (m, 2H), 3.35~3.60 (m, 2H), 3.32 (s, 3H), 2.51~2.60 (m, 1H), 2.09~2.25 (m, 2H), 1.63~1.78 (m, 1H), 1.33 (s, 3H). MS (+ESI) m/z: 388.0.

Step L—Synthesis of Compound Int-3l and Compound Int-3m

To a mixture of compound Int-3k (59.3 mg, 0.414 mmol) in 3 mL of DMSO was added $Pd(Ph_3P)_4$ (120 mg, 0.104 mmol) under $N_2$. The mixture was allowed to stir at 80° C. for 4 hours under a balloon of CO. The reaction mixture was then diluted with 20 mL of EtOAc and filtered. The filtrate was washed with diluted HCl (20 mL) and the aqueous phase was back extracted with EtOAc (10 mL×3). The combined organic phases were washed with 20 mL of brine, dried over anhydrous $Na_2SO_4$. The solvent was removed in vacuo and the residue obtained was purified using a prep-TLC plate ($SiO_2$, EtOAc:$CH_2Cl_2$=1:1) to provide a mixture of four diastereomers of N-(2,4-difluorobenzyl)-6-methoxy-4-(2-methoxyethyl)-4-methyl-5,7-dioxo-2,3a,4,5,7,10a-hexahydro-1H-furo[2,3-c]quinolizine-8-carboxamide as a solid. MS (+ESI) m/z: 477.2. This mixture was further purified using running consecutively SFC (Column: AD (250 mm×30 mm, 10 um), Mobile phase: A: Supercritical $CO_2$, B: MeOH (contained 0.1% $NH_3H_2O$), A:B=65:35, Flow rate: 80 mL/minutes Wavelength: 220 nm) and SFC (Column: OJ (250 mm×30 mm, 5 um), Mobile phase: A: Supercritical $CO_2$, B: MeOH (contained 0.1% $NH_3H_2O$), A:B=60:40, Flow rate: 60 mL/minutes Wavelength: 220 nm) to give sequentially enantiomer A of compound Int-3l, enantiomer B of compound Int-3l, enantiomer A of compound Int-3m and enantiomer B of compound Int-3m as an oil.

Enantiomer A of compound Int-3l: $^1$H NMR (400 MHz, $CDCl_3$): δ 10.47 (brs, 1H), 8.45 (s, 1H), 7.34~7.40 (m, 1H), 6.77~6.85 (m, 2H), 4.93~4.95 (m, 1H), 4.60~4.65 (m, 2H), 4.17 (d, J=4.8 Hz, 1H), 4.00 (s, 3H), 3.82~3.85 (m, 2H), 3.20~3.40 (m, 2H), 3.18 (s, 3H), 2.65~2.68 (m, 1H), 2.18~2.33 (m, 1H), 1.72~1.78 (m, 2H), 1.38 (s, 3H). MS (+ESI) m/z: 477.2.

Enantiomer B of compound Int-3l: $^1$H NMR (400 MHz, $CDCl_3$): δ 10.47 (brs, 1H), 8.45 (s, 1H), 7.34~7.40 (m, 1H), 6.77~6.85 (m, 2H), 4.93~4.95 (m, 1H), 4.60~4.65 (m, 2H), 4.17 (d, J=4.8 Hz, 1H), 4.00 (s, 3H), 3.82~3.85 (m, 2H), 3.20~3.40 (m, 2H), 3.18 (s, 3H), 2.65~2.68 (m, 1H), 2.18~2.33 (m, 1H), 1.72~1.78 (m, 2H), 1.38 (s, 3H). MS (+ESI) m/z: 477.2.

Enantiomer A of compound Int-3m: $^1$H NMR (400 MHz, $CDCl_3$): δ 10.42 (brs, 1H), 8.47 (s, 1H), 7.34~7.40 (m, 1H), 6.77~6.85 (m, 2H), 4.84 (s, 1H), 4.60~4.65 (m, 2H), 4.33 (d, J=4.8 Hz, 1H), 4.00 (s, 3H), 3.83~3.87 (m, 2H), 3.58~3.62 (m, 2H), 3.32 (s, 3H), 2.65~2.71 (m, 1H), 2.04~2.29 (m, 3H), 1.22 (s, 3H). MS (+ESI) m/z: 477.2.

Enantiomer B of compound Int-3m: $^1$H NMR (400 MHz, $CDCl_3$): δ 10.42 (brs, 1H), 8.47 (s, 1H), 7.34~7.40 (m, 1H), 6.77~6.85 (m, 2H), 4.84 (s, 1H), 4.60~4.65 (m, 2H), 4.33 (d, J=4.8 Hz, 1H), 4.00 (s, 3H), 3.83~3.87 (m, 2H), 3.58~3.62 (m, 2H), 3.32 (s, 3H), 2.65~2.71 (m, 1H), 2.04~2.29 (m, 3H), 1.22 (s, 3H). MS (+ESI) m/z: 477.2.

Step M—Synthesis of Compounds 1-4

A solution of enantiomer A of compound Int-3l (8 mg, 0.017 mmol) and lithium chloride (14.24 mg, 0.336 mmol) in 4 mL of DMF was allowed to stir at 80° C. for 8 hours. The crude reaction mixture was purified using prep-HPLC (Phenomenex Synergi C18 100×21.2 mm×4 um using TFA water and acetonitrile as the eluents, to provide compound 1 as a solid. Mobile phase A: water (containing 0.1% TFA), mobile phase B: acetonitrile. Gradient: 29%~59% B, 0~12 minutes. Flow Rate: 25 mL/min) $^1$H NMR (400 MHz, $CDCl_3$): δ 10.51 (brs, 1H), 8.55 (s, 1H), 7.33~7.39 (m, 1H), 6.79~6.85 (m, 2H), 5.01 (d, J=4.4 Hz, 1H), 4.65 (d, J=5.2 Hz, 2H), 4.20 (d, J=4.0 Hz, 1H), 3.79~3.90 (m, 2H), 3.45~3.50 (m, 1H), 3.33~3.38 (m, 1H), 3.16 (s, 3H), 2.71~2.73 (m, 1H), 2.31~2.33 (m, 1H), 1.78~1.80 (m, 2H), 1.45 (s, 3H). MS (+ESI) m/z: 463.2.

A solution of enantiomer B of compound Int-3l (8 mg, 0.017 mmol) and lithium chloride (14.24 mg, 0.336 mmol) in 4 mL of DMF was allowed to stir at 80° C. for 8 hours. The crude reaction mixture was purified using prep-HPLC (Phenomenex Synergi C18 250×21.2 mm×4 um using TFA water and acetonitrile as the eluents, to provide compound 2 as a solid. Mobile phase A: water (containing 0.1% TFA), mobile phase B: acetonitrile. Gradient: 28%~58% B, 0~11 minute. Flow Rate: 25 mL/min) $^1$H NMR (400 MHz, $CDCl_3$): δ 10.43 (brs, 1H), 8.55 (s, 1H), 7.33~7.39 (m, 1H), 6.79~6.85 (m, 2H), 5.01 (d, J=4.4 Hz, 1H), 4.65 (d, J=5.2 Hz, 2H), 4.20 (d, J=4.0 Hz, 1H), 3.79~3.90 (m, 2H), 3.45~3.50 (m, 1H), 3.33~3.38 (m, 1H), 3.16 (s, 3H), 2.71~2.73 (m, 1H), 2.31~2.33 (m, 1H), 1.78~1.80 (m, 2H), 1.45 (s, 3H). MS (+ESI) m/z: 463.2.

A solution of enantiomer A of compound Int-3m (15 mg, 0.03 mmol) and lithium chloride (27 mg, 0.63 mmol) in 4 mL of DMF was allowed to stir at 80° C. for 8 hours. The crude reaction mixture was purified using prep-HPLC (Phenomenex Synergi C18 100×21.2 mm×4 um using TFA water and acetonitrile as the eluents, to provide compound 3 as a solid. Mobile phase A: water (containing 0.1% TFA), mobile phase B: acetonitrile. Gradient: 35%~55% B, 0~12 minutes. Flow Rate: 25 mL/min). $^1$H NMR (400 MHz, $CDCl_3$): δ 10.43 (brs, 1H), 8.55 (s, 1H), 7.33~7.39 (m, 1H), 6.79~6.85 (m, 2H), 4.87~4.90 (m, 1H), 4.65 (d, J=5.2 Hz, 2H), 4.38 (d, J=4.0 Hz, 1H), 3.93~3.94 (m, 1H), 3.79~3.81 (m, 1H), 3.63~3.66 (m, 2H), 3.35 (s, 3H), 2.71~2.73 (m, 1H), 2.37~2.38 (m, 1H), 2.17~2.20 (m, 2H), 1.30 (s, 3H). MS (+ESI) m/z: 463.2.

A solution of enantiomer B of compound Int-3m (15 mg, 0.03 mmol) and lithium chloride (27 mg, 0.63 mmol) in 4 mL of DMF was allowed to stir at 80° C. for 8 hours. The crude reaction mixture was purified using prep-HPLC (Phenomenex Synergi C18 250×21.2 mm×4 um using TFA water and acetonitrile as the eluents, to provide compound 4 as a solid. Mobile phase A: water (containing 0.1% TFA), mobile phase B: acetonitrile. Gradient: 28%~58% B, 0~11 minute. Flow Rate: 25 mL/min) $^1$H NMR (400 MHz, $CDCl_3$): δ 10.40 (brs, 1H), 8.53 (s, 1H), 7.33~7.39 (m, 1H), 6.79~6.85 (m, 2H), 4.87~4.90 (m, 1H), 4.65 (d, J=5.2 Hz, 2H), 4.38 (d, J=4.0 Hz, 1H), 3.93~3.94 (m, 1H), 3.79~3.81 (m, 1H), 3.63~3.66 (m, 2H), 3.35 (s, 3H), 2.71~2.73 (m, 1H), 2.37~2.38 (m, 1H), 2.17~2.20 (m, 2H), 1.30 (s, 3H). MS (+ESI) m/z: 463.2.

Example 4
Preparation of Compound 5 and Compound 6
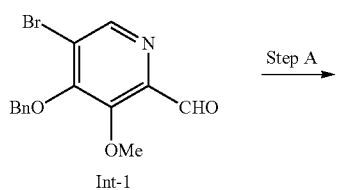
Int-1
Step A →
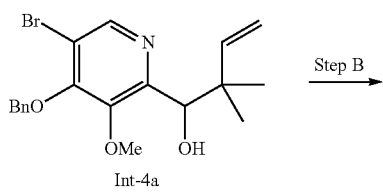
Int-4a
Step B →
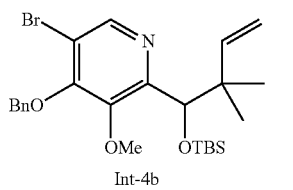
Int-4b
Step C →
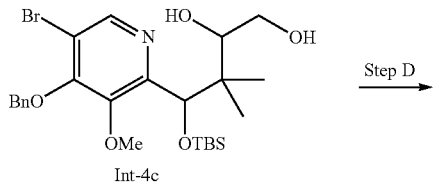
Int-4c
Step D →
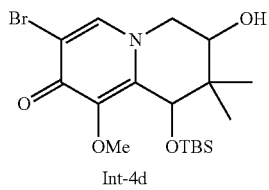
Int-4d
Step E →
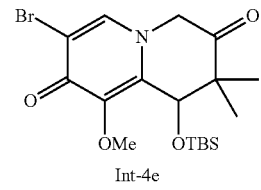
Int-4e
Step F →
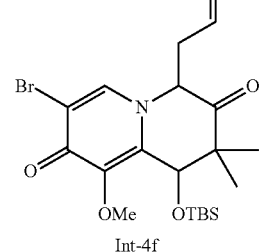
Int-4f
Step G →
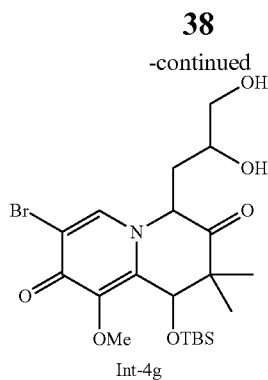
Int-4g
Step H →
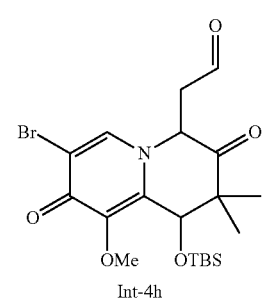
Int-4h
Step I →
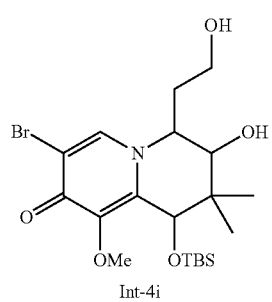
Int-4i
Step J →
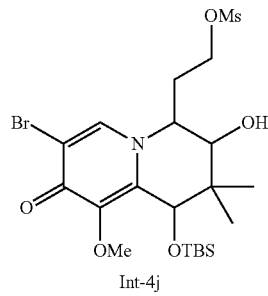
Int-4j
Step K →
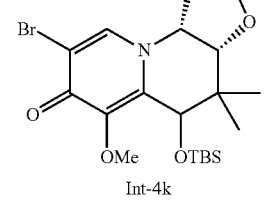
Int-4k
Step L →
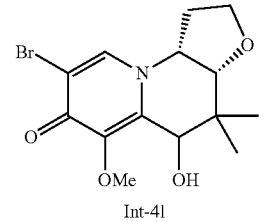
Int-4l
Step M →

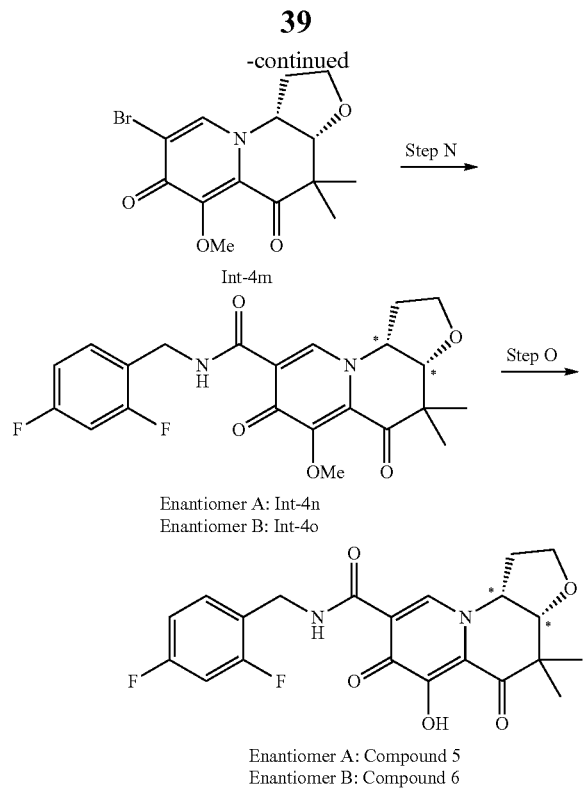

Enantiomer A: Int-4n
Enantiomer B: Int-4o

Enantiomer A: Compound 5
Enantiomer B: Compound 6

Step A—Synthesis of Compound Int-4a

To a solution of sodium iodide (6979 mg, 46.6 mmol), indium (13400 mg, 116 mmol) and 1-bromo-3-methylbut-2-ene (5204 mg, 34.9 mmol) in DMF (60 mL) was added compound Int-1 (7500 mg, 23.28 mmol). The mixture was allowed to stir at 25° C. for 2 hours. The reaction was diluted with 200 mL EtOAc. The organic phase was washed with water (200 mL), brine (200 mL) and then dried over anhydrous sodium sulfate. After filtration, the organic solvent was removed under vacuum and the resulting residue was purified using a silica gel column eluting with 14% EtOAc/petroleum ether to provide compound Int-4a as an oil. $^1$H NMR (400 MHz, CDCl$_3$): δ 8.34 (s, 1H), 7.41-7.50 (m, 2H), 7.31-7.38 (m, 3H), 5.85 (t, J=10.8 Hz, 1H), 5.22 (d, J=11.2 Hz, 1H), 5.10 (d, J=11.2 Hz, 1H), 4.99 (d, J=10.8 Hz, 1H), 4.91 (d, J=10.8 Hz, 1H), 4.61-4.72 (m, 1H), 3.87 (s, 3H), 1.03 (s, 3H), 1.01 s, 3H). MS: m/z=394.1 (M+1).

Step B—Synthesis of Compound Int-4b

To a solution of compound Int-4a (7500 mg, 19.12 mmol) in CH$_2$Cl$_2$ (120 mL) were added 2,6-lutidine (4.45 mL, 38.2 mmol), tert-butyldimethylsilyl 2-methylpropane-2-sulfonate (7240 mg, 28.7 mmol) at 0° C. After addition, the mixture was allowed to stir at 25° C. for 6 hours. It was quenched by addition of saturated NaHCO$_3$ solution (40 mL). The aqueous was extracted with CH$_2$Cl$_2$ (30 mL×2), dried over anhydrous sodium sulfate, filtered and concentrated in vacuo to provide the crude product, which was purified using a silica gel column eluting with 6% EtOAc/petroleum ether to provide compound Int-4b as an oil. $^1$H NMR (400 MHz, CDCl$_3$): δ 8.67 (s, 1H), 7.52-7.73 (m, 5H), 6.22-6.29 (m, 1H), 5.27-5.38 (m, 2H), 5.11-5.21 (m, 3H), 4.14 (s, 3H), 1.29 (s, 6H), 1.12 (s, 9H), 0.32 (s, 3H), 0.25 (s, 3H). MS: m/z=508.2 (M+1).

Step C—Synthesis of Compound Int-4c

To a solution of compound Int-4b (7500 mg, 14.81 mmol) in THF (80 mL), water (40 mL) was added osmium tetroxide (0.465 mL, 1.481 mmol), 4-methylmorpholine N-oxide (3469 mg, 29.6 mmol) and the mixture was allowed to stir at 25° C. for 6 hours. The reaction was quenched by adding saturated aqueous Na$_2$SO$_3$ (30 mL) and then stirred for another 30 minutes. The reaction mixture was extracted with EtOAc (50 mL×3), dried over anhydrous sodium sulfate, filtered and concentrated in vacuo to provide crude product, which was purified using a silica gel column eluting with 50% EtOAc/petroleum ether to provide compound Int-4c as an oil. $^1$H NMR (400 MHz, CDCl$_3$): δ 8.73-8.82 (m, 1H), 7.61-7.83 (m, 5H), 5.41-5.53 (m, 2H), 5.11-5.23 (m, 1H), 4.28 (d, J=4.0 Hz, 3H), 3.84-4.05 (m, 3H), 1.06-1.26 (m, 15H), 0.39-0.49 (m, 3H), 0.01-0.07 (m, 3H). MS: m/z=540.2 (M+1).

Step D—Synthesis of Compound Int-4d

To a solution of compound Int-4c (3800 mg, 7.03 mmol) in pyridine (55 mL) was added TsCl (2412 mg, 12.65 mmol). The mixture was allowed to stir at 30° C. for 16 hours. The reaction was quenched by addition of MeOH (25 mL) and the mixture was stirred for another 1 hour. The mixture was diluted with EtOAc (500 mL), washed with aqueous HCl solution (1.0 M, 500 mL), brine (100 mL). The organic phase was dried over anhydrous sodium sulfate, filtered and the filtrate was concentrated under vacuum. The resulting residue was purified using a silica gel column eluting 5% methanol/CH$_2$Cl$_2$ to provide compound Int-4d as a solid. $^1$H NMR (400 MHz, chloroform-d): δ 7.81 (s, 1H), 4.48-4.59 (m, 1H), 4.22-4.35 (m, 2H), 3.98 (s, 3H), 3.66-3.76 (m, 1H), 1.25-1.35 (m, 3H), 0.76-0.95 (m, 12H), 0.01-0.26 (m, 6H). MS: m/z=434.2 (M+1).

Step E—Synthesis of Compound Int-4e

To a stirred solution of compound Int-4d (1 g, 3.313 mmol) in CH$_2$Cl$_2$ (10 mL) was added Dess Martin periodinane (1.471 g, 3.47 mmol). The reaction mixture was allowed to stir at 20° C. for 2 hours. The reaction mixture was diluted with 5 drops water and the solid was filtered off. The filtrate was concentrated in vacuo and the resulting residue was purified using a silica gel column eluting with 33% EtOAc/CH$_2$Cl$_2$ to provide compound Int-4e as a solid. $^1$H NMR (400 MHz, CDCl$_3$): δ 7.65 (s, 1H), 5.01 (s, 1H), 4.68 (d, J=17.6 Hz, 1H), 4.30 (d, J=18.1 Hz, 1H), 4.05 (s, 3H), 1.33 (s, 3H), 0.89 (s, 3H), 0.80 (s, 9H), 0.15 (s, 3H), −0.07 (s, 3H). MS: m/z=430.2 (M+1).

Step F—Synthesis of Compound Int-4f

To a solution of compound Int-4e (2 g, 4.65 mmol) in THF (30 mL) was added hexamethylphosphoramide (30.0 g, 167 mmol), LiHMDS (5.11 mL, 5.11 mmol) (1 M) and then 3-iodoprop-1-ene (1.735 mL, 18.59 mmol) at −78° C. The mixture was allowed to stir at −78° C. for 30 min under a nitrogen balloon. The reaction was quenched by water (10 mL) and extracted using ethyl acetate (20 mL×3). The organic layer was concentrated under vacuum, the residue was purified using a silica gel column eluting with 33% ethyl acetate in petroleum ether to provide compound Int-4f as a solid. $^1$H NMR: (400 MHz, CD$_3$OD): δ 8.12 (s, 1H), 6.06-5.94 (m, 1H), 5.24 (d, J=9.9 Hz, 1H), 5.09 (s, 1H), 5.02 (d, J=17.0 Hz, 1H), 4.89 (dd, J=4.4, 9.9 Hz, 1H), 4.01 (s, 3H), 3.03-2.87 (m, 2H), 1.40 (s, 3H), 1.02 (s, 3H), 0.97-0.90 (m, 9H), 0.33 (s, 3H), 0.09 (s, 3H). MS: m/z=471.3 (M+1).

Step G—Synthesis of Compound Int-4g

To a solution of compound Int-4f (1.2 g, 2.6 mmol) in THF/water (4:1, 5 mL) was added potassium osmate(VI) dihydrate (0.188 g, 0.510 mmol) under nitrogen at 15° C. After 5 minutes sodium periodate (2.182 g, 10.20 mmol) was added in three batches over a 10 min period. The reaction was allowed to stir at room temperature for 5 hours. It was quenched by saturated sodium sulfite, then the mixture was diluted with ethyl acetate (10 mL) and water (5 mL). The aqueous layer was extracted with ethyl acetate (20 mL×2), and the combined organic layers were washed with brine (20 mL). The organic layer was concentrated under vacuum to provide crude product which was purified using a silica gel column eluting with 50% ethyl acetate in petroleum ether to provide compound Int-4g. $^1$H NMR (400 MHz, CD$_3$OD): δ 8.30 (s, 1H), 3.97 (s, 3H), 3.51-3.37 (m, 5H), 2.36 (t, J=12.2 Hz, 1H), 2.15-2.06 (m, 1H), 1.35 (s, 3H), 0.98-0.95 (m, 3H), 0.87 (s, 9H), 0.27-0.24 (m, 3H), 0.00 (s, 3H). MS: m/z=504.0; 506.0 (M+1).

Step H—Synthesis of Compound Int-4h

To a solution of compound Int-4g (650 mg, 1.3 mmol) in tetrahydrofuran (10 mL) and H$_2$O (5 mL) was added sodium periodate (1102 mg, 5.15 mmol) under nitrogen. The reaction mixture was allowed to stir at 20° C. for 20 hours. The reaction mixture was quenched by saturated sodium sulfite and the resulting mixture was diluted with ethyl acetate (10 mL) and water (5 mL). The aqueous layer was extracted with ethyl acetate (20 mL×2). The combined organic layers were washed with brine (20 mL), dried over anhydrous sodium sulfate and filtered. The filtrate was concentrated under vacuum to provide compound Int-4h. This material was used in next step without further purification. $^1$H NMR (400 MHz, CDCl$_3$): δ 9.84 (s, 1H), 7.94 (s, 1H), 5.18 (dd, J=3.2, 7.4 Hz, 1H), 4.97 (s, 1H), 4.05 (s, 3H), 3.41-3.34 (m, 1H), 3.18 (dd, J=7.4, 19.5 Hz, 1H), 1.34 (s, 3H), 0.96 (s, 3H), 0.92-0.84 (m, 9H), 0.22 (s, 3H), 0.04--0.06 (m, 3H). MS: m/z=472.0; 474.0 (M+1).

Step I—Synthesis of Compound Int-4i

To a solution of compound Int-4h (470 mg, 0.99 mmol) in methanol (10 mL) was added NaBH$_4$ (75 mg, 1.990 mmol) at 0° C. under nitrogen. The reaction mixture was allowed to stir at 0° C. for 20 minutes. The reaction was diluted with ethyl acetate (10 mL) and water (5 mL). The aqueous layer was extracted with ethyl acetate (20 mL×2), the combined organic layers were washed with brine (20 mL), dried over anhydrous sodium sulfate and filtered. The filtrate was concentrated under vacuum to provide the crude product which was purified using a preparative TLC plate eluting with ethyl acetate to provide compound Int-4i as a solid. $^1$H NMR (400 MHz, CDCl$_3$): δ 7.99 (s, 1H), 4.97 (s, 1H), 4.43 (dd, J=4.3, 9.8 Hz, 1H), 3.98 (s, 3H), 3.95-3.89 (m, 2H), 3.52 (s, 1H), 2.64-2.55 (m, 1H), 2.38-2.29 (m, 1H), 1.44 (s, 3H), 0.89 (s, 9H), 0.83 (s, 3H), 0.26 (s, 3H), 0.05 (s, 3H). MS: m/z=477.4 (M+1).

Step J—Synthesis of Compound Int-4j

The solution of compound Int-4i (390 mg, 0.745 mmol) in dichloromethane (5 mL) was added triethylamine (1.038 mL, 7.45 mmol) and methanesulfonyl chloride (427 mg, 3.72 mmol) at 0° C. The reaction was allowed to stir at 20° C. for 20 h and then 50° C. for 1 hour. The solvent was concentrated under vacuum to provide crude compound Int-4j as an oil. This material was used in next step without further purification. MS: m/z=554.0; 556.0 (M+1).

Step K—Synthesis of Compound Int-4k

A solution of compound Int-4j (410 mg, 0.739 mmol) in tetrahydrofuran (5 mL) was added sodium hydride (59.1 mg, 1.479 mmol) at 0° C. The reaction mixture was allowed to stir at 0° C. for 1 hour. The reaction mixture was poured into water (10 mL), and the aqueous was extracted with ethyl acetate (10 mL×2). The combined organic layers were washed with brine (20 mL) and dried over Na$_2$SO$_4$, the mixture was filtered and the filtrate was concentrated in vacuum to provide compound Int-4k as an oil. This material was used in next step without further purification. $^1$H NMR (400 MHz, CD$_3$OD): δ 8.39 (s, 1H), 5.07 (q, J=8.6 Hz, 1H), 4.81 (s, 1H), 4.10-4.02 (m, 2H), 3.93 (s, 3H), 3.72-3.63 (m, 1H), 2.68-2.61 (m, 1H), 2.36-2.26 (m, 1H), 1.40 (s, 3H), 1.05-0.83 (m, 12H), 0.79 (s, 3H), 0.28 (s, 3H). MS: m/z=458.0 (M+1).

Step L—Synthesis of Compound Int-4l

To a solution of compound Int-4k (330 mg, 0.720 mmol) in tetrahydrofuran (5 mL) was added tetrabutylammonium fluoride (1.440 mL, 1.440 mmol) at 30° C. The reaction mixture was allowed to stir at 30° C. for 5 hours. The reaction mixture was concentrated under vacuum. The resulting residue was purified using a preparative TLC plate eluting with 10% methanol/ethyl acetate to provide compound Int-4l as an oil. $^1$H NMR (400 MHz, CD$_3$OD): δ 8.26 (s, 1H), 4.08-4.02 (m, 1H), 3.94 (d, J=6.4 Hz, 1H), 3.86 (s, 3H), 3.66 (q, J=7.9 Hz, 1H), 3.21 (d, J=8.6 Hz, 2H), 2.73 (dt, J=7.5, 12.9 Hz, 1H), 2.32-2.22 (m, 1H), 1.37 (s, 3H), 0.81 (s, 3H).

Step M—Synthesis of Compound Int-4m

To a solution of compound Int-4l (220 mg, 0.00 mmol) in dichloromethane (2 mL) and tetrahydrofuran (2 mL) was added Dess Martin periodinane (542 mg, 1.278 mmol) at 0° C. The reaction mixture was allowed to stir at 20° C. for 1 hour. The reaction mixture was quenched with aqueous of sodium sulfite, and the resulting mixture was extracted with dichloromethane (2×10 mL). The combined organics were concentrated under vacuum. The resulting residue was purified using a preparative TLC plate eluting with ethyl acetate to provide compound Int-4m as a solid. $^1$H NMR: (400 MHz, CD$_3$OD): δ 8.37 (s, 1H), 5.10 (br. s., 1H), 4.14 (d, J=3.7 Hz, 1H), 3.84 (s, 3H), 3.79 (t, J=6.9 Hz, 2H), 2.77-2.66 (m, 1H), 2.33-2.21 (m, 1H), 1.28 (s, 3H), 1.17 (s, 3H).

Step N—Synthesis of Compound Int-4n and Compound Int-4o

To a mixture of compound Int-4m (30 mg, 0.09 mmol) in DMSO (2 mL) was added (2,4-difluorophenyl)methanamine (25.10 mg, 0.175 mmol), diisopropylethylamine (0.061 mL, 0.351 mmol) and Pd(Ph$_3$P)$_4$ (50.7 mg, 0.044 mmol) under a carbon monoxide balloon. The mixture was allowed to stir at 90° C. for 3 h under a carbon monoxide balloon. The reaction mixture was poured into water (10 mL) and extracted with ethyl acetate (10 mL×2). The combined organic layers were washed with brine, dried over anhydrous sodium sulfate. The solid was filtered off and the filtrate was concentrated under vacuum. The resulting residue was purified using a preparative TLC plate eluting with ethyl acetate to provide the racemic mixture of the desired product, which was further separated using SFC (Column: C2 250 mm*30 mm, 10 um, condition: Base-MeOH Begin B 45%, Flow-Rate: 80 mL/minutes Wavelength: 220 nm) to provide desired compound Int-4n (the first eluting compound) and compound Int-4o (the second eluting compound), both as solids.

Compound Int-4n: $^1$H NMR (400 MHz, CDCl$_3$): δ 10.41 (br. s., 1H), 8.46 (s, 1H), 7.40-7.31 (m, 1H), 6.90-6.71 (m, 2H), 4.85 (br. s., 1H), 4.62 (t, J=4.9 Hz, 2H), 4.07 (d, J=4.7 Hz, 1H), 3.99 (s, 3H), 3.92-3.78 (m, 2H), 2.70 (qd, J=7.1, 14.2 Hz, 1H), 2.32-2.22 (m, 1H), 1.35 (s, 3H), 1.17 (s, 3H).

Compound Int-4o: $^1$H NMR (400 MHz, CDCl$_3$): δ 10.42 (br. s., 1H), 8.46 (s, 1H), 7.40-7.31 (m, 1H), 6.85-6.75 (m, 2H), 4.91-4.90 (m, 1H), 4.61 (t, J=5.3 Hz, 2H), 4.06 (d, J=5.1 Hz, 1H), 3.99 (s, 3H), 3.91-3.81 (m, 2H), 2.75-2.66 (m, 1H), 2.32-2.23 (m, 1H), 1.35 (s, 3H), 1.17 (s, 3H). MS: m/z=433.0 (M+1).

Step O—Synthesis of Compound 5 and Compound 6

To a solution of compound Int-4n (24 mg, 0.056 mmol) in DMF (5 mL) was added anhydrous lithium chloride (23.53 mg, 0.555 mmol). The resulting solution was allowed to stir at 100° C. for 10 h under nitrogen. The reaction mixture was cooled to room temperature and purified using prep-HPLC (TFA) to provide compound 5 as a solid. ¹H NMR (400 MHz, CD₃OD): δ 8.56 (s, 1H), 7.46-7.35 (m, 1H), 7.00-6.87 (m, 2H), 5.21 (br. s., 1H), 4.62 (br. s., 2H), 4.16 (d, J=3.5 Hz, 1H), 3.87 (dt, J=3.7, 8.7 Hz, 1H), 3.74 (q, J=8.1 Hz, 1H), 2.80-2.68 (m, 1H), 2.44-2.34 (m, 1H), 1.37 (s, 3H), 1.25 (s, 3H). MS: m/z=419.1 (M+1).

Compound 6 was prepared using the method described in this Example above, substituting compound Int-4n with compound Int-4o. ¹H NMR (400 MHz, CD₃OD): δ 8.56 (s, 1H), 7.48-7.36 (m, 1H), 7.00-6.87 (m, 2H), 5.21 (br. s., 1H), 4.62 (br. s., 2H), 4.16 (d, J=3.9 Hz, 1H), 3.87 (dt, J=3.9, 9.0 Hz, 1H), 3.74 (q, J=8.1 Hz, 1H), 2.80-2.68 (m, 1H), 2.43-2.33 (m, 1H), 1.37 (s, 3H), 1.25 (s, 3H). MS: m/z=419.1 (M+1).

Example 5

Preparation of Compound 7 and Compound 8

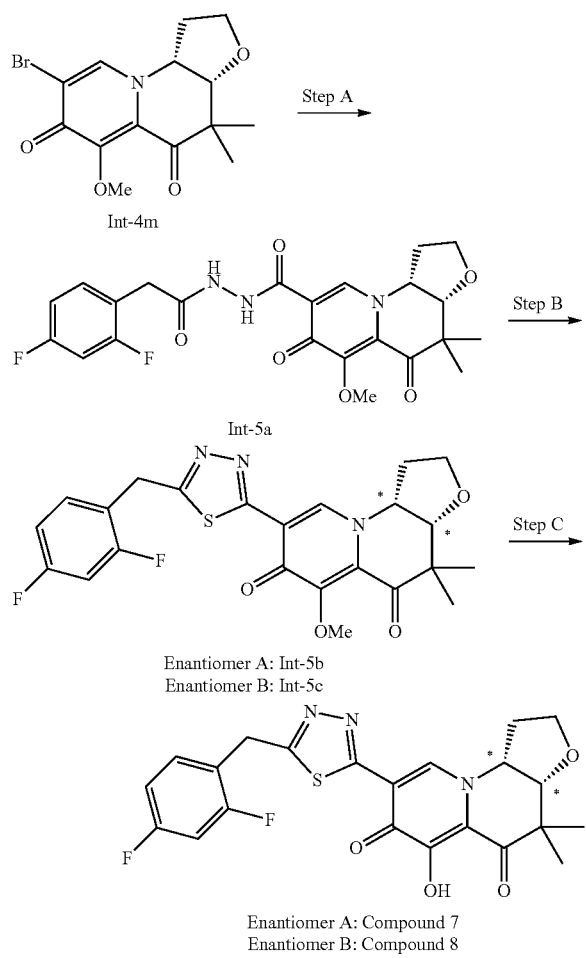

Step A—Synthesis of Compound Int-5a

To a solution of compound Int-4m (50 mg, 0.146 mmol) in DMSO (1.5 mL) were added 2-(2,4-difluorophenyl)acetohydrazide (82 mg, 0.44 mmol), diisopropylethylamine (0.13 mL, 0.73 mmol), Pd(Ph₃P)₄ (84 mg, 0.073 mmol). The mixture was allowed to stir at 85° C. under carbon monoxide atmosphere for 10 hours. It was diluted with EtOAc (20 mL), washed with water 20 mL and brine. The organic layer was dried over anhydrous sodium sulfate, filtered and concentrated in vacuo. The residue obtained was purified using a preparative TLC plate eluting with 5% MeOH/dichloromethane to provide compound Int-5a as a solid. MS: m/z=476.2 (M+1).

Step B—Synthesis of Compound Int-5b and Compound Int-5c

To a solution of compound Int-5a (75 mg, 0.158 mmol) in THF (2 mL) was added Lawesson's Reagent (191 mg, 0.47 mmol) and 2,4,6-tripropyl-2,4,6-tripropyl-1,3,5,2,4,6-trioxatriphosphinane 2,4,6-trioxide (100 mg, 0.32 mmol). The reaction was allowed to stir at 80° C. for 6 hours. The reaction mixture was cooled to room temperature and purified using prep-HPLC (TFA) to provide the desired product as a racemic mixture. This material was further separated using a chiral preparative SFC (Column: OJ (250 mm*30 mm, 10 um) Mobile phase: 30% Base-EtOH (contained 0.1% NH₃.H₂O) in CO₂ Flow rate: 80 mL/min Wavelength: 220 nm) to provide compound Int-5b (enantiomer A, the first eluting compound) as an oil and compound Int-5c (enantiomer B, the second eluting compound) as an oil. MS: m/z=474.1 (M+1).

Step C—Synthesis of Compound 7 and Compound 8

To a solution of compound Int-5b (13 mg, 0.027 mmol) in Actonitrile (0.4 mL) was added magnesium bromide (101 mg, 0.549 mmol). It was allowed to stir at 23° C. for 16 hours. The reaction mixture was purified using a pre-HPLC (TFA) to provide compound 7 as a solid. ¹H NMR (400 MHz, CDCl₃): δ 8.83 (s., 1H), 7.27-7.35 (m, 1H), 6.84-6.91 (m, 2H), 5.01 (s, 1H), 4.49 (s, 2H), 4.12 (d, J=4.0 Hz, 1H), 3.86-3.97 (m, 2H), 2.80 (dd, J=6.0 Hz, 1H), 2.47 (dd, J=6.0 Hz, 1H), 1.46 (s, 3H), 1.31 (s, 3H). MS: m/z=460.1 (M+1).

Compound 8 was prepared using the method described in this Example above, substituting compound Int-5b with compound Int-5c. ¹H NMR (400 MHz, CDCl₃): δ 8.83 (s., 1H), 7.27-7.35 (m, 1H), 6.84-6.91 (m, 2H), 5.01 (s, 1H), 4.49 (s, 2H), 4.12 (d, J=4.0 Hz, 1H), 3.86-3.97 (m, 2H), 2.80 (dd, J=6.0 Hz, 1H), 2.47 (dd, J=6.0 Hz, 1H), 1.46 (s, 3H), 1.31 (s, 3H). MS: m/z=460.1 (M+1).

Example 6

Preparation of Compounds 9 and 10

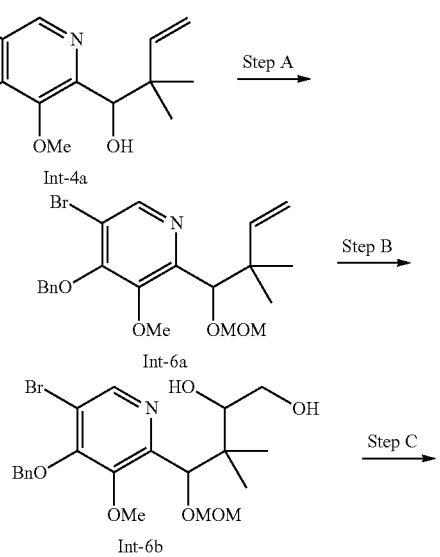

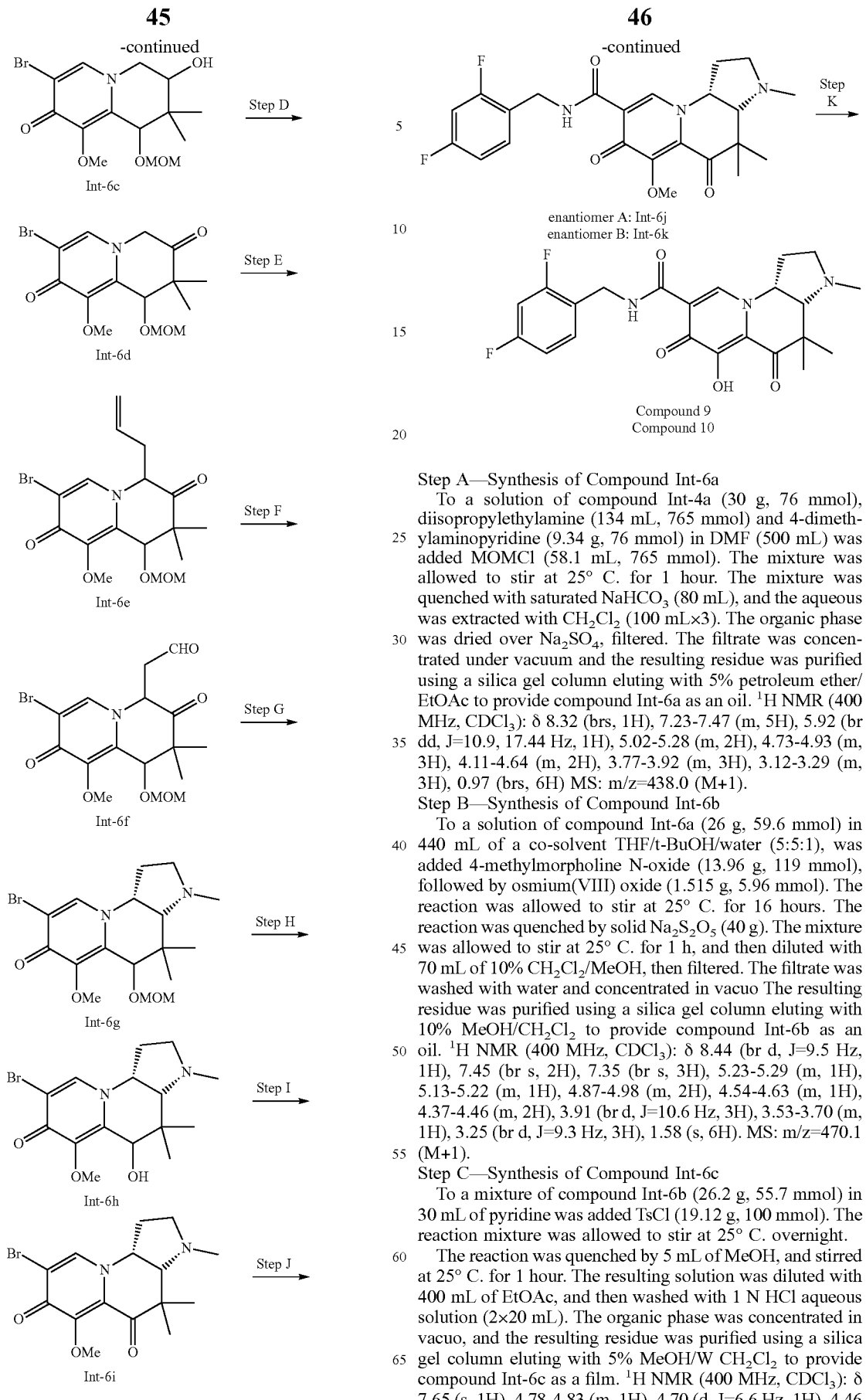

Step A—Synthesis of Compound Int-6a

To a solution of compound Int-4a (30 g, 76 mmol), diisopropylethylamine (134 mL, 765 mmol) and 4-dimethylaminopyridine (9.34 g, 76 mmol) in DMF (500 mL) was added MOMCl (58.1 mL, 765 mmol). The mixture was allowed to stir at 25° C. for 1 hour. The mixture was quenched with saturated $NaHCO_3$ (80 mL), and the aqueous was extracted with $CH_2Cl_2$ (100 mL×3). The organic phase was dried over $Na_2SO_4$, filtered. The filtrate was concentrated under vacuum and the resulting residue was purified using a silica gel column eluting with 5% petroleum ether/EtOAc to provide compound Int-6a as an oil. $^1$H NMR (400 MHz, $CDCl_3$): δ 8.32 (brs, 1H), 7.23-7.47 (m, 5H), 5.92 (br dd, J=10.9, 17.44 Hz, 1H), 5.02-5.28 (m, 2H), 4.73-4.93 (m, 3H), 4.11-4.64 (m, 2H), 3.77-3.92 (m, 3H), 3.12-3.29 (m, 3H), 0.97 (brs, 6H) MS: m/z=438.0 (M+1).

Step B—Synthesis of Compound Int-6b

To a solution of compound Int-6a (26 g, 59.6 mmol) in 440 mL of a co-solvent THF/t-BuOH/water (5:5:1), was added 4-methylmorpholine N-oxide (13.96 g, 119 mmol), followed by osmium(VIII) oxide (1.515 g, 5.96 mmol). The reaction was allowed to stir at 25° C. for 16 hours. The reaction was quenched by solid $Na_2S_2O_5$ (40 g). The mixture was allowed to stir at 25° C. for 1 h, and then diluted with 70 mL of 10% $CH_2Cl_2$/MeOH, then filtered. The filtrate was washed with water and concentrated in vacuo The resulting residue was purified using a silica gel column eluting with 10% MeOH/$CH_2Cl_2$ to provide compound Int-6b as an oil. $^1$H NMR (400 MHz, $CDCl_3$): δ 8.44 (br d, J=9.5 Hz, 1H), 7.45 (br s, 2H), 7.35 (br s, 3H), 5.23-5.29 (m, 1H), 5.13-5.22 (m, 1H), 4.87-4.98 (m, 2H), 4.54-4.63 (m, 1H), 4.37-4.46 (m, 2H), 3.91 (br d, J=10.6 Hz, 3H), 3.53-3.70 (m, 1H), 3.25 (br d, J=9.3 Hz, 3H), 1.58 (s, 6H). MS: m/z=470.1 (M+1).

Step C—Synthesis of Compound Int-6c

To a mixture of compound Int-6b (26.2 g, 55.7 mmol) in 30 mL of pyridine was added TsCl (19.12 g, 100 mmol). The reaction mixture was allowed to stir at 25° C. overnight. The reaction was quenched by 5 mL of MeOH, and stirred at 25° C. for 1 hour. The resulting solution was diluted with 400 mL of EtOAc, and then washed with 1 N HCl aqueous solution (2×20 mL). The organic phase was concentrated in vacuo, and the resulting residue was purified using a silica gel column eluting with 5% MeOH/W $CH_2Cl_2$ to provide compound Int-6c as a film. $^1$H NMR (400 MHz, $CDCl_3$): δ 7.65 (s, 1H), 4.78-4.83 (m, 1H), 4.70 (d, J=6.6 Hz, 1H), 4.46

(d, J=6.6 Hz, 1H), 4.26-4.39 (m, 2H), 3.97 (s, 3H), 3.69 (br dd, J=6.0, 12.8 Hz, 1H), 3.32-3.43 (m, 3H), 1.60 (s, 3H), 1.31 (s, 3H). MS: m/z=362.2 (M+1).

Step D—Synthesis of Compound Int-6d

To a mixture of compound Int-6c (17 g, 46.9 mmol) in $CH_2Cl_2$ (300 mL) was added Dess Martin periodinane (39.8 g, 94 mmol). The reaction was allowed to stir at 25° C. overnight. The mixture was filtered and the filtrate was concentrated in vacuo. The resulting residue was purified using a silica gel column eluting with 5% MeOH/$CH_2Cl_2$ to provide compound Int-6d as a film. $^1$H NMR (500 MHz, $CD_3OD$): δ 8.18 (s, 1H), 5.11 (s, 1H), 4.73 (br d, J=7.8 Hz, 2H), 4.63-4.67 (m, 1H), 4.57-4.62 (m, 1H), 3.91-3.96 (m, 3H), 3.31 (s, 3H), 1.35 (s, 3H), 0.92 (s, 3H).

Step E—Synthesis of Compound Int-6e

To a solution of compound Int-6d (400 mg, 1.110 mmol) and 3-iodoprop-1-ene (1015 μL, 11.10 mmol) in THF (16.5 mL) cooled to −78° C., was added hexamethylphosphoramide (8226 μl), followed by rapid addition of LiHMDS (2.22 mL, 2.221 mmol). The mixture was allowed to stir at −78° C. for 20 minutes. The reaction was quenched with saturated $NH_4Cl$ aqueous solution. The mixture was diluted with water, and extracted with EtOAc. The organic layers were combined, dried over $Na_2SO_4$ and concentrated in vacuo The resulting residue was purified using ISCO normal phase HP Gold silica gel (40 g), eluting with $CH_2Cl_2$/MeOH (100% $CH_2Cl_2$ for 5 min; gradient to 10% MeOH in $CH_2Cl_2$ over 15 minutes isocratic for 5 min) to provide compound Int-6e as an oil. LCMS anal. calcd. for $C_{17}H_{22}BrNO_5$: 399.07; Found: 400.12 (M+1)$^+$.

Step F—Synthesis of Compound Int-6f

To a solution of compound Int-6e (300 mg, 0.750 mmol) in MeOH (17 mL) cooled to −20° C., was bubbled through ozone gas. The mixture was allowed to stir at −20° C. for 20 minutes. To this mixture was added $Ph_3P$ (393 mg, 1.499 mmol). The mixture was allowed to stir at room temperature for 30 minutes. The volatile was removed under vacuo. The resulting residue was purified using ISCO, normal phase HP Gold silica gel (40 g), eluting with Hexanes/EtOAc (100% Hexanes for 5 min; gradient to 100% EtOAc over 25 minutes isocratic for 5 min) to provide compound Int-6f as a solid. LCMS anal. calcd. for $C_{16}H_{20}BrNO_6$: 401.05; Found: 402.05 (M+1)$^+$.

Step G—Synthesis of Compound Int-6g

To a solution of compound Int-6f (127 mg, 0.316 mmol) in $CH_2Cl_2$ (2.5 mL) at room temperature, was added methylamine (2 mL of 2.0 M in THF, 4.00 mmol), followed by $NaBH_3CN$ (298 mg, 4.74 mmol). The mixture was allowed to stir at room temperature for 15 minutes. To the mixture was added MeOH (5 mL) followed by acetic acid (0.271 mL, 4.74 mmol). The mixture was allowed to stir at room temperature for 4 hours. The mixture was concentrated in vacuo. The resulting residue was diluted with saturated $NaHCO_3$ and extracted with $CH_2Cl_2$. The organic layers were combined and concentrated in vacuo The resulting residue was purified using ISCO, normal phase HP Gold silica gel (24 g), eluting with Hexanes/EtOAc:EtOH (3:1) (gradient from 0 to 100% EtOAc:EtOH in Hexane over 15 minutes isocratic for 5 min) to provide compound Int-6g. LCMS anal. calcd. for $C_{17}H_{25}BrN_2O_4$: 400.10; Found: 401.18 (M+1)$^+$.

Step H—Synthesis of Compound Int-6h

To a solution of compound Int-6g (56.4 mg, 0.141 mmol) in MeOH (1 mL), was added HCl (12 N) (0.5 ml, 6.09 mmol). The reaction was heated at 60° C. for 5 hours. The volatile was removed under vacuo. The resulting residue was dissolved in $H_2O$, then purified using preparative HPLC (reverse phase, YMC-Pack ODS C-18 100×20 mm) eluting with acetonitrile/water/0.05% TFA (0% to 50% organic in 10 minutes then to 100% in 2 minutes 20 mL/min). Related fractions were pooled and evaporated under reduced pressure to provide compound Int-6h as an oil. LCMS anal. calcd. for $C_{15}H_{21}BrN_2O_3$: 356.07; Found: 357.12 (M+1)$^+$.

Step I—Synthesis of Compound Int-6i

To a suspension of compound Int-6h TFA salt (61.7 mg, 0.131 mmol) in $CH_2Cl_2$ (6.5 mL) at room temperature under $N_2$, was added Hunig's Base (22.87 μl, 0.131 mmol). The mixture was stirred for 15 minutes. Then Dess-Martin Periodinane (58.3 mg, 0.137 mmol) was added. The reaction was allowed to stir at room temperature for 4 hours. The mixture was diluted with $CH_2Cl_2$ and washed with saturated. $Na_2CO_3$ twice. The aqueous layer was extracted with $CH_2Cl_2$. The combined organic layers were evaporated in vacuo. The resulting residue was redissolved in acetonitrile (50 mL) and filtered. The filtrate was concentrated in vacuo. The resulting residue was purified using ISCO, normal phase HP Gold silica gel (40 g), eluting with $CH_2Cl_2$/MeOH (5% MeOH in $CH_2Cl_2$ for 35 min) to provide compound Int-6i as a solid. LCMS anal. calcd. for $C_{15}H_{19}BrN_2O_3$: 354.06; Found: 355.29 (M+1)$^+$.

Step J—Synthesis of Compound Int-6j and Compound Int-6k

The mixture of compound Int-6i (35.8 mg, 0.101 mmol), N-ethyl-N-isopropylpropan-2-amine (53.8 μl, 0.302 mmol)), (2,4-difluorophenyl)methanamine (24.04 μL, 0.202 mmol) and (oxybis(2,1-phenylene))bis(diphenylphosphine) (27.1 mg, 0.050 mmol) in DMSO (2.5 mL) under $N_2$ was stirred for 5 minutes then added Pd(OAc)$_2$ (11.31 mg, 0.050 mmol). A stream of CO gas was bubbled through the above reaction mixture for 20 minutes. Then the mixture was heated at 90° C. under CO balloon for 1 hour. The reaction was diluted with DMSO and filtered through a filter disc. The resulting residue was purified using a preparative HPLC (reverse phase, YMC-Pack ODS C-18 100×20 mm) eluting with acetonitrile/water/0.05% TFA (0% to 80% organic in 10 minutes then to 100% in 2 minutes 20 mL/min). Related fractions were pooled and evaporated under reduced pressure to provide the desired compound as a racemate. This material was further separated using a chiral column (AD, 30×250 mm, 35% MeOH (0.2% $NH_4OH$)/CO2, 70 ml/minutes 100 bar, 20 mg/ml in MeOH) to provide in order of elution compound Int-6j (enantiomer A) and compound Int-6k (enantiomer B). LCMS anal. calcd. for $C_{23}H_{25}F_2N_3O_4$: 445.18; Found: 446.23 (M+1)$^+$.

Step K—Synthesis of Compound 9 and Compound 10

The mixture of enantiomer A compound Int-6j (17.2 mg, 0.039 mmol) and lithium chloride (16.4 mg, 0.39 mmol) in DMF (1 mL) was heated at 100° C. for 2 hours. At completion, it was cooled down to room temperature and diluted with DMSO. The crude was purified using a preparative HPLC (reverse phase, YMC-Pack ODS C-18 100×20 mm) eluting with acetonitrile/water/0.05% TFA (0% to 70% organic in 10 minutes then to 100% in 2 minutes 20 mL/min). Related fractions were pooled and evaporated under reduced pressure, lyophilized to provide compound 9 as a solid. $^1$H NMR (500 MHz, $CD_3OD$): δ 8.63 (s, 1H); 7.48-7.40 (m, 1H); 7.01-6.91 (m, 2 H); 5.55-5.46 (m, 1 H); 4.74-4.58 (m, 2 H); 4.24-4.12 (m, 1 H); 3.50-3.15 (m, 3 H); 3.00 (s, 3H); 2.92-2.74 (m, 1 H); 2.61-2.48 (m, 1 H); 1.53 (s, 3 H); 1.42 (s, 3 H). LCMS anal. calcd. for $C_{22}H_{23}F_2N_3O_4$: 431.17; Found: 432.22 (M+1)$^+$.

Compound 10 was prepared using the method described in this Example above, substituting compound Int-6j with compound Int-6k. $^1$H NMR (500 MHz, $CD_3OD$): δ 8.63 (s, 1H); 7.48-7.40 (m, 1 H); 7.01-6.91 (m, 2 H); 5.55-5.46 (m, 1 H); 4.74-4.58 (m, 2 H); 4.24-4.12 (m, 1 H); 3.50-3.15 (m, 3 H); 3.00 (s, 3H); 2.92-2.74 (m, 1 H); 2.61-2.48 (m, 1 H); 1.53 (s, 3 H); 1.42 (s, 3 H). LCMS anal. calcd. for $C_{22}H_{23}F_2N_3O_4$: 431.17; Found: 432.20 (M+1)⁺.

Example 7

Preparation of Compound Int-7c

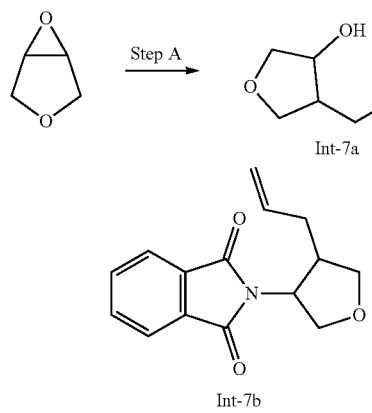

Step A—Synthesis of Compound Int-7a

To a solution of 3,6-dioxabicyclo[3.1.0]hexane (25 g, 290 mmol) in THF (1 L) was added dropwise allylmagnesium bromide (871 mL, 871 mmol, 1M) at 0° C. The mixture was refluxed at 60° C. for 2 hours. The reaction was then cooled to 0° C. and quenched by saturated NH₄Cl solution (300 mL). The aqueous was extracted with EtOAc (1500 mL). The organic phase was dried over anhydrous sodium sulfate, filtered and concentrated in vacuo to provide compound Int-7a as an oil. This material was used in the next step without further purification. ¹H NMR (400 MHz, CDCl₃): δ 5.73-5.83 (m, 1H), 5.01-5.08 (m, 2H), 3.98-4.08 (m, 2H), 3.84-3.92 (m, 1H), 3.65-3.75 (m, 1H), 3.45-3.56 (m, 1H), 3.05-3.25 (m, 2H), 1.89-3.01 (m, 1H).

Step B—Synthesis of Compound Int-7b

To a solution of compound Int-7a (14 g, 109 mmol), Ph₃P (43.0 g, 164 mmol), isoindoline-1,3-dione (24.11 g, 164 mmol) in THF (700 mL) was added dropwise DIAD (43.5 mL, 218 mmol) at 0° C. The mixture was allowed to stir at 23° C. for 12 hours. The solvent was removed under vacuum. The resulting mixture was purified using a silica gel column eluting with 25% EtOAc in petroleum ether to provide compound Int-7b as an oil. ¹H NMR (400 MHz, CDCl₃): δ 7.74-7.86 (m, 4H), 5.66-5.75 (m, 1H), 4.95-5.12 (m, 3H), 4.20-4.33 (m, 2H), 4.06-4.18 (m, 1H), 3.85-3.97 (m, 1H), 3.52-3.62 (m, 1H), 3.01-3.15 (m, 2H).

Step C—Synthesis of Compound Int-7c

To a solution of compound Int-7b (19 g, 73.8 mmol) in EtOH (400 mL) was added hydrazine (5.45 mL, 148 mmol). The mixture was refluxed at 90° C. for 2 hours. The reaction was cooled to room temperature and concentrated HCl (30.3 mL, 369 mmol) was then added dropwise. The resulting mixture was filtered and the cake was washed with EtOH (100 mL). The filtrate was concentrated in vacuo and the resulting residue was treated with water (200 mL). The aqueous solution was washed with EtOAc (100 mL×3) and then basified to pH=12 by sodium hydroxide (17.72 g, 443 mmol). This was extracted with CH₂Cl₂ (150 mL×3), dried over anhydrous sodium sulfate, filtered and concentrated in vacuo to provide compound Int-7c as an oil. This material was used directly without further purification. ¹H NMR (400 MHz, CDCl₃): δ 5.75-5.84 (m, 1H), 5.01-5.15 (m, 2H), 3.84-3.94 (m, 2H), 3.46-3.57 (m, 3H), 3.05-3.26 (m, 3H).

Example 8

Preparation of Compounds 11 and 12

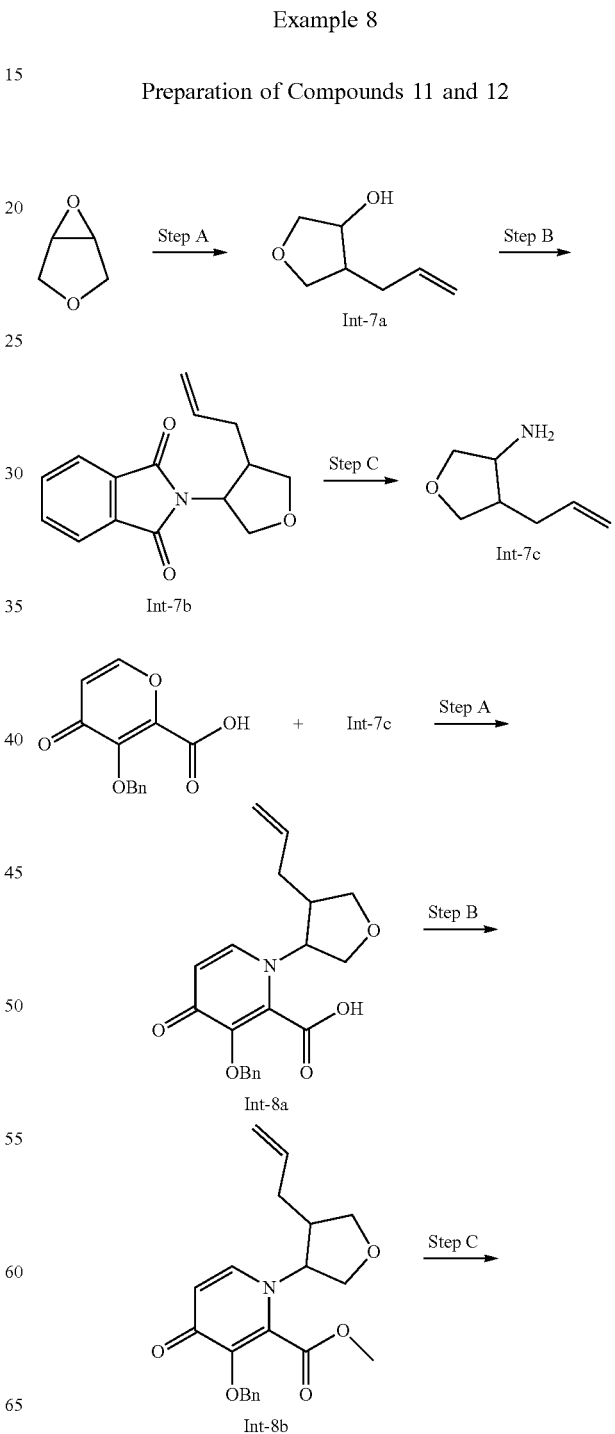

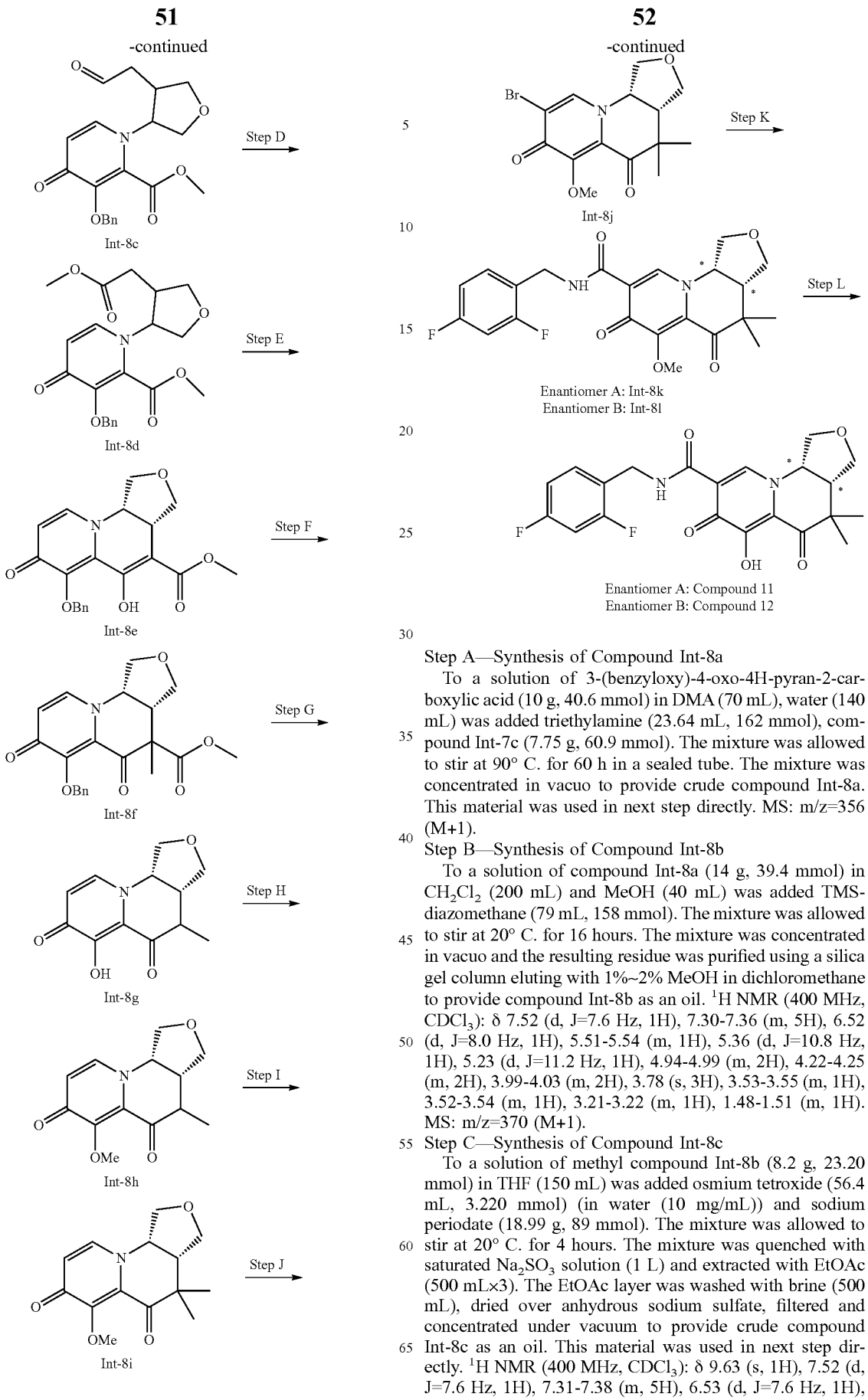

Step A—Synthesis of Compound Int-8a

To a solution of 3-(benzyloxy)-4-oxo-4H-pyran-2-carboxylic acid (10 g, 40.6 mmol) in DMA (70 mL), water (140 mL) was added triethylamine (23.64 mL, 162 mmol), compound Int-7c (7.75 g, 60.9 mmol). The mixture was allowed to stir at 90° C. for 60 h in a sealed tube. The mixture was concentrated in vacuo to provide crude compound Int-8a. This material was used in next step directly. MS: m/z=356 (M+1).

Step B—Synthesis of Compound Int-8b

To a solution of compound Int-8a (14 g, 39.4 mmol) in $CH_2Cl_2$ (200 mL) and MeOH (40 mL) was added TMS-diazomethane (79 mL, 158 mmol). The mixture was allowed to stir at 20° C. for 16 hours. The mixture was concentrated in vacuo and the resulting residue was purified using a silica gel column eluting with 1%~2% MeOH in dichloromethane to provide compound Int-8b as an oil. $^1$H NMR (400 MHz, $CDCl_3$): δ 7.52 (d, J=7.6 Hz, 1H), 7.30-7.36 (m, 5H), 6.52 (d, J=8.0 Hz, 1H), 5.51-5.54 (m, 1H), 5.36 (d, J=10.8 Hz, 1H), 5.23 (d, J=11.2 Hz, 1H), 4.94-4.99 (m, 2H), 4.22-4.25 (m, 2H), 3.99-4.03 (m, 2H), 3.78 (s, 3H), 3.53-3.55 (m, 1H), 3.52-3.54 (m, 1H), 3.21-3.22 (m, 1H), 1.48-1.51 (m, 1H). MS: m/z=370 (M+1).

Step C—Synthesis of Compound Int-8c

To a solution of methyl compound Int-8b (8.2 g, 23.20 mmol) in THF (150 mL) was added osmium tetroxide (56.4 mL, 3.220 mmol) (in water (10 mg/mL)) and sodium periodate (18.99 g, 89 mmol). The mixture was allowed to stir at 20° C. for 4 hours. The mixture was quenched with saturated $Na_2SO_3$ solution (1 L) and extracted with EtOAc (500 mL×3). The EtOAc layer was washed with brine (500 mL), dried over anhydrous sodium sulfate, filtered and concentrated under vacuum to provide crude compound Int-8c as an oil. This material was used in next step directly. $^1$H NMR (400 MHz, $CDCl_3$): δ 9.63 (s, 1H), 7.52 (d, J=7.6 Hz, 1H), 7.31-7.38 (m, 5H), 6.53 (d, J=7.6 Hz, 1H), 5.45 (d, J=11.2 Hz, 1H), 5.20 (d, J=11.2 Hz, 1H), 4.24-4.27 (m, 3H), 4.01-4.05 (m, 1H), 3.78 (s, 3H), 3.52-3.56 (s, 1H), 3.07-3.12 (m, 1H), 3.62-3.73 (m, 1H), 3.01-3.06 (m, 1H). MS: m/z=372 (M+1).

Step D—Synthesis of Compound Int-8d

To a solution of compound Int-8c (5 g, 13.46 mmol) in acetonitrile (40 mL) and water (40 mL) was added sodium dihydrogen phosphate (4.85 g, 40.4 mmol) and sodium chlorite (7.31 g, 81 mmol). The mixture was allowed to stir at 20° C. for 12 hours. The mixture was concentrated in vacuo and the resulting residue was dissolved in $CH_2Cl_2$/MeOH (10:1, 50 mL). The solid was filtered off and the filtrate was concentrated under vacuum. The resulting residue was dissolved in $CH_2Cl_2$ (80 mL) and MeOH (16 mL). TMS-diazomethane (25.8 mL, 51.6 mmol) was then added slowly. The mixture was allowed to stir at 20° C. for 3 hours. The mixture was concentrated in vacuo and the resulting residue was purified using a silica gel column eluting with 1%~2% MeOH/$CH_2Cl_2$ to provide compound Int-8d as an oil. $^1$H NMR (400 MHz, $CDCl_3$): δ 7.53 (d, J=7.6 Hz, 1H), 7.30-7.36 (m, 5H), 6.53 (d, J=7.6 Hz, 1H), 5.37 (d, J=11.2 Hz, 1H), 5.21 (d, J=11.2 Hz, 1H), 4.15-4.35 (m, 3H), 4.04-4.08 (m, 1H), 3.78 (s, 3H), 3.66-3.72 (m, 4H), 3.03-3.10 (m, 1H), 3.46-3.50 (m, 1H), 1.86-1.93 (m, 1H). MS: m/z=402 (M+1).

Step E—Synthesis of Compound Int-8e

To a solution of compound Int-8d (3.2 g, 7.97 mmol) in THF (90 mL) was added potassium 2-methylpropan-2-olate (1.789 g, 15.94 mmol) at 0° C. The reaction was allowed to stir at 20° C. for 2 hours. The mixture was quenched with MeOH (10 mL) and concentrated in vacuo The resulting residue was purified using a silica gel column eluting with 5% MeOH/$CH_2Cl_2$ to provide compound Int-8e as a solid. MS: m/z=370 (M+1).

Step F—Synthesis of Compound Int-8f

To a mixture of compound Int-8e (1.8 g, 4.87 mmol)) and $Cs_2CO_3$ (3.18 g, 9.75 mmol) in DMF (20 mL) was added MeI (1.524 mL, 24.37 mmol). The reaction was allowed to stir at 20° C. for 2 hours. The mixture was quenched by addition of water (40 mL), and the aqueous was extracted with $CH_2Cl_2$ (30 mL×4). The combined organic layer was concentrated under reduced pressure and purified using a silica gel column eluting with 5% MeOH/$CH_2Cl_2$ to provide compound Int-8f as a solid. $^1$H NMR (400 MHz, $CDCl_3$): δ 7.41-7.57 (m, 2H), 7.25-7.38 (m, 3H), 7.13-7.23 (m, 1H), 6.44-6.59 (m, 1H), 5.59 (d, J=10.8 Hz, 1H), 5.15-5.30 (m, 1H), 4.43-4.64 (m, 1H), 4.18-4.30 (m, 1H), 4.00 (dd, J=9.8, 3.9 Hz, 1H), 3.76-3.91 (m, 4H), 3.48-3.64 (m, 1H), 3.06-3.22 (m, 1H), 1.28 (s, 3H). MS: m/z=384.1 (M+1).

Step G—Synthesis of Compound Int-8g

To a mixture of compound Int-8f (600 mg, 1.565 mmol) in water (3 mL) and AcOH (6 mL), was added 3 mL of 10 M aqueous HCl solution. The reaction was allowed to stir at 130° C. for 1 hour. The mixture was cooled to 20° C. and purified using preparative HPLC (Column: Waters Xbridge Prep OBD C18 150 mm*30 mm, 5 um; Condition: 0.1% TFA-ACN; Gradient: 0% to 20%; B, 0~11 minute. FlowRate: 40 mL/min) to provide compound Int-8g as a solid. $^1$H NMR (400 MHz, $CD_3OD$): δ 7.87-8.08 (m, 1H), 6.75 (br., 1H), 5.04-5.23 (m, 1H), 4.32 (d, J=7.1 Hz, 1H), 3.99-4.23 (m, 2H), 3.88-3.99 (m, 1H), 3.48-3.63 (m, 1H), 3.82-3.00 (m, 1H), 1.10-1.51 (m, 3H). MS: m/z=236.0 (M+1).

Step H—Synthesis of Compound Int-8h

To a solution of compound Int-8g (270 mg, 1.148 mmol) in $CH_2Cl_2$ (6 mL) and MeOH (2 mL) was added TMS-Diazomethane (1.148 mL, 3.296 mmol). The mixture was allowed to stir at 20° C. for 1 hour. The mixture was concentrated in vacuo and the resulting residue was purified using a preparative TLC plate eluting with 20% MeOH/EtOAc to provide compound Int-8h as an oil. $^1$H NMR (400 MHz, $CD_3OD$): δ 7.87 (d, J=7.5 Hz, 1H), 6.63 (d, J=7.5 Hz, 1H), 5.07-5.15 (m, 1H), 3.99 (dd, J=10.4, 4.9 Hz, 1H), 3.85 (s, 3H), 3.82 (d, J=8.6 Hz, 1H), 3.73 (dd, J=10.4, 1.3 Hz, 1H), 3.63 (dd, J=9.6, 5.6 Hz, 1H), 3.26-3.30 (m, 1H), 3.21 (q, J=6.4 Hz, 1H), 1.13-1.21 (m, 3H). MS: m/z=250.0 (M+1).

Step I—Synthesis of Compound Int-8i

A solution of compound Int-8h (20 mg, 0.080 mmol) in THF (1.5 mL) was cooled to −78° C., and treated with 1 M LiHMDS in THF (0.241 mL, 0.241 mmol,). 1,3-Dimethyl-tetrahydropyrimidin-2(1H)-one (0.720 mL, 5.62 mmol) was then added, and the reaction was allowed to stir at −78° C. for 10 minutes. To the resulting solution was added MeI (0.050 mL, 0.802 mmol). The reaction was warmed to 20° C. and stirred for 3 hours. The reaction was quenched by water (0.2 mL), and then treated with $CH_3CN$ (1.5 mL). The mixture was filtered, and the filtrate was purified using preparative HPLC (Column: YMC-Actus Pro C18 150 mm*30 mm, 5 um; Condition: 0.1% TFA-ACN; Gradient: 0% to 25%; B, 0~11 minute. FlowRate: 40 mL/min) to provide compound Int-8i. $^1$H NMR (400 MHz, $CD_3OD$): δ 8.43 (d, J=7.5 Hz, 1H), 7.34 (d, J=7.5 Hz, 1H), 5.39 (t, J=5.3 Hz, 1H), 4.24 (dd, J=10.5, 4.5 Hz, 1H), 4.02-4.10 (m, 2H), 3.98 (s, 3H), 3.58-3.68 (m, 1H), 3.17-3.23 (m, 1H), 1.28 (d, J=19.1 Hz, 6H). MS: m/z=264.0 (M+1).

Step J—Synthesis of Compound Int-8j

To a solution of compound Int-8i (10 mg, 0.038 mmol) in $CH_2Cl_2$ (1 mL) was added NBS (10.14 mg, 0.057 mmol). The reaction was allowed to stir at 0° C. for 10 minutes. It was quenched with saturated aqueous sodium sulfite solution (0.5 mL), and then diluted with $CH_2Cl_2$ (5 mL). The resulting mixture was dried over sodium sulfate, filtered and concentrated in vacuo The resulting residue was purified using a preparative TLC plate eluting with 5% MeOH/EtOAc to provide compound Int-8j as a solid. $^1$H NMR (400 MHz, $CDCl_3$): δ 7.63 (s, 1H), 4.70 (br., 1H), 4.13-4.22 (m, 1H), 3.88-4.07 (m, 4H), 3.81 (d, J=9.0 Hz, 1H), 3.50 (t, J=9.3 Hz, 1H), 3.78-3.84 (m, 1H), 1.12-1.26 (m, 6H). MS: m/z=343.0, 344.0 (M+1).

Step K—Synthesis of Compound Int-8k and Compound Int-8l

To a mixture of compound Int-8j (18 mg, 0.053 mmol), diisopropylethylamine (0.037 mL, 0.210 mmol) and (2,4-difluorophenyl)methanamine (15.06 mg, 0.105 mmol) in DMSO (1 mL), was added $Pd(Ph_3P)_4$ (30.4 mg, 0.026 mmol) under $N_2$. The mixture was allowed to stir at 80° C. for 2 h under a CO balloon. The reaction mixture was diluted with EtOAc (5 mL) and filtered. The filtrate was washed with diluted HCl (5 mL) and the aqueous layer was extracted with EtOAc (5 mL×3), then the combined organic phase was washed with brine (10 mL), dried and concentrated in vacuo The resulting residue was purified using a preparative TLC plate eluting with EtOAc to provide the desired product as racemate. This material was further separated using SFC (Column: IC (250 mm*30 mm, 10 um); Condition: Base-EtOH, FlowRate (mL/min): 80, Wavelength: 220 nm) to provide compound Int-8k (enantiomer A, the first eluting compound) as a solid and compound Int-8l (enantiomer B, the second eluting compound) as a solid.

Compound Int-8k: $^1$H NMR (400 MHz, $CD_3OD$): δ 8.57 (s, 1H), 7.37-7.48 (m, 1H), 6.86-7.01 (m, 2H), 5.12-5.22 (m, 1H), 4.61 (s, 2H), 4.15 (dd, J=10.2, 4.7 Hz, 1H), 3.90-4.00 (m, 2H), 3.87 (s, 3H), 3.50-3.58 (m, 1H), 3.07 (q, J=8.0 Hz, 1H), 1.15-1.28 (m, 6H). MS: m/z=433.2 (M+1).

Compound Int-8l: $^1$H NMR (400 MHz, CD$_3$OD): δ 8.57 (s, 1H), 7.36-7.47 (m, 1H), 6.86-7.00 (m, 2H), 5.14-5.23 (m, 1H), 4.61 (s, 2H), 4.15 (dd, J=10.6, 4.7 Hz, 1H), 3.90-4.00 (m, 2H), 3.87 (s, 3H), 3.50-3.61 (m, 1H), 3.08 (q, J=8.2 Hz, 1H), 1.15-1.26 (m, 6H). MS: m/z=433.2 (M+1).

Step L—Synthesis of Compound 11 and Compound 12

To a solution of compound Int-8k (7 mg, 0.016 mmol) in DMF (5 mL) was added anhydrous LiCl (6.86 mg, 0.162 mmol). The resulting solution was allowed to stir at 80° C. for 12 hours. LCMS showed the reaction was completed. The reaction mixture was purified using preparative HPLC (Column: Phenomenex Synergi C18 150 mm*30 mm*4 um; Condition: 0.1% TFA-ACN; Gradient: 33% to 63%; B, 0~8 minutes. FlowRate: 30 mL/min) to provide compound 11 as a solid. $^1$H NMR (400 MHz, CD$_3$OD): δ 8.58 (s, 1H), 7.37-7.49 (m, 1H), 6.87-7.03 (m, 2H), 5.19 (br., 1H), 4.64 (s, 2H), 4.24 (d, J=7.7 Hz, 1H), 4.06-4.16 (m, 2H), 3.55 (t, J=9.4 Hz, 1H), 3.06-3.16 (m, 1H), 1.15-1.51 (m, 6H). MS: m/z=419.0 (M+1).

Compound 12 was prepared using the method described in this Example above, substituting compound Int-8k with compound Int-8l. $^1$H NMR (400 MHz, CD$_3$OD): δ 8.58 (s, 1H), 7.35-7.49 (m, 1H), 6.88-7.02 (m, 2H), 5.19 (br., 1H), 4.64 (s, 2H), 4.24 (d, J=9.3 Hz, 1H), 4.06-4.18 (m, 2H), 3.55 (t, J=9.4 Hz, 1H), 3.05-3.18 (m, 1H), 1.17-1.54 (m, 6H). MS: m/z=419.0 (M+1).

Example 9

Preparation of Compounds Int-9o, Int-9p and Int-9q

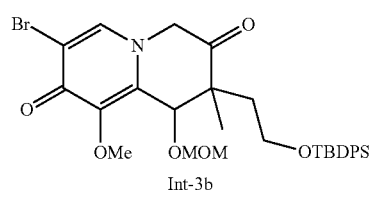
Int-3b

Step A

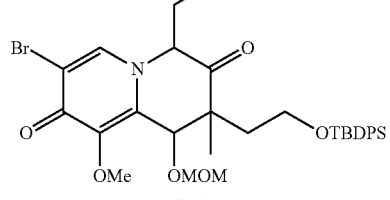
Int-9a

Step B

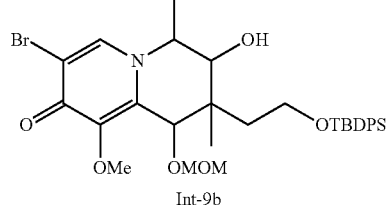
Int-9b

Step C

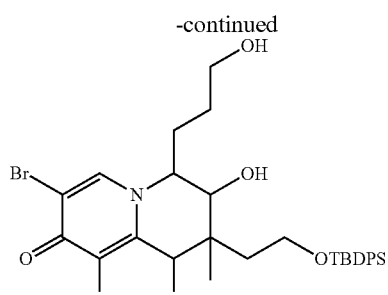
Int-9c

+

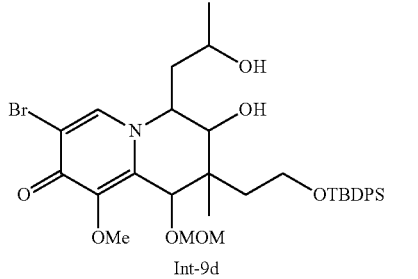
Int-9d

Step D

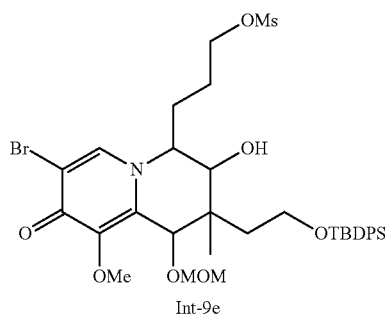
Int-9e

+

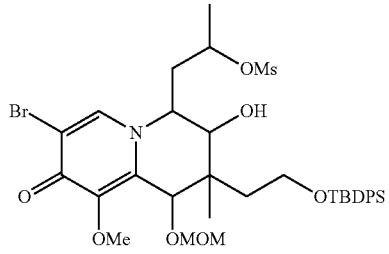
Int-9f

Step E

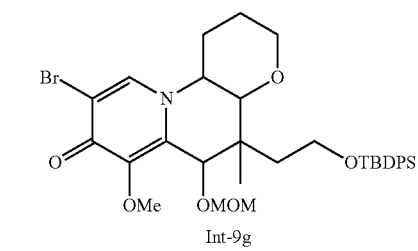
Int-9g

+

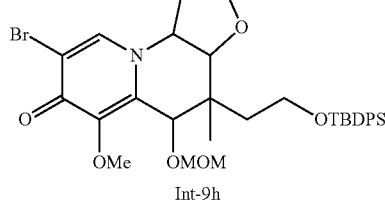
Int-9h

Step F

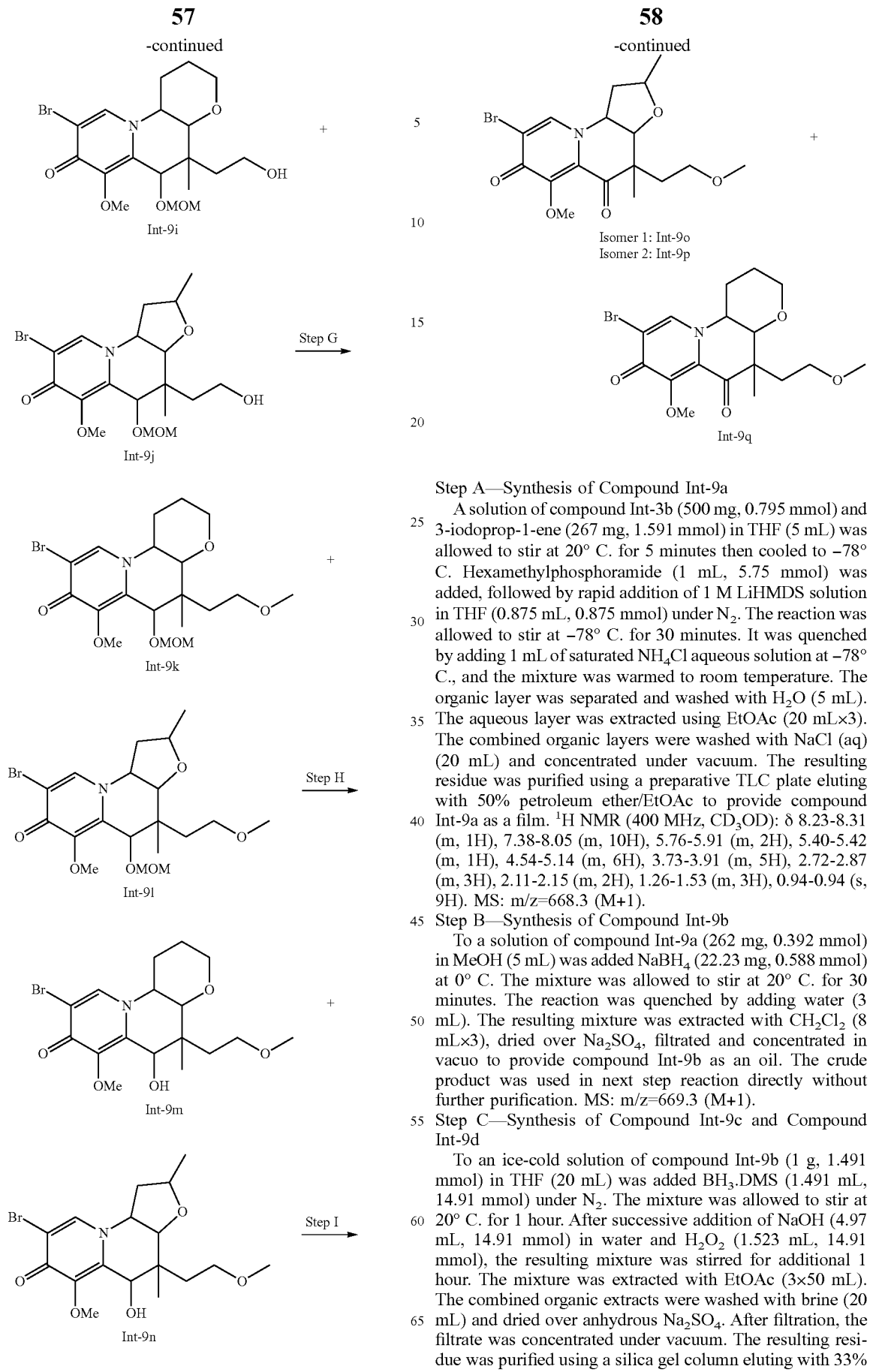

Step A—Synthesis of Compound Int-9a

A solution of compound Int-3b (500 mg, 0.795 mmol) and 3-iodoprop-1-ene (267 mg, 1.591 mmol) in THF (5 mL) was allowed to stir at 20° C. for 5 minutes then cooled to −78° C. Hexamethylphosphoramide (1 mL, 5.75 mmol) was added, followed by rapid addition of 1 M LiHMDS solution in THF (0.875 mL, 0.875 mmol) under $N_2$. The reaction was allowed to stir at −78° C. for 30 minutes. It was quenched by adding 1 mL of saturated $NH_4Cl$ aqueous solution at −78° C., and the mixture was warmed to room temperature. The organic layer was separated and washed with $H_2O$ (5 mL). The aqueous layer was extracted using EtOAc (20 mL×3). The combined organic layers were washed with NaCl (aq) (20 mL) and concentrated under vacuum. The resulting residue was purified using a preparative TLC plate eluting with 50% petroleum ether/EtOAc to provide compound Int-9a as a film. $^1H$ NMR (400 MHz, $CD_3OD$): δ 8.23-8.31 (m, 1H), 7.38-8.05 (m, 10H), 5.76-5.91 (m, 2H), 5.40-5.42 (m, 1H), 4.54-5.14 (m, 6H), 3.73-3.91 (m, 5H), 2.72-2.87 (m, 3H), 2.11-2.15 (m, 2H), 1.26-1.53 (m, 3H), 0.94-0.94 (s, 9H). MS: m/z=668.3 (M+1).

Step B—Synthesis of Compound Int-9b

To a solution of compound Int-9a (262 mg, 0.392 mmol) in MeOH (5 mL) was added $NaBH_4$ (22.23 mg, 0.588 mmol) at 0° C. The mixture was allowed to stir at 20° C. for 30 minutes. The reaction was quenched by adding water (3 mL). The resulting mixture was extracted with $CH_2Cl_2$ (8 mL×3), dried over $Na_2SO_4$, filtrated and concentrated in vacuo to provide compound Int-9b as an oil. The crude product was used in next step reaction directly without further purification. MS: m/z=669.3 (M+1).

Step C—Synthesis of Compound Int-9c and Compound Int-9d

To an ice-cold solution of compound Int-9b (1 g, 1.491 mmol) in THF (20 mL) was added $BH_3.DMS$ (1.491 mL, 14.91 mmol) under $N_2$. The mixture was allowed to stir at 20° C. for 1 hour. After successive addition of NaOH (4.97 mL, 14.91 mmol) in water and $H_2O_2$ (1.523 mL, 14.91 mmol), the resulting mixture was stirred for additional 1 hour. The mixture was extracted with EtOAc (3×50 mL). The combined organic extracts were washed with brine (20 mL) and dried over anhydrous $Na_2SO_4$. After filtration, the filtrate was concentrated under vacuum. The resulting residue was purified using a silica gel column eluting with 33%

EtOAc/petroleum ether to provide a mixture of compound Int-9c and compound Int-9d as an oil. $^1$H NMR (400 MHz, CD$_3$OD): δ 8.29-8.34 (m, 1H), 7.55-7.70 (m, 5H), 7.35-7.43 (m, 5H), 4.52-4.65 (m, 5H), 3.53-3.92 (m, 10H), 2.15-2.31 (m, 5H), 1.26-1.47 (m, 3H), 0.95-0.98 (m, 9H), 0.74-0.77 (m, 2H). MS: m/z=688.3 (M+1).

Step D—Synthesis of Compound Int-9e and Compound Int-9f

To a mixture of compound Int-9c and compound Int-9d (900 mg, 1.31 mmol) in CH$_2$Cl$_2$ (20 mL) stirred at −20° C., was added Et$_3$N (0.546 mL, 3.92 mmol) and methanesulfonyl chloride (225 mg, 1.960 mmol). The reaction was allowed to stir at −20° C. under N$_2$ for 1 hour. It was quenched with water (10 mL). The resulting mixture was extracted with CH$_2$Cl$_2$ (15 mL×3), dried over Na$_2$SO$_4$, filtered and concentrated in vacuo to provide a crude mixture of compound Int-9e and compound Int-9f as a solid. This material was used directly in next reaction without further purification. MS: m/z=767.1 (M+1).

Step E—Synthesis of Compound Int-9g and Compound Int-9h

To a mixture of compound Int-9e and compound Int-9f (800 mg, 1.043 mmol) in DMF (5 mL) was added NaH (83 mg, 2.087 mmol) at 0° C. The mixture was allowed to stir at 19° C. under N$_2$ for 30 minutes. The reaction was quenched with water (6 mL) and the resulting mixture was extracted with EtOAc (10 mL×3), dried over Na$_2$SO$_4$, filtered and concentrated in vacuo The resulting residue was purified using a preparative TLC plate eluting with EtOAc to provide a mixture of compound Int-9g and compound Int-9h as a solid. MS: m/z=672.3 (M+1).

Step F—Synthesis of Compound Int-9i and Compound Int-9j

To a mixture of compound Int-9g and compound Int-9h (200 mg, 0.298 mmol) in THF (2 mL) was added tetrabutylammonium fluoride (0.447 mL, 0.447 mmol). The reaction was allowed to stir at 20° C. for 1.5 hours. The reaction mixture was concentrated under vacuum, and the resulting residue was purified using a preparative TLC plate eluting with EtOAc to provide a mixture of compound Int-9i and compound Int-9j as a solid $^1$H NMR: (400 MHz, CD$_3$OD): δ 8.27-8.32 (m., 1H), 5.42-5.47 (m, 1H), 4.58-4.81 (m, 2H), 4.32-4.40 (m, 1H), 3.65-3.91 (m, 4H), 3.11-3.23 (s, 2H), 1.62-2.01 (m, 4H), 0.74-1.18 (m, 11H). MS: m/z=432.1 (M+1).

Step G—Synthesis of Compound Int-9k and Compound Int-9l

To a mixture of compound Int-9i and compound Int-9j (250 mg, 0.578 mmol) in DMF (5 mL) was added NaH (46.3 mg, 1.157 mmol) and iodomethane (164 mg, 1.157 mmol) at 0° C. The mixture was warmed to 19° C. and stirred for 1 hour. The reaction was quenched by water (5 mL) and the resulting mixture was extracted with EtOAc (10 mL×3), washed with brine (20 mL). The organic layer was dried over Na$_2$SO$_4$, filtered and concentrated in vacuo The resulting residue was purified using a preparative TLC plate eluting with EtOAc to provide a mixture of compound Int-9k and compound Int-9l as a solid. $^1$H NMR: (400 MHz, CD$_3$OD): δ 8.30-8.31 (s, 1H), 4.52-4.73 (m, 4H), 3.85-3.91 (m, 3H), 3.36-3.63 (m, 3H), 3.23-3.35 (m, 6H), 2.00-2.33 (m, 4H), 1.17-1.38 (m, 6H), 0.73 (d, J=16 Hz, 1H). MS: m/z=447.1 (M+1).

Step H—Synthesis of Compound Int-9m and Compound Int-9n

To a mixture of compound Int-9k and compound Int-9l (200 mg, 0.448 mmol) in MeOH (2 mL) was added p-toluenesulfonic acid (170 mg, 0.896 mmol). The mixture was allowed to stir at 35° C. for 16 hours. The reaction was quenched by saturated aqueous NaHCO$_3$ solution. The resulting mixture was filtered, concentrated in vacuo, and the resulting residue was purified using a preparative TLC plate eluting with 7% MeOH/EtOAc to provide a mixture compound Int-9m and compound Int-9n as a solid. $^1$H NMR (400 MHz, CD$_3$OD): δ 8.19-8.34 (m, 1H), 4.29-4.76 (m, 3H), 3.86-3.90 (m, 3H), 3.50-3.65 (m, 3H), 3.22-3.50 (m, 3H), 2.84-2.97 (m, 1H), 2.49-2.50 (m, 1H), 2.05-2.09 (s, 2H), 1.25-1.50 (m, 5H), 0.86 (d, J=16 Hz, 1H). MS: m/z=402.0 (M+1).

Step I—Synthesis of Compound Int-9o, Compound Int-9p and Compound Int-9q

To a solution of a mixture compound Int-9m and compound Int-9n (160 mg, 0.358 mmol) in CH$_2$Cl$_2$ (30 mL) was added Dess Martin periodinane (337 mg, 0.795 mmol). The reaction was allowed to stir at 20° C. for 16 hours. The resulting mixture was filtered and the filtrate was concentrated under vacuum. The resulting residue was purified using a preparative TLC plate eluting with EtOAc to provide compound Int-9o (the first eluting isomer), compound Int-9p (the second eluting isomer), and compound Int-9q (the third eluting isomer) all as solids.

Compound Int-9o: $^1$H NMR (400 MHz, CD$_3$OD): δ 8.37 (m, 1H), 5.07-5.10 (m, 1H), 4.52-4.53 (m, 1H), 3.90-4.05 (m, 1H), 3.84 (m, 3H), 3.54-3.60 (m, 2H), 3.10 (s, 3H), 2.48-2.53 (m, 1H), 2.18-2.22 (m, 1H), 2.01-2.04 (m, 2H), 1.09-1.26 (m, 6H). MS: m/z=400.0 (M+1).

Compound Int-9p: $^1$H NMR (400 MHz, CD$_3$OD): 8.36 (m, 1H), 5.14-5.18 (m, 1H), 4.39-4.40 (m, 1H), 3.85-3.93 (m, 4H), 3.27-3.57 (m, 2H), 3.11 (s, 3H), 2.48-2.49 (m, 1H), 2.44-2.45 (m, 1H), 2.17-2.21 (m, 1H), 2.69-2.70 (m, 1H), 1.07-1.30 (m, 6H). MS: m/z=400.0 (M+1).

Compound Int-9q: $^1$H NMR (400 MHz, CD$_3$OD): δ 8.44 (m, 1H), 4.52-4.67 (m, 1H), 3.83-3.97 (m, 5H), 3.30-3.54 (m, 3H), 3.15-3.32 (m, 3H), 2.74-2.75 (m, 1H), 1.76-2.16 (m, 3H), 1.17-1.43 (m, 5H). MS: m/z=400.0 (M+1).

Example 10

Preparation of Compounds 13 and 14

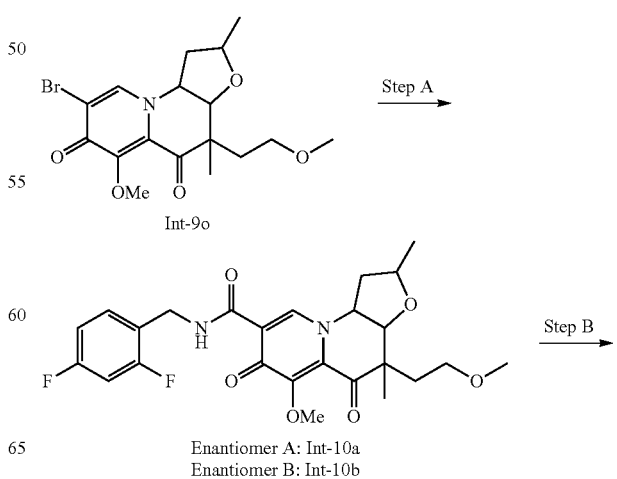

Enantiomer A: Int-10a
Enantiomer B: Int-10b

61
-continued

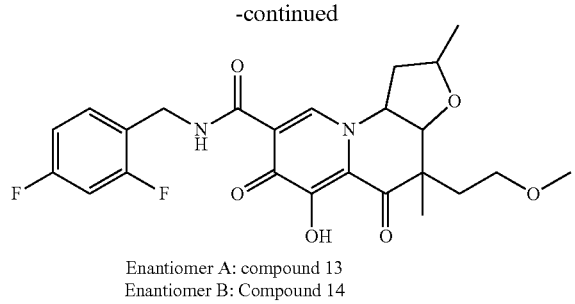

Enantiomer A: compound 13
Enantiomer B: Compound 14

Step A—Synthesis of Compound Int-10a and Compound Int-10b

To a solution of compound Int-9o (16 mg, 0.040 mmol) in DMSO (1 mL) was added diisopropylethylamine (0.014 mL, 0.080 mmol), (2,4-difluorophenyl)methanamine (11.44 mg, 0.080 mmol) and Pd(Ph$_3$P)$_4$ (9.24 mg, 7.99 μmol). The reaction mixture was allowed to stir at 80° C. under a balloon of CO for 6 hours. After cooled to room temperature, the reaction was filtrated and diluted with EtOAc (10 mL). The resulting solution was washed with HCl (0.5 N, 5 mL) and brine (10 mL), dried over Na$_2$SO$_4$, filtrated and concentrated in vacuo The resulting residue was purified using prep-TLC eluting with EtOAc to provide the desired product as racemate. This material was further separated using a chiral preparative SFC (Column: Whelk-01 250 mm*30 mm, 10 um) Mobile phase: 40% Base-IPA (contained 0.1% NH$_3$H$_2$O) in CO$_2$ Flow rate: 60 mL/min Wavelength: 220 nm) to provide compound Int-10a (the first eluting isomer) as a solid and compound Int-10b (the second eluting isomer) as a solid.

Compound 10a: $^1$H NMR (400 MHz, CD$_3$OD): δ 8.51 (m, 1H), 7.32-7.37 (m, 1H), 6.83-6.91 (m, 2H), 5.11-5.13 (m, 1H), 4.48-4.54 (m, 3H), 3.90-4.10 (m, 1H), 3.78 (s, 3H), 3.44-3.54 (m, 2H), 3.44 (s, 3H), 2.42-2.47 (m, 1H), 2.10-2.30 (m, 1H), 1.94-2.18 (m, 2H), 0.81-1.26 (m, 6H).

Compound 10b: $^1$H NMR (400 MHz, CD$_3$OD): δ 8.52 (m, 1H), 7.38-7.44 (m, 1H), 6.89-6.98 (m, 2H), 5.18-5.20 (m, 1H), 4.54-4.65 (m, 3H), 3.90-4.21 (m, 1H), 3.85 (s, 3H), 3.50-3.63 (m, 2H), 3.32 (s, 3H), 2.49-2.54 (m, 1H), 2.10-2.20 (m, 1H), 1.95-2.00 (m, 2H), 0.89-1.13 (m, 6H).

Step B—Synthesis of Compound 13 and Compound 14

To a solution of compound Int-10a (9 mg, 0.018 mmol) in DMF (2 mL) was added lithium chloride (3.11 mg, 0.073 mmol). The mixture was allowed to stir at 80° C. for 12 hours. The mixture was purified using prep-HPLC (Phenomenex Synergi Max-RP 250*50 mm*10 um using TFA, water and acetonitrile as the eluents. Mobile phase A: water (containing 0.1% TFA), mobile phase B: acetonitrile. Gradient: 42%~72% B, 0~8 minutes. Flow Rate: 30 mL/min) to provide compound 13 as a solid. $^1$H NMR (400 MHz, CDCl$_3$): δ 10.35 (s, 1H), 8.48 (m, 1H), 7.31-7.37 (m, 1H), 6.76-6.82 (m, 2H), 4.83 (s, 1H), 4.62-4.63 (m, 2H), 4.52-4.53 (m, 1H), 4.01-4.03 (m, 1H), 3.61-3.63 (m, 2H), 3.32 (s, 3H), 2.52-2.57 (m, 1H), 2.14-2.22 (m, 3H), 1.23-1.25 (m, 6H). MS: m/z=477.1 (M+1).

Compound 14 was prepared using the method described in this Example above, substituting compound Int-10a with compound Int-10b. $^1$H NMR (400 MHz, CDCl$_3$): δ 10.22 (s, 1H), 8.45 (m, 1H), 7.26-7.32 (m, 1H), 6.72-6.77 (m, 2H), 4.79 (s, 1H), 4.57-4.58 (m, 2H), 4.47-4.48 (m, 1H), 3.95-3.98 (m, 1H), 3.56-3.59 (m, 2H), 3.28 (s, 3H), 2.47-2.51 (m, 1H), 2.09-2.17 (m, 3H), 1.18-1.20 (m, 6H). MS: m/z=477.2 (M+1).

62

Example 11

Preparation of Compounds 15 and 16

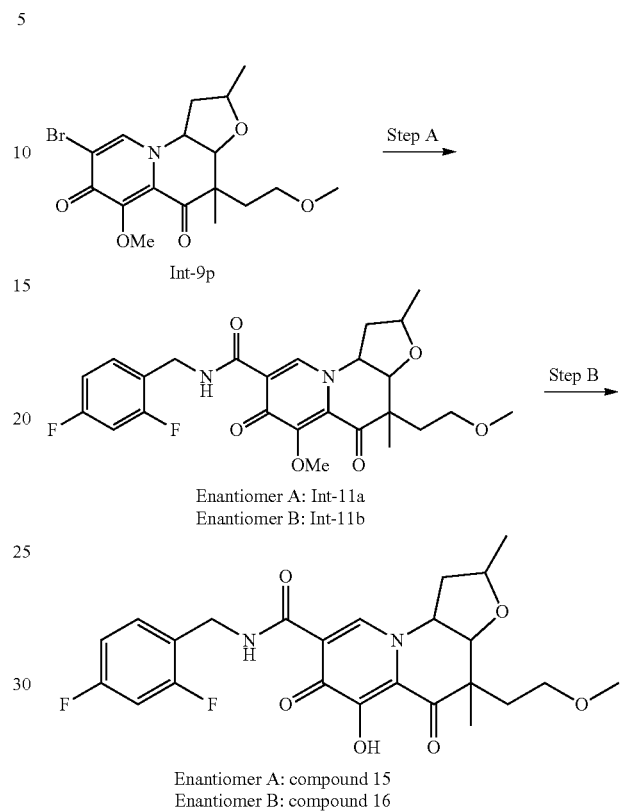

Enantiomer A: Int-11a
Enantiomer B: Int-11b

Enantiomer A: compound 15
Enantiomer B: compound 16

Step A—Synthesis of Compound Int-11a and Compound Int-11b

To compound Int-9p (20 mg, 0.050 mmol) in DMSO (1 mL) was added diisopropylethylamine (0.017 mL, 0.100 mmol), (2,4-difluorophenyl)methanamine (14.30 mg, 0.100 mmol) and Pd(Ph$_3$P)$_4$ (11.55 mg, 9.99 μmol). The reaction mixture was allowed to stir at 80° C. under a balloon of CO for 6 hours. After cooled to room temperature, the mixture was filtered and diluted with EtOAc (10 mL). The resulting solution was washed with HCl (0.5 N, 5 mL) and brine (10 mL), dried over Na$_2$SO$_4$, filtrated and concentrated in vacuo The resulting residue was purified using a preparative TLC plate eluting with EtOAc to provide the desired product as a racemate. $^1$H NMR (400 MHz, CD$_3$OD): δ 8.56 (m, 1H), 7.39-7.45 (m, 1H), 6.90-6.97 (m, 2H), 5.25-5.28 (m, 1H), 4.59-4.65 (m, 2H), 4.41-4.42 (m, 1H), 3.87-4.00 (m, 4H), 3.31-3.36 (m, 2H), 3.10 (s, 3H), 2.41-2.50 (m, 1H), 2.20-2.30 (m, 1H), 1.80-1.90 (m, 1H), 1.60-1.70 (m, 1H), 1.18-1.35 (m, 6H). MS: m/z=491.2 (M+1).

This material was further separated using a chiral preparative SFC (Column: Whelk-01 250 mm*30 mm, 10 um) Mobile phase: 40% Base-IPA (contained 0.1% NH$_4$OH) in CO$_2$ Flow rate: 60 mL/min Wavelength: 220 nm) to provide compound Int-11a (the first eluting isomer) as a solid and compound Int-11b (the second eluting isomer) as a solid.

Step B—Synthesis of Compound 15 and Compound 16

To a solution of compound Int-11a (8 mg, 0.016 mmol) in DMF (2 mL) was added lithium chloride (2.77 mg, 0.065 mmol). The reaction was heated and stirred at 80° C. for 12 hours. The mixture was cooled to room temperature and purified using prep-HPLC (Phenomenex Synergi Max-RP 250 mm*50 mm*10 um using TFA, water and acetonitrile as the eluents. Mobile phase A: water (containing 0.1% TFA), mobile phase B: acetonitrile. Gradient: 42%~72% B, 0~8 minutes. Flow Rate: 30 mL/min) to provide compound 15 as a solid. $^1$H NMR (400 MHz, CDCl$_3$): δ 10.42 (s, 1H), 8.49 (m, 1H), 7.33-7.39 (m, 1H), 6.78-6.84 (m, 2H), 4.99 (m, 1H), 4.63-4.65 (m, 2H), 3.96 (br., 1H), 3.39-3.40 (m, 1H), 3.44-3.46 (m, 1H), 3.30-3.33 (m, 1H), 3.16 (s, 3H), 2.48-2.53 (m, 1H), 2.19-2.23 (s, 1H), 1.76-1.83 (m, 2H), 1.42-1.43 (m, 3H), 1.23-1.25 (m, 3H). MS: m/z=477.2 (M+1).

Compound 16 was prepared using the method described in this Example above, substituting compound Int-11a with compound Int-11b. $^1$H NMR (400 MHz, CDCl$_3$): δ 10.39 (s, 1H), 8.47 (m, 1H), 7.33-7.37 (m, 1H), 6.77-6.82 (m, 2H), 4.99-5.00 (m, 1H), 4.63-4.65 (m, 2H), 4.39-4.40 (m, 1H), 3.96-4.00 (m, 1H), 3.46-3.47 (m, 1H), 3.30-3.33 (m, 1H), 3.16 (s, 3H), 2.48-2.53 (m, 1H), 2.19-2.20 (m, 1H), 1.83-1.85 (m, 2H), 1.42-1.43 (m, 3H), 1.23-1.25 (m, 3H). MS: m/z=477.2 (M+1).

Example 12

Preparation of Compounds 17-20

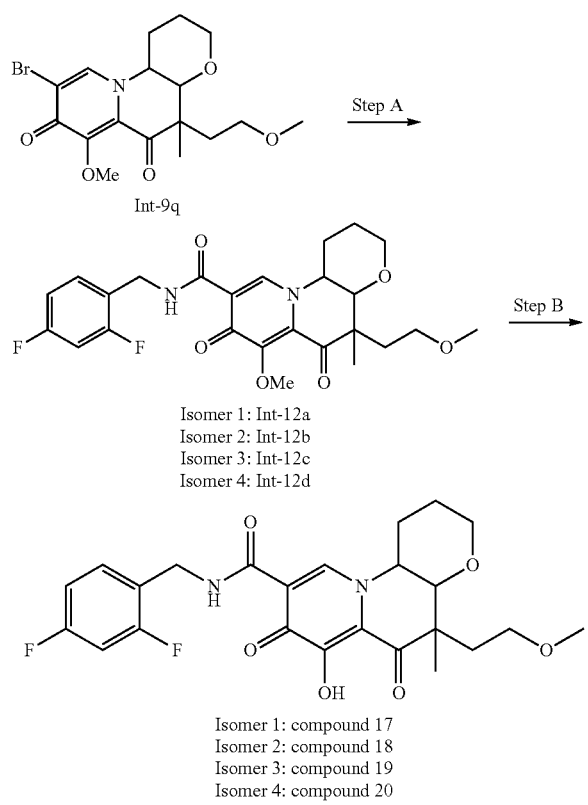

Isomer 1: Int-12a
Isomer 2: Int-12b
Isomer 3: Int-12c
Isomer 4: Int-12d

Isomer 1: compound 17
Isomer 2: compound 18
Isomer 3: compound 19
Isomer 4: compound 20

Step A—Synthesis of Compound Int-12a,b,c,d

To compound Int-9q (20 mg, 0.050 mmol) in DMSO (1 mL) was added diisopropylethylamine (0.017 mL, 0.100 mmol), (2,4-difluorophenyl)methanamine (14.30 mg, 0.100 mmol) and Pd(Ph$_3$P)$_4$ (11.55 mg, 9.99 μmol). The reaction was allowed to stir at 80° C. under a balloon of CO for 6 hours. After the reaction mixture was cooled to room temperature, it was filtered and diluted with EtOAc (10 mL). The resulting solution was washed with HCl (0.5 N, 5 mL) and brine (10 mL), dried over Na$_2$SO$_4$, filtrated and concentrated in vacuo The resulting residue was purified using a preparative TLC plate eluting with EtOAc to provide the desired product as a mixture of stereoisomers. This material was further purified using a chiral preparative SFC (Column: Whelk-01 250 mm*30 mm, 10 um) Mobile phase: 40% Base-IPA (contained 0.1% NH$_3$H$_2$O) in CO$_2$ Flow rate: 60 mL/min Wavelength: 220 nm) to provide individually compound Int-12a (the first eluting isomer), compound Int-12b (the second eluting isomer), and a fraction containing a mixture of two additional stereoisomers which was further separated using a chiral preparative SFC (Column: C2 250 mm*30 mm, 10 um) Mobile phase: 50% Base-EtOH (contained 0.1% NH$_3$H$_2$O) in CO$_2$ Flow rate: 60 mL/min Wavelength: 220 nm) to provide compound Int-12c (the first eluting isomer) and compound Int-12d (the second eluting isomer).

Compound Int-12a: $^1$H NMR (400 MHz, CD$_3$OD): δ 8.64 (s, 1H), 7.39-7.45 (m, 1H), 6.90-6.98 (m, 2H), 4.59-4.66 (m, 3H), 4.19-4.00 (m, 2H), 3.85 (s, 3H), 3.46-3.60 (m, 3H), 3.35 (s, 3H), 2.76-2.82 (m, 1H), 2.09-2.25 (m, 2H), 1.89-1.93 (m, 1H), 1.19-1.45 (m, 5H).

Compound Int-12b: $^1$H NMR (400 MHz, CD$_3$OD): δ 8.63 (s, 1H), 7.39-7.45 (m, 1H), 6.90-6.98 (m, 2H), 4.59-4.66 (m, 3H), 4.19-4.00 (m, 2H), 3.84 (s, 3H), 3.46-3.60 (m, 3H), 3.35 (s, 3H), 2.76-2.80 (m, 1H), 2.09-2.25 (m, 2H), 1.89-1.93 (m, 1H), 1.19-1.45 (m, 5H).

Compound Int-12c: $^1$H NMR (400 MHz, CD$_3$OD): δ 8.69 (s, 1H), 7.37-7.47 (m, 1H), 6.92-6.99 (m, 2H), 4.60-4.76 (m, 3H), 3.92-3.93 (m, 2H), 3.86 (s, 3H), 3.36-3.56 (m, 3H), 3.16 (s, 3H), 2.75-2.78 (m, 1H), 2.14-2.15 (m, 1H), 2.78-2.86 (m, 2H), 1.26-1.48 (m, 2H), 1.28 (s, 3H).

Compound Int-12d: $^1$H NMR (400 MHz, CD$_3$OD): δ 8.69 (s, 1H), 7.37-7.47 (m, 1H), 6.92-6.99 (m, 2H), 4.61-4.67 (m, 2H), 4.00-4.06 (m, 1H), 3.85-3.95 (m, 3H), 3.85 (s, 3H), 3.50-3.60 (m, 3H), 3.40 (s, 3H), 2.78-2.82 (m, 1H), 2.11-2.16 (m, 1H), 2.05-2.24 (m, 1H), 1.30-1.95 (m, 3H), 1.20 (s, 3H).

Step B—Synthesis of Compound 17-20

To a solution of compound Int-12a (10 mg, 0.020 mmol) in DMF (2 mL) was added lithium chloride (3.46 mg, 0.082 mmol). The reaction was allowed to stir at 80° C. for 12 hours. The resulting mixture was cooled to room temperature and purified using prep-HPLC (Phenomenex Synergi Max-RP 250 mm*50 mm*10 um using TFA water and acetonitrile as the eluents. Mobile phase A: water (containing 0.1% TFA), mobile phase B: acetonitrile. Gradient: 42%~72% B, 0~8 minutes. Flow Rate: 30 mL/min) to provide compound 17 as a solid. $^1$H NMR (400 MHz, CDCl$_3$): δ 10.52 (s, 1H), 8.62 (m, 1H), 7.33-7.39 (m, 1H), 6.78-6.84 (m, 2H), 4.64-4.66 (m, 3H), 3.84-3.99 (m, 2H), 3.50-3.55 (m, 2H), 3.38-3.40 (m, 1H), 3.23 (s, 3H), 2.76-2.80 (m, 1H), 2.04-2.05 (m, 1H), 1.83-1.85 (m, 1H), 1.68-1.69 (m, 1H), 1.37-1.45 (m, 5H). MS: m/z=477.1 (M+1).

Compound 18 was prepared using the method described in this Example above, substituting compound Int-12a with compound Int-12b. $^1$H NMR (400 MHz, CDCl$_3$): δ 10.39 (s, 1H), 8.56 (s, 1H), 7.27-7.33 (m, 1H), 6.71-6.77 (m, 2H), 4.57-4.59 (m, 2H), 4.31 (s, 1H), 3.92-3.93 (m, 2H), 3.46-3.54 (m, 3H), 3.28 (s, 3H), 2.72-2.74 (m, 1H), 2.16-2.17 (s, 1H), 1.97-2.03 (m, 2H), 1.20-1.22 (m, 2H), 1.18 (m, 3H). MS: m/z=477.1 (M+1).

Compound 19 was prepared using the method described in this Example above, substituting compound Int-12a with compound Int-12c. $^1$H NMR (400 MHz, CDCl$_3$): δ 10.61 (s, 1H), 8.62-8.65 (m, 1H), 7.33-7.39 (m, 1H), 6.78-6.84 (m, 2H), 4.64-4.66 (m, 3H), 3.84-3.99 (m, 2H), 3.50-3.55 (m, 2H), 3.38-3.40 (m, 1H), 3.23 (s, 3H), 2.76-2.80 (m, 1H), 2.04-2.05 (s, 1H), 1.83-1.85 (m, 1H), 1.67-1.68 (m, 1H), 1.37-1.45 (m, 5H). MS: m/z=477.1 (M+1).

Compound 20 was prepared using the method described in this Example above, substituting compound Int-12a with compound Int-12d. $^1$H NMR (400 MHz, CDCl$_3$): δ 10.46 (s, 1H), 8.61 (s, 1H), 7.32-7.37 (m, 1H), 6.76-6.82 (m, 2H), 4.62-4.64 (m, 2H), 4.36-4.37 (m, 1H), 3.97-3.98 (m, 2H), 3.50-3.59 (m, 3H), 3.33 (s, 3H), 2.72-2.74 (m, 1H), 2.05-2.24 (s, 3H), 1.41-1.45 (m, 2H), 1.25 (m, 3H). MS: m/z=477.1 (M+1).

Example 13

Assay for Inhibition of HIV Replication

This assay is a kinetic assay that employs a reporter cell line (MT4-gag-GFP) to quantify the number of new cells infected in each round of replication.

MT4-GFP cells (250,000 cells/ml) were bulk-infected with HIV-1 (NL4-3 strain) at low multiplicity of infection (MOI) in RPMI+10% FBS for 24 hours. Cells were then washed once in RPMI+10% FBS and resuspended in RPMI+0% or 10% or 100% normal human serum (NHS). Test compounds were serial-diluted in DMSO on ECHO. The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen eX3. Viral reproductive ratio ($R_0$) was determined using the number of infected cells at 48 hours divided by the number of infected cells at 24 hours. Percent viral growth inhibition was calculated by $[1-(R-R_{tripledrug})/(R_{DMSO}-R_{tripledrug})]*100$. Compound potency IP or IC$_{50}$ was determined by a 4-parameter dose response curve analysis.

Illustrative compounds of the present invention were tested using this assay protocol and results are presented below in Table A.

TABLE A

| Compound No. | WILD TYPE CELL ASSAY Viking IP (0% NHS) (nM) | WILD TYPE CELL ASSAY Viking IP (100% NHS) (nM) |
|---|---|---|
| 1 | N/A | 400 |
| 2 | N/A | 385 |
| 3 | N/A | 58 |
| 4 | 8.0 | 17 |
| 5 | 1.3 | 132 |
| 6 | 4.5 | >8000 |
| 7 | 1.7 | >8000 |
| 8 | 6.0 | 683 |
| 9 | 5.3 | 174 |
| 10 | 1.7 | 50 |
| 11 | 1.1 | 1900 |
| 12 | 1.1 | 303 |
| 13 | 2.9 | 69 |
| 14 | 15 | 825 |
| 15 | 10 | 238 |
| 16 | 33 | 1133 |
| 17 | 3.3 | 90 |
| 18 | 2.2 | 72 |
| 19 | 4.1 | 120 |
| 20 | 2.2 | 1031 |

N/A = Not Available

Uses of the Fused Tricyclic Heterocycle Derivatives

The Fused Tricyclic Heterocycle Derivatives may be useful in human and veterinary medicine for treating or preventing HIV infection in a subject. In one embodiment, the Fused Tricyclic Heterocycle Derivatives can be inhibitors of HIV viral replication. In a specific embodiment, the Fused Tricyclic Heterocycle Derivatives are inhibitors of HIV-1. Accordingly, the Fused Tricyclic Heterocycle Derivatives may be useful for treating HIV infections and AIDS. In accordance with the invention, the Fused Tricyclic Heterocycle Derivatives can be administered to a subject in need of treatment or prevention of HIV infection.

Accordingly, in one embodiment, the invention provides methods for treating HIV infection in a subject comprising administering to the subject an effective amount of at least one Fused Tricyclic Heterocycle Derivative or a pharmaceutically acceptable salt thereof. In a specific embodiment, the present invention provides methods for treating AIDS in a subject comprising administering to the subject an effective amount of at least one Fused Tricyclic Heterocycle Derivative or a pharmaceutically acceptable salt thereof.

Treatment or Prevention of HIV Infection

The Fused Tricyclic Heterocycle Derivatives may be useful in the inhibition of HIV, the treatment of HIV infection and/or reduction of the likelihood or severity of symptoms of HIV infection and the inhibition of HIV viral replication and/or HIV viral production in a cell-based system. For example, the Fused Tricyclic Heterocycle Derivatives may be useful in treating infection by HIV after suspected past exposure to HIV by such means as blood transfusion, exchange of body fluids, bites, accidental needle stick, or exposure to subject blood during surgery or other medical procedures.

In one embodiment, the HIV infection has progressed to AIDS.

Accordingly, in one embodiment, the invention provides methods for treating HIV infection in a subject, the methods comprising administering to the subject an effective amount of at least one Fused Tricyclic Heterocycle Derivative or a pharmaceutically acceptable salt thereof. In a specific embodiment, the amount administered is effective to treat or prevent infection by HIV in the subject. In another specific embodiment, the amount administered is effective to inhibit HIV viral replication and/or viral production in the subject.

The Fused Tricyclic Heterocycle Derivatives may also be useful in the preparation and execution of screening assays for antiviral compounds. For example the Fused Tricyclic Heterocycle Derivatives may be useful for identifying resistant HIV cell lines harboring mutations, which are excellent screening tools for more powerful antiviral compounds. Furthermore, the Fused Tricyclic Heterocycle Derivatives may be useful in establishing or determining the binding site of other antivirals to the HIV Integrase.

Combination Therapy

In another embodiment, the present methods for treating or preventing HIV infection can further comprise the administration of one or more additional therapeutic agents which are not Fused Tricyclic Heterocycle Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Fused Tricyclic Heterocycle Derivative (which may include two or more different Fused Tricyclic Heterocycle Derivatives), or a pharmaceutically acceptable salt thereof, and (ii) at least one additional therapeutic agent that is other than a Fused Tricyclic Heterocycle Derivative, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Fused Tricyclic Heterocycle Derivative and an additional therapeutic agent may be present in fixed amounts (dosage amounts) in a single dosage unit (e.g., a capsule, a tablet and the like).

In one embodiment, the at least one Fused Tricyclic Heterocycle Derivative is administered during a time when the additional therapeutic agent(s) exert their prophylactic or therapeutic effect, or vice versa.

In another embodiment, the at least one Fused Tricyclic Heterocycle Derivative and the additional therapeutic agent(s) are administered in doses commonly employed when such agents are used as monotherapy for treating a viral infection.

In another embodiment, the at least one Fused Tricyclic Heterocycle Derivative and the additional therapeutic agent(s) are administered in doses lower than the doses commonly employed when such agents are used as monotherapy for treating a viral infection.

In still another embodiment, the at least one Fused Tricyclic Heterocycle Derivative and the additional therapeutic agent(s) act synergistically and are administered in doses lower than the doses commonly employed when such agents are used as monotherapy for treating a viral infection.

In one embodiment, the at least one Fused Tricyclic Heterocycle Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the viral infection is AIDS.

The at least one Fused Tricyclic Heterocycle Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Fused Tricyclic Heterocycle Derivative and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| CMX-157 | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| Rilpivirine + emtricitabine + tenofovir, Complera | nnRTI + nRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, darunavir, atazanavir, emtricitabine, tenofovir, elvitegravir, rilpivirine and lopinavir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In another embodiment, the compound of formula (I) is used in combination with a single anti-HIV drug which is rilpivirine.

In one embodiment, the compound of formula (I) is used in combination with two anti-HIV drugs which are lamivudine and abacavir.

In another embodiment, the compound of formula (I) is used in combination with two anti-HIV drugs which are emtricitabine and tenofovir.

In another embodiment, the compound of formula (I) is used in combination with two anti-HIV drugs which are ritonavir and lopinavir.

In one embodiment, the present invention provides pharmaceutical compositions comprising (i) a compound of formula (I) or a pharmaceutically acceptable salt thereof; (ii) a pharmaceutically acceptable carrier; and (iii) one or more additional anti-HIV agents selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV agents selected from lamivudine, abacavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and the like. The dosage ranges for a compound of the invention in these combinations are the same as those set forth above.

The compounds of this invention may also be useful in the preparation and execution of screening assays for antiviral compounds. For example, the compounds of this invention are useful for isolating enzyme mutants, which are excellent screening tools for more powerful antiviral compounds.

Furthermore, the compounds of this invention are useful in establishing or determining the binding site of other antivirals to HIV integrase, e.g., by competitive inhibition. Thus the compounds of this invention are commercial products to be sold for these purposes.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Fused Tricyclic Heterocycle Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Fused Tricyclic Heterocycle Derivatives can be administered as a component of a composition that comprises a pharmaceutically acceptable carrier or vehicle. The present invention provides pharmaceutical compositions comprising an effective amount of at least one Fused Tricyclic Heterocycle Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Fused Tricyclic Heterocycle Derivatives are administered orally.

In another embodiment, the one or more Fused Tricyclic Heterocycle Derivatives are administered intravenously.

In one embodiment, a pharmaceutical preparation comprising at least one Fused Tricyclic Heterocycle Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tricyclic Heterocycle Derivative(s) by weight or volume. In various embodiments, the present compositions can contain, in one embodiment, from about 1% to about 70% or from about 5% to about 60% of the Fused Tricyclic Heterocycle Derivative(s) by weight or volume.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Fused Tricyclic Heterocycle Derivatives will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) at least one Fused Tricyclic Heterocycle Derivative or a pharmaceutically acceptable salt thereof; (ii) one or more additional therapeutic agents that are not a Fused Tricyclic Heterocycle Derivative; and (iii) a pharmaceutically acceptable carrier, wherein the amounts in the composition are together effective to treat HIV infection.

Kits

In one aspect, the present invention provides a kit comprising a therapeutically effective amount of at least one Fused Tricyclic Heterocycle Derivative, or a pharmaceutically acceptable salt or prodrug of said compound and a pharmaceutically acceptable carrier, vehicle or diluent.

In another aspect the present invention provides a kit comprising an amount of at least one Fused Tricyclic Heterocycle Derivative, or a pharmaceutically acceptable salt or prodrug of said compound and an amount of at least one additional therapeutic agent listed above, wherein the amounts of the two or more active ingredients result in a desired therapeutic effect. In one embodiment, the one or more Fused Tricyclic Heterocycle Derivatives and the one or more additional therapeutic agents are provided in the same container. In one embodiment, the one or more Fused Tricyclic Heterocycle Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

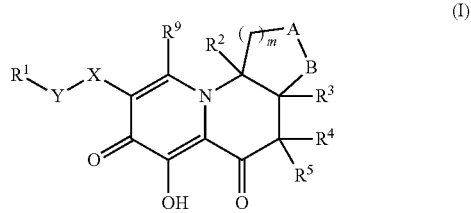

or a pharmaceutically acceptable salt thereof, wherein:
the group -A-B— is selected from —O—C($R^{13}$)$_2$—, —O—C($R^{13}$)$_2$—C($R^{13}$)$_2$—, —C($R^{13}$)$_2$—O—, —N($R^{14}$)—C($R^{13}$)$_2$—, —N($R^{14}$)—C($R^{13}$)$_2$—C($R^{13}$)$_2$— and —C($R^{13}$)$_2$—N($R^{14}$)—;

X is selected from a single bond, 5 or 6-membered monocyclic heteroaryl and —N($R^6$)C(O)—;

Y is a single bond or $C_1$-$C_3$ alkylene;

$R^1$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can each be optionally substituted with up to three $R^8$ groups;

$R^2$ is selected from H, $C_1$-$C_6$ alkyl, —($C_1$-$C_6$ alkylene)$_m$—Z—$R^{16}$, —N($R^{25}$)$_2$, —N($R^{11}$)$_2$ and —O$R^7$;

$R^3$ is selected from H, $C_1$-$C_6$ alkyl, —($C_1$-$C_6$ alkylene)$_m$—Z—$R^{16}$, —N($R^{25}$)$_2$, —N($R^{11}$)$_2$ and —O$R^7$;

$R^4$ is selected from H, $C_1$-$C_6$ alkyl, $C_1$-$C_6$ haloalkyl, $C_2$-$C_6$ alkenyl, —($C_1$-$C_6$alkylene)—O—($C_1$-$C_6$ alkyl), —($C_1$-$C_6$ alkylene)$_m$—Z—$R^{16}$, —N($R^{25}$)$_2$, —N($R^{11}$)$_2$ and —O$R^7$, or $R^4$ and $R^5$ and the common carbon atom to which they are attached, join to form an exocyclic olefin group having the formula:

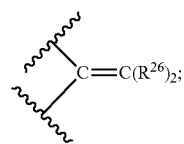

$R^5$ is selected from H, $C_1$-$C_6$ alkyl, $C_2$-$C_6$ alkenyl, —($C_1$-$C_6$ alkylene)—O—($C_1$-$C_6$ alkyl), —N($R^{11}$)$_2$ and —O$R^7$;

each occurrence of $R^6$ is independently selected from H, $C_1$-$C_6$ alkyl, —($C_1$-$C_6$ alkylene)$_m$—Z—$R^{16}$ and —N($R^{25}$)$_2$;

each occurrence of $R^7$ is independently selected from H, $C_1$-$C_6$ alkyl, —($C_1$-$C_6$ alkylene)—O—($C_1$-$C_6$ alkyl) and $C_3$-$C_7$ cycloalkyl;

each occurrence of $R^8$ is independently selected from $C_1$-$C_6$ alkyl, halo, —O$R^{15}$, —S$R^{15}$, $C_1$-$C_6$ haloalkyl, $C_1$-$C_6$ hydroxyalkyl, —O—($C_1$-$C_6$ haloalkyl), —CN, —NO$_2$, —N($R^{15}$)$_2$, $R^{16}$, —C(O)O$R^7$, —C(O)N($R^7$)$_2$ and —NHC(O)$R^7$;

$R^9$ is selected from H, $C_1$-$C_6$ alkyl, —($C_1$-$C_6$ alkylene)—O—$C_1$-$C_6$ alkyl, —($C_1$-$C_6$ alkylene)—N($R^{15}$)—$C_1$-$C_6$ alkyl, —$C_1$-$C_6$ haloalkyl, —$C_1$-$C_6$ hydroxyalkyl;

each occurence of $R^{10}$ is independently selected from H and $C_1$-$C_6$ alkyl;

each occurrence of $R^{11}$ is independently selected from H, $C_1$-$C_6$ alkyl, —S(O)$_2R^{12}$ and —C(O)$R^{12}$;

each occurrence of $R^{12}$ is independently selected from H, $C_1$-$C_6$ alkyl, $C_3$-$C_7$ cycloalkyl, $C_6$-$C_{10}$ aryl, 4 to 7-membered monocyclic heterocycloalkyl, 8 to 11-membered bicyclic heterocycloalkyl, 5 or 6-membered monocyclic heteroaryl and 9 or 10-membered bicyclic heteroaryl, wherein said $C_3$-$C_7$ cycloalkyl group, said $C_6$-$C_{10}$ aryl group, said 4 to 7-membered monocyclic heterocycloalkyl, said 8 to 11-membered bicyclic heterocycloalkyl group, said 5 or 6-membered monocyclic heteroaryl group and said 9 or 10-membered bicyclic heteroaryl group can each be optionally substituted with up to three $R^8$ groups;

each occurrence of $R^{13}$ is independently selected from H, $C_1$-$C_6$ alkyl, $C_3$-$C_7$ cycloalkyl, halo, $C_1$-$C_6$ haloalkyl, —($C_1$-$C_6$ alkylene)$_m$—Z—$R^{16}$, —N($R^{25}$)$_2$, —C(O)$R^{15}$, —C(O)N($R^{15}$)$_2$ and —NHC(O)$R^{15}$;

each occurrence of $R^{14}$ is independently selected from H, $C_1$-$C_6$ alkyl, —($C_1$-$C_6$ alkylene)$_m$—Z—$R^{16}$, $C_3$-$C_7$ cycloalkyl and $C_6$-$C_{10}$ aryl, wherein said $C_3$-$C_7$ cycloalkyl group and said $C_6$-$C_{10}$ aryl group can be optionally substituted with one or more groups, each independently selected from $C_1$-$C_6$ alkyl, $C_3$-$C_7$ cycloalkyl, $C_6$-$C_{10}$ aryl, halo, $C_1$-$C_6$ haloalkyl, —C(O)$R^{15}$, —C(O)O$R^{15}$, —C(O)N($R^{15}$)$_2$, —NHC(O)$R^{15}$ and —S(O)$_2R^{15}$;

each occurrence of $R^{15}$ is independently selected from H, $C_1$-$C_6$ alkyl, $C_3$-$C_7$ cycloalkyl, $C_6$-$C_{10}$ aryl and benzyl; and each occurrence of $R^{16}$ is independently selected from —P(O)(—O$R^{24}$)$_2$,

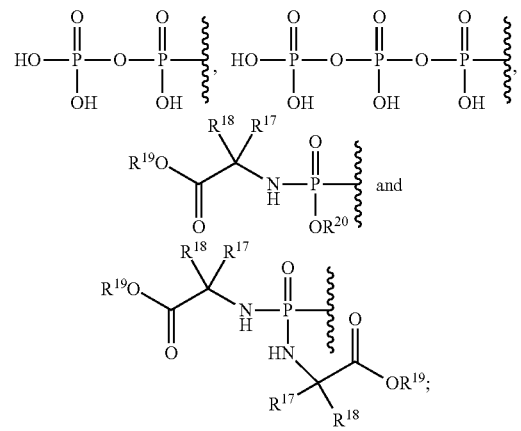

each occurrence of $R^{17}$ is independently selected from H, $C_1$-$C_6$ alkyl, $C_3$-$C_7$ cycloalkyl, phenyl and benzyl, wherein said $C_1$-$C_6$ alkyl can be optionally substituted with a group selected from halo, —O$R^{21}$, —S$R^{21}$, guanidino, —N($R^{21}$)$_2$, —C(O)O$R^{21}$, —C(O)N($R^{21}$)$_2$, —NHC(O)$R^{21}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —O$R^{26}$;

each occurrence of $R^{18}$ is independently selected from H, $C_1$-$C_6$ alkyl, $C_3$-$C_7$ cycloalkyl, phenyl and benzyl, wherein said $C_1$-$C_6$ alkyl can be optionally substituted with a group selected from halo, —O$R^{21}$, —S$R^{21}$, guanidino, —N($R^{21}$)$_2$, —C(O)O$R^{21}$, —C(O)N($R^{21}$)$_2$, —NHC(O)$R^{21}$, 5- or 6-membered monocyclic heteroaryl and 9- or 10-membered bicyclic heteroaryl, and wherein said phenyl group and said benzyl group can be optionally substituted with up to 2 groups, each independently selected from $C_1$-$C_6$ alkyl, halo and —O$R^{21}$;

each occurrence of $R^{19}$ is independently selected from H, $C_1$-$C_{20}$ alkyl, $C_2$-$C_{20}$ alkenyl, —($C_1$-$C_3$ alkylene)$_m$—($C_3$-$C_7$ cycloalkyl), —($C_1$-$C_3$ alkylene)$_m$—($C_6$-$C_{10}$ aryl) and —($C_1$-$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group can be optionally substituted with up to three groups, each independently selected from halo, —OR$^{21}$, —C(O)OR$^{21}$, —CN, —NO$_2$, C$_1$-C$_6$ haloalkyl, C$_1$-C$_6$ hydroxyalkyl, C$_3$-C$_7$ cycloalkyl, C$_6$-C$_{10}$ aryl, 5- or 6-membered monocyclic heteroaryl, 9- or 10-membered bicyclic heteroaryl, —N(R$^{21}$)$_2$, —C(O)N(R$^{21}$)$_2$, —SR$^{21}$, —S(O)R$^{21}$, —S(O)$_2$R$^{21}$, —S(O)$_2$N(R$^{21}$)$_2$, —NHC(O)R$^{21}$, —NHC(O)OR$^{21}$ and —NHC(O)N(R$^{21}$)$_2$;

each occurrence of R$^{20}$ is independently selected from H, C$_6$-C$_{10}$ aryl, 5- or 6-membered monocyclic heteroaryl and 9- or 10-membered bicyclic heteroaryl, wherein said C$_6$-C$_{10}$ aryl group, said 5- or 6-membered monocyclic heteroaryl group and said 9- or 10-membered bicyclic heteroaryl group can be optionally substituted with up to five R$^{22}$ groups;

each occurrence of R$^{21}$ is independently H, C$_1$-C$_{10}$ alkyl, C$_1$-C$_6$ haloalkyl, C$_1$-C$_6$ hydroxyalkyl, —(C$_1$-C$_3$ alkylene)$_m$—(C$_3$-C$_7$ cycloalkyl), —(C$_1$-C$_3$ alkylene)$_m$—(C$_6$-C$_{10}$ aryl), —(C$_1$-C$_3$ alkylene)$_m$—(4 to 7-membered heterocycloalkyl), —(C$_1$-C$_3$ alkylene)$_m$—(5- or 6-membered monocyclic heteroaryl) or —(C$_1$-C$_3$ alkylene)$_m$—(9- or 10-membered bicyclic heteroaryl), wherein said C$_3$-C$_7$ cycloalkyl group, said C$_6$-C$_{10}$ aryl group, said 4 to 7-membered heterocycloalkyl group, said -5- or 6-membered monocyclic heteroaryl group or said 9- or 10-membered bicyclic heteroaryl group can be optionally substituted with up to five R$^{22}$ groups;

each occurrence of R$^{22}$ is independently selected from C$_1$-C$_6$ alkyl, halo, —OR$^{21}$, —SR$^{21}$, C$_1$-C$_6$ haloalkyl, C$_1$-C$_6$ hydroxyalkyl, —O—(C$_1$-C$_6$ haloalkyl), —CN, —NO$_2$, —N(R$^{21}$)$_2$, —C(O)OR$^{21}$, —C(O)N(R$^{21}$)$_2$ and —NHC(O)R$^{21}$, or any two R$^{22}$ groups on adjacent ring carbon atoms can combine to form —O—R$^{23}$—O—;

R$^{23}$ is —[C(R$^{10}$)$_2$]$_n$—;

each occurence of R$^{24}$ is independently selected from H, C$_1$-C$_6$ alkyl, C$_6$-C$_{10}$ aryl, —(C$_1$-C$_6$ alkylene)—O—(C$_1$-C$_{20}$ alkyl), —(C$_1$-C$_6$ alkylene)—O—C(O)—R$^{21}$, and —(C$_1$-C$_6$ alkylene)—O—C(O)O—R$^{21}$;

each occurence of R$^{25}$ is independently selected from H, C$_1$-C$_6$ alkyl and —(C$_1$-C$_6$ alkylene)—Z—R$^{16}$;

each occurrence of Z is independently —O—or a bond;

each occurrence of m is independently 0, 1 or 2; and n is 1 or 2.

2. The compound of claim 1, wherein X is —NHC(O)—, or a pharmaceutically acceptable salt thereof.

3. The compound of claim 1, wherein X is 5 or 6-membered monocyclic heteroaryl, or a pharmaceutically acceptable salt thereof.

4. The compound of claim 3, wherein X is:

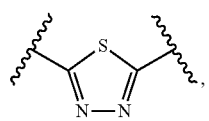 [SMILES: *c1nnc(*)s1]

or a pharmaceutically acceptable salt thereof.

5. The compound of claim 1, wherein Y is CH$_2$, or a pharmaceutically acceptable salt thereof.

6. The compound of claim 1 having the formula:

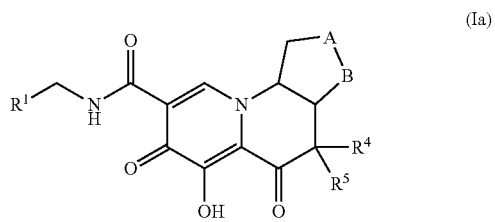

(Ia)

or a pharmaceutically acceptable salt thereof,
wherein:
the group -A-B— is selected from —CH$_2$—N(CH$_3$)—, —O—CH$_2$—, —O—CH$_2$—CH$_2$— and —CH$_2$—O—,
R$^1$ is phenyl, which is substituted by up to three R$^8$ groups,
R$^4$ is selected from C$_1$-C$_6$ alkyl and —(C$_1$-C$_6$ alkylene)—O—(C$_1$-C$_6$ alkyl); and
R$^5$ is C$_1$-C$_6$ alkyl.

7. The compound of claim 1, wherein R$^1$ is phenyl, which is substituted by 1 to 3 halo groups, which can be the same or different, or a pharmaceutically acceptable salt thereof.

8. The compound of claim 7, wherein R$^1$ is 2,4-difluorophenyl, 3-chloro-2,4-difluorophenyl or 3-chloro-2-fluorophenyl, or a pharmaceutically acceptable salt thereof.

9. The compound of claim 1, wherein the group -A-B— is —CH$_2$—O—, or a pharmaceutically acceptable salt thereof.

10. The compound of claim 1, wherein R$^4$ is —(C$_1$-C$_6$ alkylene)—O—(C$_1$-C$_6$ alkyl), or a pharmaceutically acceptable salt thereof.

11. The compound of claim 1, wherein R$^4$ is C$_1$-C$_6$ alkyl, or a pharmaceutically acceptable salt thereof.

12. The compound of claim 1, wherein R$^5$ is C$_1$-C$_6$ alkyl, or a pharmaceutically acceptable salt thereof.

13. The compound of claim 12, wherein R$^5$ is methyl, or a pharmaceutically acceptable salt thereof.

14. A compound selected from

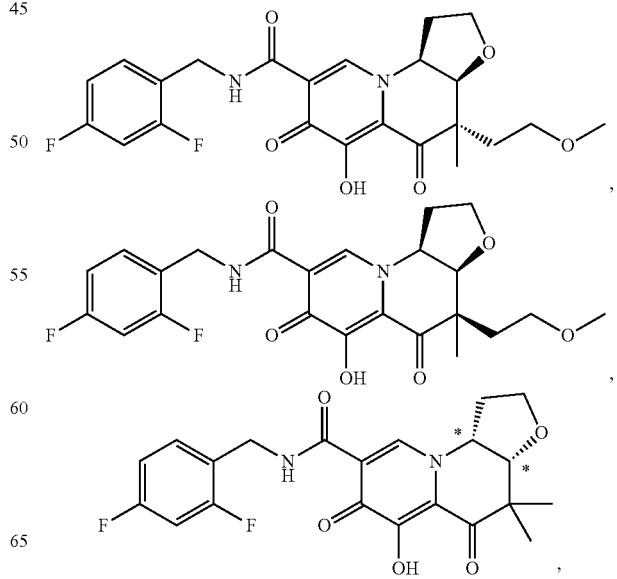

-continued

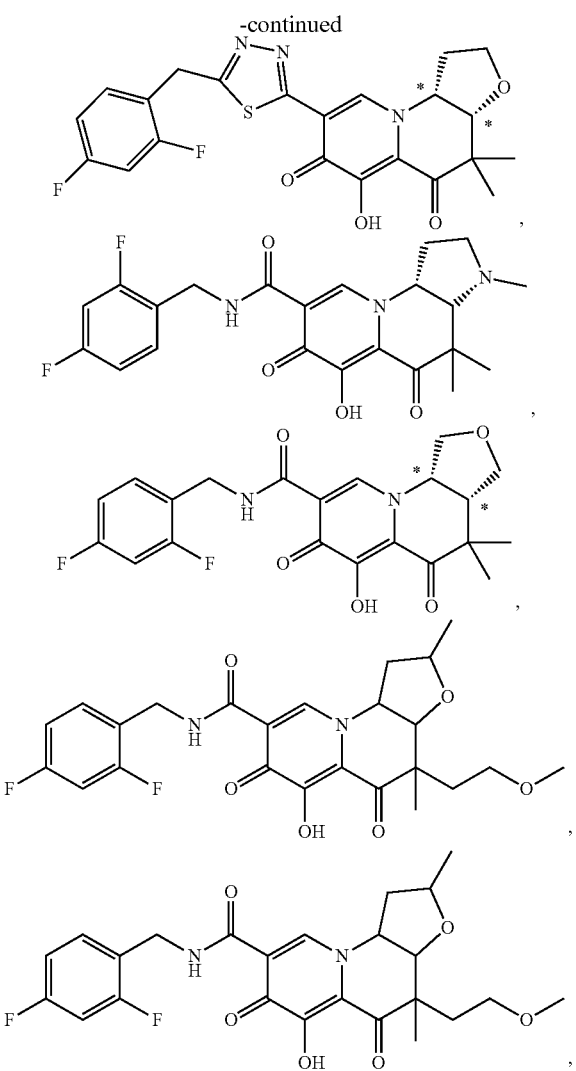

-continued

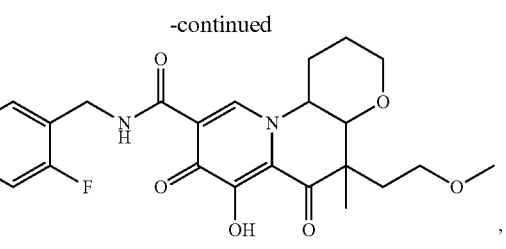

or a pharmaceutically acceptable salt thereof.

15. A pharmaceutical composition comprising an effective amount of a compound according to claim 1, or a pharmaceutically acceptable salt thereof, and a pharmaceutically acceptable carrier.

16. A method for the inhibition of HIV integrase in a subject in need thereof which comprises administering to the subject an effective amount of the compound according to claim 1, or a pharmaceutically acceptable salt thereof.

17. A method for the treatment of infection by HIV or for the treatment or delay in the onset or progression of AIDS in a subject in need thereof, which comprises administering to the subject an effective amount of the compound according to claim 1, or a pharmaceutically acceptable salt thereof.

18. The pharmaceutical composition of claim 15, further comprising one or more additional therapeutic agents selected from, lamivudine, abacavir, ritonavir, darunavir, atazanavir, emtricitabine, tenofovir, rilpivirine and lopinavir.

19. The method of claim 16, further comprising administering to the subject one or more additional therapeutic agents selected from, abacavir, lamivudine, ritonavir and lopinavir, wherein the amounts administered of the compounds are together effective to treat infection by HIV or to treat or delay the onset or progression of AIDS.

* * * * *